US011549941B2

(12) United States Patent
Berlin et al.

(10) Patent No.: US 11,549,941 B2
(45) Date of Patent: Jan. 10, 2023

(54) NUCLEIC ACID-FUNCTIONALIZED NANOPARTICLES

(71) Applicant: City of Hope, Duarte, CA (US)

(72) Inventors: Jacob Berlin, Monrovia, CA (US); Pamela Tiet, Glendale, CA (US)

(73) Assignee: CITY OF HOPE, Duarte, CA (US)

( * ) Notice: Subject to any disclaimer, the term of this patent is extended or adjusted under 35 U.S.C. 154(b) by 91 days.

(21) Appl. No.: 16/789,277

(22) Filed: Feb. 12, 2020

(65) Prior Publication Data

US 2020/0191781 A1 Jun. 18, 2020

Related U.S. Application Data

(63) Continuation of application No. 15/339,654, filed on Oct. 31, 2016, now abandoned.

(60) Provisional application No. 62/249,080, filed on Oct. 30, 2015.

(51) Int. Cl.
*G01N 33/543* (2006.01)
*G01N 33/553* (2006.01)
*G01N 21/64* (2006.01)

(52) U.S. Cl.
CPC ......... *G01N 33/54346* (2013.01); *G01N 21/6428* (2013.01); *G01N 33/553* (2013.01); *G01N 2021/6439* (2013.01); *G01N 2333/31* (2013.01)

(58) Field of Classification Search
CPC ......... G01N 33/54346; G01N 21/6428; G01N 33/553; G01N 2021/6439; G01N 2333/31
See application file for complete search history.

(56) References Cited

U.S. PATENT DOCUMENTS

| | | | |
|---|---|---|---|
| 5,194,372 A | * | 3/1993 | Nagai ............ C12Q 1/6827 435/6.12 |
| 6,214,552 B1 | | 4/2001 | Heroux et al. |
| 2001/0023063 A1 | | 9/2001 | Richter et al. |
| 2004/0002089 A1 | | 1/2004 | Dubertret et al. |
| 2014/0134609 A1 | | 5/2014 | Tan et al. |
| 2014/0199245 A1 | | 7/2014 | McNamara, II et al. |
| 2017/0122938 A1 | | 5/2017 | Berlin et al. |
| 2017/0172935 A1 | | 6/2017 | Oktem et al. |

FOREIGN PATENT DOCUMENTS

WO WO-2015/160317 A1 10/2015

OTHER PUBLICATIONS

Tiet et al, (Post Art) Colorimetric Detection of *Staphylococcus aureus* Contaminated Solutions without Purification, Bioconjugate Chem. 2017, 28, 183-193. (Year: 2017).*
Guo, L. et al. (Aug. 21, 2013, e-published Aug. 8, 2013). "Oriented gold nanoparticle aggregation for colorimetric sensors with surprisingly high analytical figures of merit," *J Am Chem Soc* 135(33):12338-12345.
Hernandez, F.J. et al. (Mar. 2014, e-published Feb. 2, 2014). "Noninvasive imaging of *Staphylococcus aureus* infections with a nuclease-activated probe," *NatMed* 20(3):301-306.
Kiedrowski, M.R. et al. (Apr. 21, 2014). "*Staphylococcus aureus* Nuc2 is a functional, surface-attached extracellular nuclease," *PLoS One* 9(4):e95574.
Liu, T. et al. (Jan. 1, 2010). Novel method to detect DNA methylation using gold nanoparticles coupled with enzyme-linkage reactions, *Anal Chem* 82(1):229-233.
Marcheggiani, S. et al. (May 22, 2015). "Detection of emerging and re-emerging pathogens in surface waters close to an urban area," *Int J Environ Res Public Health* 12(5):5505-5527.
Mirkin, C.A et al. (Aug. 15, 1996). "A DNA-based method for rationally assembling nanoparticles into macroscopic materials," *Nature* 382(6592):607-609.
Ray, P.C. et al. (Oct. 26, 2006). "Gold nanoparticle based FRET assay for the detection of DNA cleavage," *J Phys Chem B* 110(42):20745-20748.
Ray, P. C. et al. (Oct. 26, 2006). Supporting Information: "Gold nanoparticle based FRET assay for the detection of DNA cleavage," *J Phys Chem B* 110(42): pp. 1-2.
Wang, J. et al. (Jan. 21, 2012, e-published Dec. 13, 2011). "Phenylboronic acid functionalized gold nanoparticles for highly sensitive detection of *Staphylococcus aureus*," *Nanoscale* 4(2):451-454.

* cited by examiner

*Primary Examiner* — Narayan K Bhat
(74) *Attorney, Agent, or Firm* — Irina E. Britva; Mintz, Levin, Cohn, Ferris, Glovsky and Popeo, P.C.

(57) ABSTRACT

Provided herein are functionalized nanoparticle compositions and methods of using the same. The functionalized nanoparticles provided include a nuclease cleavage site and are, inter alia, useful for the formation of nanoparticle aggregates and detection of nuclease activity through nanoparticle aggregate formation.

17 Claims, 43 Drawing Sheets

Specification includes a Sequence Listing.

Scrambled

Participant #1

Participant #2

Participant #3

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: Residue modified by 2'-O-methyl
<220> FEATURE:
<221> NAME/KEY: misc_feature
<222> LOCATION: (7)..(11)
<223> OTHER INFORMATION: Residue modified by 2'-O-methyl

<400> SEQUENCE: 1
cucgttcguu c                                                          11
```

NUCLEIC ACID-FUNCTIONALIZED NANOPARTICLES

CROSS REFERENCE TO RELATED APPLICATIONS

This application claims priority to U.S. Provisional Application No. 62/249,080, filed Oct. 30, 2015, which is hereby incorporated by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-589C01US_SEQUENCE_LISTING_ST25.txt, created Feb. 3, 2020, 696 bytes, machine format IBM-PC, MS Windows operating system, is hereby incorporated by reference.

BACKGROUND OF THE INVENTION

More than 500,000 Americans contract staphylococcus infections in the US each year. Current clinical methods to detect staphylococcus can take 2-3 days to process, which delays the prognosis allowing the infection to progress. Early detection is essential to prevent acute symptoms from developing into chronic diseases such as endocarditis and osteomyelitis. Because current diagnostic procedures require hours to several days, there is an imminent need to create a point-of-care diagnostic platform that is rapid as well as sensitive, simple, and cost-effective. Provided herein are solutions to these and other problems in the art.

BRIEF SUMMARY OF THE INVENTION

In one aspect, a functionalized nanoparticle is provided. The functionalized nanoparticle includes a nanoparticle core and a nanoparticle coating. The nanoparticle coating includes a plurality of nucleic acid moieties bonded to the nanoparticle core and each of the nucleic acid moieties includes (i) a first linker binding the nucleic acid moiety to the nanoparticle core. And (ii) a single-stranded nucleic acid sequence of about 50 or less nucleotides in length covalently attached to the first linker, wherein the single-stranded nucleic acid sequence includes a nuclease cleavage site.

In one aspect, a plurality of functionalized nanoparticles is provided and each functionalized nanoparticle is a functionalized nanoparticle as provided herein including embodiments thereof.

In one aspect, a method of forming a nanoparticle aggregate is provided. The method includes (i) contacting a nuclease with the plurality of functionalized nanoparticles as provided herein including embodiments thereof. (ii) The nuclease is allowed to cleave the single-stranded nucleic acid sequence at the nuclease cleavage site of the plurality of functionalized nanoparticles, thereby forming a plurality of cleaved nanoparticles. (iii) The plurality of cleaved nanoparticles are allowed to bind to each other, thereby forming a nanoparticle aggregate.

In one aspect, a method of forming a nanoparticle aggregate is provided. The method includes (i) contacting a nuclease with the plurality of functionalized nanoparticles provided herein including embodiments thereof. (ii) The nuclease is allowed to cleave the single-stranded nucleic acid sequence at the nuclease cleavage site of the plurality of functionalized nanoparticles, thereby forming a nanoparticle aggregate.

BRIEF DESCRIPTION OF THE DRAWINGS

FIG. 1A. Oligo-AuNPs were tested by adding in MN and $CaCl_2$ followed by a 5 minute incubation in a 37° C. water bath after which a color change from red to purple occurred. FIG. 1B. Oligo-AuNPs were treated with 0.05 µM MN or RNase A. The $\lambda_{max}$ of the Oligo-AuNPs treated with MN is seen to shift from 530 nm to 570 nm and the solution experienced a color change from red to purple within 5 minutes.

FIG. 2A. 11-mer Oligo-AuNPs (0.5 nM) were treated with varying concentrations of MN to determine the limit of detection The limit of detection of Oligo-AuNPs treated with MN was 0.04 µM. FIG. 2B. Colorimetric changes in solution were seen when Oligo-AuNPs were treated with 0.04 µM to 9.917 µM MN. FIG. 2C. There was a shift in the UV-absorbance when Oligo-AuNPs were treated with 0.040 µM to 9.917 µM MN FIG. 2D. The limit of detection of Oligo-AuNPs treated with RNase A was 4.958 µM. FIG. 2E. Colorimetric changes in solution were seen when Oligo-AuNPs were treated with 4.958 µM to 9.917 µM RNase A. FIG. 2F There was a shift in the UV-absorbance when Oligo-AuNPs were treated with 4.958 µM to 9.917 µM RNase A.

FIG. 3A. The limit of detection of 5-mer Oligo-AuNPs treated with MN was 0.020 µM. FIG. 3B. Colorimetric changes in solution were seen when 5-mer Oligo-AuNPs were treated with 0.020 µM to 9.917 µM MN. FIG. 3C. The limit of detection of 5-mer Oligo-AuNPs treated with RNase A was 0.010 µM. FIG. 3D. Colorimetric changes in solution were seen when 5-mer Oligo-AuNPs were treated with 0.010 µM to 9.917 µM RNase A.

FIG. 4A. The Oligo-AuNPs could be lyophilized for long-term storage and reconstituted in water or sample of interest. FIG. 4B. Shows that after lyophilization, 200 µL of $H_2O$ spiked with various concentration of MN were used to re-disperse the Oligo-AuNPs. The limit of detection of the lyophilized Oligo-AuNPs was determined to be 0.040 µM MN. FIG. 4C. Colorimetric changes in solution were seen when lyophilized Oligo-AuNPs were treated with 0.040 µM to 9.917 µM MN. FIG. 4D. The limit of detection of lyophilized Oligo-AuNPs treated with MN-spiked creek water was 0.040 µM MN. FIG. 4E. Colorimetric changes in solution were seen when lyophilized Oligo-AuNPs were treated with 0.040 µM to 9.917 µM MN spiked in creek water. FIG. 4F. The limit of detection of lyophilized Oligo-AuNPs treated with MN-spiked ocean water was 4.958 µM MN. FIG. 4G. Colorimetric changes in solution were seen when lyophilized Oligo-AuNPs were treated with 4.958 µM to 9.917 µM MN spiked in ocean water.

FIG. 5A. The various *S. aureus* supernatants caused aggregation to occur and the $\lambda_{max}$ to shift from 530 nm to 570 nm. FIG. 5B. Treatment with various *S. aureus* supernatants resulted in a color change from red to purple in solution. FIG. 5C. DLS measurements showed a significant increase in diameter when the various *S. aureus* supernatants were used to treat Oligo-AuNPs. FIG. 5D. TSB, *A. baumannii*, *S. pneumoniae*, and *S. epidermidis* treated Oligo-AuNPs were monodisperse by TEM, however, particles treated with any of the *S. aureus* supernatants underwent mass aggregation. 6500× magnification, inset: 30000× magnification.

FIG. 6A. The 11-mer Oligonucleotide was digested with 9.917 µM MN and analyzed by LC-MS. MN w/Ca cleaved the 11-mer into even smaller oligonucleotides, whereas MN w/o Ca primarily cleaved the 11-mer between the unmodified deoxythymidines, which yielded 6-mers. The addition of EDTA suppressed cleavage from occurring. FIG. 6B. RNase A (0.126 µM) was used to digest the 11-mer oligonucleotide as a negative control. In all conditions, no cleavage peaks appeared and the 11-mer was left intact.

FIGS. 9A-9C. 11-mer Oligo-AuNPs (0.25 nM) were treated with varying concentrations of MN to determine the limit of detection. There was a shift in the UV-absorbance and a color change in solution when Oligo-AuNPs were treated with 0.040 µM to 9.917 µM MN. FIGS. 9D-9F. 11-mer Oligo-AuNPs (1 nM) were treated with varying concentrations of MN to determine the limit of detection. There was a shift in the UV-absorbance and a color change in solution when Oligo-AuNPs were treated with 0.050 µM to 9.917 µM MN.

FIGS. 10A-10C. 11-mer Oligo-AuNPs (0.5 nM) were stable in solution from pH 4-10 and the $\lambda_{max}$ remained at 530 nm. FIGS. 10D-10F. 11-mer Oligo-AuNPs (0.5 nM) were treated with varying concentrations of MN at pH 4 to determine the limit of detection. There was a shift in the UV-absorbance and a color change in solution when Oligo-AuNPs were treated with 0.040 µM to 9.917 µM MN. FIGS. 10G-10I. 11-mer Oligo-AuNPs (0.5 nM) were treated with varying concentrations of MN at pH 10 to determine the limit of detection. There was a shift in the UV-absorbance and a color change in solution when Oligo-AuNPs were treated with 0.040 µM to 9.917 µM MN.

FIG. 12A. The 11-mer and 5-mer Oligo-AuNPs had an equivalent $\lambda_{max}$ at 530 nm. FIG. 12B. TEM images were taken of the 11-mer Oligo-AuNPs (30,000× magnification). FIG. 12C. TEM images were taken of the 5-mer Oligo-AuNPs (30,000× magnification).

FIG. 13A. 5-mer Oligo-AuNPs (0.5 nM) were treated with varying concentrations of MN to determine the limit of detection. There was a shift in the UV-absorbance when Oligo-AuNPs were treated with 0.020 µM to 9.917 µM MN. FIG. 13B. 5-mer Oligo-AuNPs (0.5 nM) were treated with varying concentrations of RNase A to determine the limit of detection. There was a shift in the UV-absorbance when Oligo-AuNPs were treated with 0.010 µM to 9.917 µM RNase A.

FIG. 14A. Lyophilized 11-mer Oligo-AuNPs (0.5 nM) were treated with varying concentrations of MN to determine the limit of detection. There was a shift in the UV-absorbance when Oligo-AuNPs were treated with 0.040 µM to 9.917 µM MN. FIG. 14B. Lyophilized 11-mer Oligo-AuNPs (0.5 nM) were treated with varying concentrations of MN spiked into creek water to determine the limit of detection. There was a shift in the UV-absorbance when Oligo-AuNPs were treated with 0.040 µM to 9.917 µM MN. FIG. 14C. Lyophilized 11-mer Oligo-AuNPs (0.5 nM) were treated with varying concentrations of MN spiked into ocean water to determine the limit of detection. There was a shift in the UV-absorbance when Oligo-AuNPs were treated with 4.958 µM to 9.917 µM MN.

FIG. 15A. The minimum volume of S. aureus WT supernatant needed was 10 µL. Using 10 the $\lambda_{max}$ shifted to 560 nm. The study was drawn out to 1 hour in order to allow the lower volumes (1 µL-5 µL) of S. aureus WT supernatant used more time to digest since the max for these conditions did not shift after 5 minutes. FIG. 15B. A colorimetric change in solution from red to purple occurred within 5 minutes when 10 µL to 100 µL of S. aureus supernatant was used. After extending the incubation time to 1 hour, the lower volumes (1 µL-5 µL) of S. aureus WT supernatant used to treat Oligo-AuNPs did not undergo a color change.

FIG. 16A. Two different sets of supernatants from S. aureus WT, S. aureus nuc1-, S. aureus nuc1-nuc2-, S. epidermidis, S. pneumoniae, and A. baumannii were analyzed for MN expression by Western blot. Supernatant from S. aureus WT is the only condition that expressed MN, meaning that complete knock-out of MN was successful in S. aureus nuc1- and S. aureus nuc1-nuc2-. FIG. 16B. Western blots were performed on all of the supernatants to determine MN expression. S. aureus is the only bacteria that expresses MN.

FIG. 17A. 11-mer Oligo-AuNPs (0.5 nM) were treated with TSB or supernatant from S. aureus WT, S. aureus nuc1-, and S. aureus nuc1-nuc2- in the presence of 2 mM CaCl$_2$ for 5 minutes. There was a shift in $\lambda_{max}$ from 530 nm to 570 nm for the S. aureus conditions. FIG. 17B. 11-mer Oligo-AuNPs (0.5 nM) were treated with TSB or supernatant from S. aureus WT, S. aureus nuc1-, and S. aureus nuc1-nuc2- in the presence of 2 mM CaCl$_2$ for 1 hour. There was a shift in $\lambda_{max}$ from 530 nm to 570 nm for the S. aureus conditions and a decrease in absorbance due to aggregation of the Oligo-AuNPs. FIG. 17C. 11-mer Oligo-AuNPs (0.5 nM) were treated with TSB or supernatant from S. aureus WT, S. aureus nuc1-, and S. aureus nuc1-nuc2- without CaCl$_2$ for 5 minutes. Supernatant from S. aureus caused a shift in $\lambda_{max}$ from 530 nm to 560 nm. S. aureus nuc1- and S. aureus nuc1-nuc2- did not cause a shift in UV absorbance. FIG. 17D. 11-mer Oligo-AuNPs (0.5 nM) were treated with TSB or supernatant from S. aureus WT, S. aureus nuc1-, and S. aureus nuc1-nuc2- without CaCl$_2$ for 1 hour. Supernatant from S. aureus caused a shift in $\lambda_{max}$ from 530 nm to 570 nm. S. aureus nuc1- caused a shift in in $\lambda_{max}$ from 530 nm to 545 nm and S. aureus nuc1-nuc2- caused a shift in $\lambda_{max}$ from 530 nm to 540 nm. FIG. 17E-17F. 11-mer Oligo-AuNPs (0.5 nM) were treated with TSB or supernatant from S. aureus WT, S. aureus nuc1-, and S. aureus nuc1-nuc2- with CaCl$_2$ and EDTA for both 5 minutes and 1 hour. After 5 minutes or 1 hour, no shift in the UV absorbance was seen.

FIG. 19B. Oglio-AuNPs have similar UV absorbance to unfunctionalized 20 nm particles (530 nm). FIG. 19C. TEM images that were taken of functionalized Oglio-AuNPs; 6500× magnification, small inset: 30,000× magnification.

FIG. 22A. The Oligo-AuNPs are monodisperse and red in solution before enzymatic cleavage. FIG. 22B. Following the addition of the nuclease which causes Oligo-AuNPs to aggregate and become polydisperse, there is a colorimetric change from red to purple.

FIG. 26A shows 50 nm Oligo-AuNPs prior to enzymatic treatment. FIG. 26B shows 50 nm Oligo-AuNPs post to enzymatic treatment. The addition of the nuclease causes the monodisperse 50 nm AuNPs to aggregate, which leads to a colorimetric change in solution.

FIG. 28A shows Oligonucleotide-functionalized 20 nm AuNPs and FIG. 28C shows RNASE treated oligonucleotide-functionalized 20 nm AuNPs remain stable and monodisperse in solution. FIG. 28B. Oligonucleotide-functionalized 20 m AuNPs were cleaved with the micrococcal endonuclease, causing the AuNPs to aggregate.

DETAILED DESCRIPTION OF THE INVENTION

I. Definitions

Figure 1A:
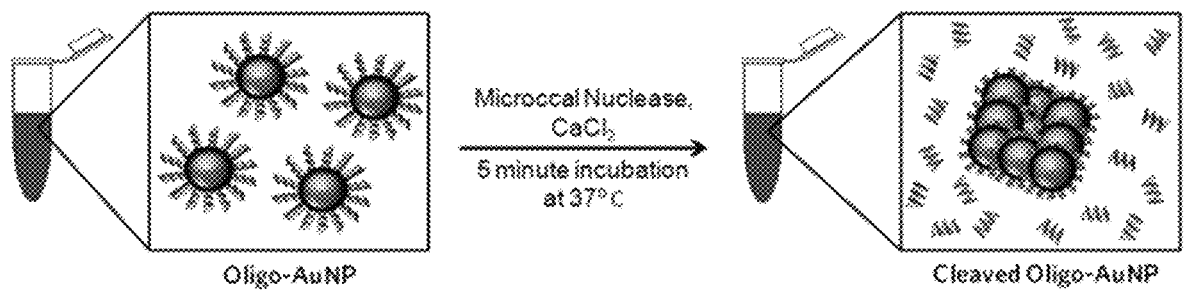
FIGS. 1A-1B. Characterization of Oligo-AuNPs and aggregation of the Oligo-AuNPs after MN treatment.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. The heteroatom(s) O, N, P, S, Se, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Heteroalkyl is not cyclized. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O) CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN, —NO₂, —R', —N₃, —CH(Ph)₂, fluoro(C₁-C₄)alkoxy, and fluoro(C₁-C₄)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —S—, —S(O)—, —S(O)₂—, or —S(O)₂NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH₂, —SH, —CN, —CF₃, —NO₂, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different (i.e. independently substituted). Where a particular R group is present in the description of a chemical genus (such as Formula (I)), a Roman alphabetic symbol may be used to distinguish each appearance of that particular R group. For example, where multiple $R^3$ substituents are present, each $R^3$ substituent may be distinguished as $R^{3A}$, $R^{3B}$, $R^{3C}$, $R^{3D}$, etc., wherein each of $R^{3A}$, $R^{3B}$, $R^{3C}$, $R^{3D}$, etc. is defined within the scope of the definition of $R^3$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids provided herein can include one or more reactive moieties. As used herein, the term reactive moiety includes any group capable of reacting with another molecule, e.g., a nucleic acid or polypeptide through covalent, non-covalent or other interactions. By way of example, the nucleic acid can include a chemical reactive moiety that reacts with a reactive group in the linker (first or second linker provided herein) through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a first moiety (e.g. a nucleic acid) and a second moiety (e.g., a moiety of the nanoparticle core, the water soluble moiety) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., nucleic acid moiety) is non-covalently attached to the second moiety on the nanoparticle core through a non-covalent chemical reaction between a component of the first moiety (e.g., nucleic acid moiety) and a component of the second moiety on the nanoparticle core. In other embodiments, the first moiety (e.g., nucleic acid moiety) includes one or more reactive moieties, e.g., a covalent reactive moiety, as described herein (e.g., alkyne, azide, maleimide or thiol reactive moiety). In other embodiments, the first moiety (e.g., nucleic acid moiety) includes a linker (e.g., first linker) with one or more reactive moieties, e.g., a covalent reactive moiety, as described herein (e.g., alkyne, azide, maleimide or thiol reactive moiety). In other embodiments, the nanoparticle core includes one or more reactive moieties, e.g., a covalent reactive moiety, as described herein (e.g., alkyne, azide, maleimide or thiol reactive moiety). In other embodiments, the nanoparticle core includes a linker with one or more reactive moieties, e.g., a covalent reactive moiety, as described herein (e.g., alkyne, azide, maleimide or thiol reactive moiety).

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(i) metal silicon oxide bonding; and (l) metal bonding to reactive phosphorus groups (e.g. phosphines) to form, for example, phosphate diester bonds.

The reactive functional groups can be chosen such that they do not participate in, or interfere with, the chemical stability of the functionalized nanoparticles described herein. Alternatively, a reactive functional group can be protected from participating in the crosslinking reaction by the presence of a protecting group.

Linkers may also be employed to connect the nanoparticle core and the nucleic acid moiety or the single stranded nucleic acid sequence to the water soluble moiety. Linkers may include the residue of reactive groups at the point of attachment of the nanoparticle core, the single-stranded nucleic acid, the first linker, the second linker and/or the water soluble moiety. Any linkers include substituted or unsubstituted alkylene, substituted or unsubstituted heteroalkylene, substituted or unsubstituted cycoalkylene, substituted or unsubstituted heterocycloalkylene, substituted or unsubstituted arylene, and substituted or unsubstituted heteroarylene.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments contacting includes, for example, allowing a ribonucleic acid as described herein to interact with an endonuclease.

The term "contacting" may include allowing two species to react, interact, or physically touch, wherein the two species may be, for example, a linker as described herein and a nanoparticle core. In embodiments contacting includes, for example, allowing a linker described herein to interact with a nucleic acid moiety provided herein.

A "control" sample or value refers to a sample that serves as a reference, usually a known reference, for comparison to a test sample. For example, a test sample can be taken from a test condition, e.g., in the presence of a nuclease activity, and compared to samples from known conditions, e.g., in the absence of the nuclease activity (negative control), or in the presence of a known compound or nuclease activity (positive control). A control can also represent an average value gathered from a number of tests or results. One of skill in the art will recognize that controls can be designed for assessment of any number of parameters. One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variable in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

Lengths and sizes of nanoparticles and functionalized nanoparticles as described herein may be measured using Transmission Electron Microscopy. All exemplified nanoparticle core length values reported herein may be measured using the following protocol. For the transmission electron microscopy measurements the various gold nanoparticle samples were drop coated (5 μL) onto 200 mesh copper EM grids, air-dried and imaged using a FEI Tecnai 12 TEM equipped with a Gatan Ultrascan 2K CCD camera at an accelerating voltage of 120 kV. The average size distributions of the particles were obtained from the TEM images using Image J (version 1.4.3) software that were plotted using Origin Pro 8 software to obtain the histogram size distributions of the particles. In embodiment, the length of a nanoparticle refers to the longest dimension of the particle.

A "water soluble moiety" as used herein refers to any moiety that enhances the water solubility of a nanoparticle to which it is bound or otherwise serves to prevent the functionalized nanoparticles from accumulating or aggregating. A water soluble moiety may alter the partitioning coefficient of a nanoparticle thereby making the nanoparticle more or less hydrophilic. Generally, greater hydrophobicity correlates to a higher partition constant. Likewise, generally, greater hydrophilicity correlates to a lower partition constant. In embodiments, the water soluble group decreases the partition constant of precursor molecules (which have a higher partition constant before attachment of the water soluble group) at least by about 10%, 20%, 30%, 40%, 50%, 60%, 70%, 80%, or 90%. In embodiments, the water soluble groups described herein can decrease the partition constant of the plurality of nucleic acid moieties of the nanoparticle coating by 1-fold, 2-fold, 3-fold, 4-fold, or greater. Exemplary water soluble moieties include moieties (e.g. monovalent forms) such as poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like (including linear chains or branched chains); polyethylene glycol moieties of formula

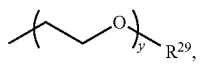

wherein y is an integer from 1 to 50 and $R^{29}$ is —H or -Me (where the left side of the formula is the point of attachment to the remainder of the molecule); polyvinylpyroolidone moieties; or poly 2-ethyl oxazoline moieties. Water soluble molecules may exist in polymeric form wherein at least two monomers are repeatedly covalently connected.

In embodiments, the water soluble group can include a moiety containing a heteroatom (e.g., oxygen or nitrogen). In embodiments, the moiety contains an alcohol moiety (an organic moiety having an —OH bound to a carbon atom), ester linker moiety (the linker moiety —C(O)O— between two carbon atoms), ether linker moiety (the linker moiety —O— between two carbon atoms), amine (—NH$_2$) moiety, nitrile (—CN) moiety, ketone moiety (the linker moiety —C(O)— between two carbon atoms), or aldehyde (—C(O)H) moiety.

The nanoparticles of the present invention may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

For specific proteins described herein (e.g., Eap (extracellular adherence protein), bifunctional autolysin, protein A (membrane-bound), immunodominant staphylococcal antigen B), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "*Staphylococcus aureus* micrococcal nuclease", "micrococcal nuclease", "Staph MNase" or "MNase" as referred to herein includes any of the recombinant or naturally-occurring forms of the *Staphylococcus aureus* micrococcal nuclease (MNase) or variants or homologs thereof that maintain MNase activity (e.g. within at least 50%, 80%, 90%, 95%, 96%, 97%, 98%, 99% or 100% activity compared to MNase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MNase. In embodiments, the MNase is substantially identical to the protein identified by the CAS registry reference number 9013-53-0 or a variant or homolog having substantial identity thereto.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

II. COMPOSITIONS

Provided herein are functionalized nanoparticles that are, inter alia, useful for the detection of a nuclease activity (e.g., micrococcal nuclease). The functionalized nanoparticles provided herein include a nanoparticle core and a nanoparticle coating. The nanoparticle coating includes a plurality of nucleic acid moieties which each include a first linker. The first linker connects the nucleic acid moiety to the nanoparticle core. Each nucleic acid moiety includes a single-stranded nucleic acid sequence bound to the nanoparticle core through a first linker. The single-stranded nucleic acid sequence is about 50 or less nucleotides in length and includes a nuclease (e.g., a micrococcal nuclease) cleavage site. Thus, in one aspect a functionalized nanoparticle is provided. The functionalized nanoparticle includes a nanoparticle core and a nanoparticle coating. The nanoparticle coating includes a plurality of nucleic acid moieties bonded to the nanoparticle core and each of the nucleic acid moieties includes (i) a first linker binding the nucleic acid moiety to the nanoparticle core. And (ii) a single-stranded nucleic acid sequence of about 50 or less nucleotides in length covalently attached to the first linker, wherein the single-stranded nucleic acid sequence includes a nuclease cleavage site.

In embodiments, the functionalized nanoparticle consists essentially of (e.g., consists of) a nanoparticle core and a nanoparticle coating. The nanoparticle coating consists essentially of (e.g., consists of) a plurality of nucleic acid moieties bonded to the nanoparticle core and each of the nucleic acid moieties consists essentially of (e.g., consists of) (i) a first linker binding the nucleic acid moiety to the nanoparticle core and (ii) a single-stranded nucleic acid sequence of about 50 or less nucleotides in length covalently attached to the first linker, wherein the single-stranded nucleic acid sequence consists essentially of (e.g., consists of) a nuclease cleavage site.

In embodiments, the functionalized nanoparticle consists essentially of a nanoparticle core and a nanoparticle coating if the nanoparticle core is not further attached or does not further include anything than a first non-reacted linker precursor. A "non-reacted linker precursor" as provided herein is a chemical moiety that is capable of reacting with a reactive moiety or reactive functional group (e.g., a carboxyl functional group) of the first linker. The non-reacted linker precursor may be reacted with the reactive moiety of the first linker through any of the conjugate chemistries described herein. For example a non-reacted linker precursor may be an amine or alcohol reacted with an acyl halide, an active ester hydroxyl group reacted to ester, ether or aldehyde, a thiol group reacted to a disulfide.

In embodiments, the functionalized nanoparticle consists essentially of a nanoparticle core and a nanoparticle coating if the nanoparticle core is not further attached to or does not further include anything than a plurality of nucleic acid moieties described herein. In embodiments, the functionalized nanoparticle consists essentially of a nanoparticle core and a nanoparticle coating if the nanoparticle core is not further attached to or does not further include a biomolecule, a polypeptide moiety, a peptide moiety, a nucleic acid moiety, a carbohydrate moiety, an enzyme moiety, an oligosaccharide moiety, a polysaccharide moiety, a polymer moiety, a steroid moiety, a therapeutic moiety (e.g., drug, small molecule), a detectable moiety (e.g., a fluorescent moiety, luminescent moiety, colorimetric moiety, phosphorescent moiety, radioactive moiety or electroactive moiety), a pharmaceutically reactive moiety, a prodrug moiety, a conjugate chemistry reactive moiety, a contrast agent moiety (e.g., a magnetic resonance imaging (MRI) moiety, atomic force microscopy (AFM) moiety, transmission electron microscopy (TEM) moiety, Raman spectroscopy moiety, ultra-violet spectroscopy (UV-Vis) moiety, X-Ray diffraction moiety), a water soluble moiety or a cleavable moiety (e.g., an enzymatic cleavable moiety, a metal cleavable moiety, an acid cleavable moiety, a redox cleavable moiety, a photo-cleavable moiety, an electrically cleavable moiety.

In embodiments, the nanoparticle coating consists essentially of (e.g., consists of) a plurality of nucleic acid moieties bonded to the nanoparticle core. In embodiments, the nanoparticle coating consists essentially of (e.g., consists of) a plurality of nucleic acid moieties bonded to the nanoparticle core if the nanoparticle coating is not further attached to or does not further include anything than a plurality of nucleic acid moieties described herein. In embodiments, the nanoparticle coating consists essentially of (e.g., consists of) a plurality of nucleic acid moieties bonded to the nanoparticle core if the nanoparticle coating is not further attached to or does not further include a biomolecule, a polypeptide moiety, a peptide moiety, a nucleic acid moiety, a carbohydrate moiety, an enzyme moiety, an oligosaccharide moiety, a polysaccharide moiety, a polymer moiety, a steroid moiety, a therapeutic moiety (e.g., drug, small molecule), a detectable moiety (e.g., a fluorescent moiety, luminescent moiety, colorimetric moiety, phosphorescent moiety, radioactive moiety or electroactive moiety), a pharmaceutically reactive moiety, a prodrug moiety, a conjugate chemistry reactive moiety, a contrast agent moiety (e.g., a magnetic resonance imaging (MRI) moiety, atomic force microscopy (AFM) moiety, transmission electron microscopy (TEM) moiety, Raman spectroscopy moiety, ultra-violet spectroscopy (UV-Vis) moiety, X-Ray diffraction moiety), a water soluble moiety or a cleavable moiety (e.g., an enzymatic cleavable moiety, a metal cleavable moiety, an acid cleavable moiety, a redox cleavable moiety, a photo-cleavable moiety, an electrically cleavable moiety.

In embodiments, each of the nucleic acid moieties consists essentially of (e.g., consists of) a first linker binding the nucleic acid moiety to the nanoparticle core. In embodiments, each of the nucleic acid moieties consists essentially of (e.g., consists of) a first linker binding the nucleic acid moiety to the nanoparticle core, if the nucleic acid moiety is not further attached to or does not further include anything than a first linker binding the nucleic acid moiety to the nanoparticle core described herein. In embodiments, the nucleic acid moieties consist essentially of a first linker binding the nucleic acid moiety to the nanoparticle core if the nucleic acid moiety is not further attached to or does not further include a biomolecule, a polypeptide moiety, a peptide moiety, a nucleic acid moiety, a carbohydrate moiety, an enzyme moiety, an oligosaccharide moiety, a polysaccharide moiety, a polymer moiety, a steroid moiety, a therapeutic moiety (e.g., drug, small molecule), a detectable moiety (e.g., a fluorescent moiety, luminescent moiety, colorimetric moiety, phosphorescent moiety, radioactive moiety or electroactive moiety), a pharmaceutically reactive moiety, a prodrug moiety, a conjugate chemistry reactive moiety, a contrast agent moiety (e.g., a magnetic resonance imaging (MRI) moiety, atomic force microscopy (AFM) moiety, transmission electron microscopy (TEM) moiety, Raman spectroscopy moiety, ultra-violet spectroscopy (UV-Vis) moiety, X-Ray diffraction moiety), a water soluble moiety or a cleavable moiety (e.g., an enzymatic cleavable moiety, a metal cleavable moiety, an acid cleavable moiety, a redox cleavable moiety, a photo-cleavable moiety, an electrically cleavable moiety.

In embodiments, the single-stranded nucleic acid sequence consists essentially of (e.g., consists of) a nuclease cleavage site. In embodiments, the single-stranded nucleic acid sequence consists essentially of (e.g., consists of) a nuclease cleavage site, if the single-stranded nucleic acid sequence is not further attached to or does not further include anything than a nuclease cleavage site described herein. In embodiments, the single-stranded nucleic acid sequence consists essentially of a nuclease cleavage site, if the single-stranded nucleic acid sequence is not further attached to or does not further include a biomolecule, a polypeptide moiety, a peptide moiety, a nucleic acid moiety, a carbohydrate moiety, an enzyme moiety, an oligosaccharide moiety, a polysaccharide moiety, a polymer moiety, a steroid moiety, a therapeutic moiety (e.g., drug, small molecule), a detectable moiety (e.g., a fluorescent moiety, luminescent moiety, colorimetric moiety, phosphorescent moiety, radioactive moiety or electroactive moiety), a pharmaceutically reactive moiety, a prodrug moiety, a conjugate chemistry reactive moiety, a contrast agent moiety (e.g., a magnetic resonance imaging (MRI) moiety, atomic force microscopy (AFM) moiety, transmission electron microscopy (TEM) moiety, Raman spectroscopy moiety, ultra-violet spectroscopy (UV-Vis) moiety, X-Ray diffraction moiety), a water soluble moiety or a cleavable moiety (e.g., an enzymatic cleavable moiety, a metal cleavable moiety, an acid cleavable moiety, a redox cleavable moiety, a photo-cleavable moiety, an electrically cleavable moiety.

In embodiments, the functionalized nanoparticle consists essentially of (e.g., consists of) a nanoparticle core and a nanoparticle coating. The nanoparticle coating consists essentially of (e.g., consists of) a plurality of nucleic acid moieties bonded to the nanoparticle core and each of the nucleic acid moieties consists essentially of (e.g., consists of) (i) a first linker binding the nucleic acid moiety to the nanoparticle core and (ii) a single-stranded nucleic acid sequence of about 50 or less nucleotides in length covalently attached to the first linker, wherein the single-stranded nucleic acid sequence includes a nuclease cleavage site.

In embodiments, the functionalized nanoparticle consists essentially of (e.g., consists of) a nanoparticle core and a nanoparticle coating. The nanoparticle coating consists essentially of (e.g., consists of) a plurality of nucleic acid moieties bonded to the nanoparticle core and each of the nucleic acid moieties includes (i) a first linker binding the nucleic acid moiety to the nanoparticle core and (ii) a single-stranded nucleic acid sequence of about 50 or less nucleotides in length covalently attached to the first linker, wherein the single-stranded nucleic acid sequence includes a nuclease cleavage site.

In embodiments, the functionalized nanoparticle consists essentially of (e.g., consists of) a nanoparticle core and a nanoparticle coating. The nanoparticle coating consists essentially of (e.g., consists of) a plurality of nucleic acid moieties bonded to the nanoparticle core and each of the nucleic acid moieties includes (i) a first linker binding the nucleic acid moiety to the nanoparticle core and (ii) a single-stranded nucleic acid sequence of about 50 or less nucleotides in length covalently attached to the first linker, wherein the single-stranded nucleic acid sequence consists essentially of (e.g., consists of) a nuclease cleavage site.

In embodiments, the functionalized nanoparticle consists essentially of (e.g., consists of) a nanoparticle core and a nanoparticle coating. The nanoparticle coating includes a plurality of nucleic acid moieties bonded to the nanoparticle core and each of the nucleic acid moieties includes (i) a first linker binding the nucleic acid moiety to the nanoparticle core and (ii) a single-stranded nucleic acid sequence of about 50 or less nucleotides in length covalently attached to the first linker, wherein the single-stranded nucleic acid sequence includes a nuclease cleavage site.

The nanoparticle core of the functionalized nanoparticles provided herein including embodiments thereof may be about 3 nm to about 20 nm in length. The nanoparticle core may be about 3 nm to about 15 nm in length. The nanoparticle core may be about 3 nm to about 10 nm in length. The nanoparticle core may be about 3 nm to about 8 nm in length. The nanoparticle core may be about 3 nm to about 6 nm in length. The nanoparticle core may be about 3 nm to about 5 nm in length.

The nanoparticle core may be about 3, 4, 5, 6, 7, 8, 9, 10, 11, 12, 13, 14, 15, 16, 17, 18, 19, or 20 nm in length. The nanoparticle core may be about 3, 4, 5, 6, 7, 8, 9, 10, 11, 12, 13, 14 or 15 nm in length. The nanoparticle core may be about 3, 4, 5, 6, 7, 8, 9 or 10 nm in length. The nanoparticle core may be about 3, 4, 5, 6, 7 or 8 nm in length. The nanoparticle core may be about 3, 4, 5 or 6 nm in length. The nanoparticle core may be about 3 nm in length. The nanoparticle core may be about 4 nm in length. The nanoparticle core may be about 5 nm in length. The nanoparticle core may be about 6 nm in length. The nanoparticle core may be about 7 nm in length. The nanoparticle core may be about 8 nm in length. The nanoparticle core may be about 9 nm in length. The nanoparticle core may be about 10 nm in length.

The nanoparticle core is typically composed of non-toxic material. The nanoparticle core may be an inorganic nanoparticle core. The inorganic nanoparticle core may be a metal nanoparticle core. When the nanoparticle core is a metal, the metal may be titanium, zirconium, gold, silver, platinum, cerium, arsenic, iron, aluminum or silicon. The metal nanoparticle core may be titanium, zirconium, gold, silver, or platinum and appropriate metal oxides thereof. In embodiments, the nanoparticle core is titanium oxide, zirconium oxide, cerium oxide, arsenic oxide, iron oxide, aluminum oxide, or silicon oxide. The metal oxide nanoparticle core may be titanium oxide or zirconium oxide. The nanoparticle may be titanium. The nanoparticle may be gold. In embodiments, the metal nanoparticle core is a gold nanoparticle core. Alternatively, the nanoparticle core may be a polymeric core. Such polymeric cores may include titanium, zirconium, gold, silver, platinum, cerium, arsenic, iron, aluminum or silicon.

In embodiments, the polymeric core includes an outer shell layer and an inner shell layer and the outer shell layer is chemically distinct from the inner shell layer. In embodiments, the outer shell layer and inner shell layer may be a metal such as titanium, gold or silver coated by another metal. Exemplary non-limiting outer and inner shell layer combinations include titanium/gold, titanium/silver, titanium/silicon, gold/titanium, gold/silver, gold/silicon, silicon/titanium, silicon/gold, or silicon/silver. In embodiments, the nanoparticle core includes a combination of metals coated by titanium, zirconium, gold, silver platinum or silicon. The nanoparticle core may be a quantum dot.

The nucleic acid moiety provided herein is connected to the nanoparticle core through a first linker. In embodiments, the nucleic acid moiety has the formula:

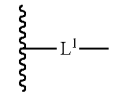

single-stranded nucleic acid sequence. The first linker or $L^1$ may be a chemical linker that connects the nanoparticle core to the single-stranded nucleic acid sequence. In embodiments, $L^1$ is a divalent linker formed by reacting a functional (reactive) group attached to the single-stranded nucleic acid sequence with the nanoparticle core (e.g. a functional (reactive) group on the nanoparticle core). $L^1$ may be a bond, —S—, —OSi(OR$^5$)(OR$^6$)(O)—, or —OP(O)(OR$^7$)(O)—. $R^5$, $R^6$, and $R^7$ are independently hydrogen, substituted or unsubstituted alkyl (e.g. $C_1$-$C_5$), substituted or unsubstituted heteroalkyl (2 to 5 membered heteroalkyl), substituted or unsubstituted cycloalkyl (3 to 6 membered cycloalkyl), substituted or unsubstituted heterocycloalkyl (2 to 6 membered heterocycloalkyl), substituted or unsubstituted aryl (2 to 6 membered aryl), or substituted or unsubstituted heteroaryl (2 to 6 membered heteroaryl). $R^5$, $R^6$, and $R^7$ may independently be hydrogen, substituted or unsubstituted alkyl (e.g. $C_1$-$C_5$). $R^5$, $R^6$, and $R^7$ may independently be hydrogen or unsubstituted alkyl (e.g. $C_1$-$C_5$).

In embodiments, $L^1$ is a bond, —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene (e.g. $C_1$-$C_{10}$), substituted or unsubstituted heteroalkylene (e.g. 2 to 10 heteroalkylene), substituted or unsubstituted cycloalkylene (e.g. 3 to 8 membered cycloalkylene), substituted or unsubstituted heterocycloalkylene (e.g. 3 to 8 membered heterocycloalkylene), substituted or unsubstituted arylene (e.g. 3 to 8 membered arylene), or substituted or unsubstituted heteroarylene (e.g. 3 to 8 membered heteroarylene), an amino acid sequence linker, or a nucleic acid sequence linker. $R^1$, $R^2$, $R^3$ and $R^4$, are independently hydrogen, halogen, $-N_3$, $-NO_2$, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-OCH_3$, $-NHCNHNH_2$, substituted or unsubstituted alkyl (e.g. $C_1$-$C_{10}$), substituted or unsubstituted heteroalkyl (e.g. 2 to 10 heteroalkyl), substituted or unsubstituted cycloalkyl (e.g. 3 to 8 membered cycloalkyl), substituted or unsubstituted heterocycloalkyl (e.g. 3 to 8 membered heterocycloalkyl), substituted or unsubstituted aryl (e.g. 3 to 8 membered aryl), or substituted or unsubstituted heteroaryl (e.g. 3 to 8 membered heteroaryl). The symbol n is independently 1 or 2.

$L^1$ may be $C_1$-$C_5$ substituted or unsubstituted alkylene (e.g. unsubstituted). $L^1$ may be 3 to 7 membered substituted or unsubstituted heteroalkylene (e.g. unsubstituted). $L^1$ may be 5 to 6 membered substituted or unsubstituted cycloalkylene (e.g. unsubstituted). $L^1$ may be 5 to 6 membered substituted or unsubstituted heterocycloalkylene (e.g. unsubstituted). $L^1$ may be 5 to 6 membered substituted or unsubstituted arylene (e.g. unsubstituted). $L^1$ may be 5 to 6 membered substituted or unsubstituted heteroarylene (e.g. unsubstituted).

In embodiments, the 5' terminus of the single-stranded nucleic acid sequence is attached to the first linker ($L^1$). In embodiments, as disclosed in more detail below, the 3' terminus of the single-stranded nucleic acid sequence is attached to the second linker ($L^2$). In embodiments, as disclosed in more detail below, the 5' terminus of the single-stranded nucleic acid sequence is attached to the second linker ($L^2$). In embodiments, the 3' terminus of the single-stranded nucleic acid sequence is attached to the first linker ($L^1$).

The single-stranded nucleic acid sequence provided herein includes a nuclease cleavage site. A "nuclease cleave site" as provided herein includes any site of a nucleic acid sequence recognized and cleaved by a nuclease. In embodiments, the nuclease cleavage site is a site of a single-stranded nucleic acid sequence (e.g., DNA or RNA) recognized and cleaved by a nuclease. Therefore, the nuclease cleavage site is formed by a nucleotide sequence recognized and cleaved by a nuclease. In embodiments, the nuclease cleavage site includes a cleavage point. A "cleavage point" as referred to herein, is a bond connecting two nucleotides of a nuclease cleavage site and hydrolyzed by a nuclease. In embodiments, the cleavage point is a bond connecting two deoxythymidine nucleotides. In embodiments, the cleavage point is a bond connecting a first deoxythymidine to a second deoxythymidine. In embodiments, the cleavage point is a bond connecting a first unmodified deoxythymidine to a second unmodified deoxythymidine. In embodiments, the nuclease is a bacterial nuclease. In embodiments, the nuclease is a gram negative bacterial nuclease. In embodiments, the nuclease is a staphylococcus micrococcal nuclease. In embodiments, the nuclease is *Acinetobacter baumannii* outer membrane protein A. In embodiments, the nuclease is Eap (extracellular adherence protein). In embodiments, the nuclease is bifunctional autolysin. In embodiments, the nuclease is protein A (membrane-bound). In embodiments, the nuclease is immunodominant staphylococcal antigen B.

The cleavage point may be closer to the 5' terminus of the single-stranded nucleic acid sequence than to the 3' terminus of the single-stranded nucleic acid sequence. Where the cleavage point is closer to the 5' terminus of the single-stranded nucleic acid sequence than to the 3' terminus, the number of nucleotides connecting the 5' terminus to the cleavage point is smaller than the number of nucleotides connecting the cleavage point to the 3' terminus. The nucleotides connecting the cleavage point to the 5' end of the single-stranded nucleic acid sequence are referred to herein as "5' nucleotides", while the nucleotides connecting the cleavage point to the 3' end of the single-stranded nucleic acid sequence are referred to herein as "3' nucleotides."

In embodiments, the single-stranded nucleic acid sequence includes a 5' nucleotide and a 3' nucleotide. In embodiments, the single-stranded nucleic acid sequence includes a plurality of 5' nucleotides and a plurality of 3' nucleotides. In embodiments, the single-stranded nucleic acid sequence includes from about 4 to about 40 5' nucleotides. In embodiments, the single-stranded nucleic acid sequence includes from about 4 to about 35 5' nucleotides. In embodiments, the single-stranded nucleic acid sequence includes from about 4 to about 30 5' nucleotides. In embodiments, the single-stranded nucleic acid sequence includes from about 4 to about 25 5' nucleotides. In embodiments, the single-stranded nucleic acid sequence includes from about 4 to about 20 5' nucleotides. In embodiments, the single-stranded nucleic acid sequence includes from about 4 to about 15 5' nucleotides. In embodiments, the single-stranded nucleic acid sequence includes from about 4 to about 10 5' nucleotides. In embodiments, the single-stranded nucleic acid sequence includes from about 4 to about 8 5' nucleotides. In embodiments, the single-stranded nucleic acid sequence includes from about 4 to about 7 5' nucleotides. In embodiments, the single-stranded nucleic acid sequence includes from about 4 to about 6 5' nucleotides. In embodiments, the single-stranded nucleic acid sequence includes about 5 5' nucleotides. In further embodiments, the single-stranded nucleic acid sequence includes about 6 3' nucleotides. Where the single-stranded nucleic acid sequence includes 5 5' nucleotides and 6 3' nucleotides, the single-stranded nucleic acid sequence is 11 nucleotides in length and the cleavage point is the bond connecting the fifth and the sixth nucleotide relative to the 5' end of the single-stranded nucleic acid sequence.

In embodiments, the single-stranded nucleic acid sequence includes from about 5 to about 40 5' nucleotides. In embodiments, the single-stranded nucleic acid sequence includes from about 5 to about 35 5' nucleotides. In embodiments, the single-stranded nucleic acid sequence includes from about 5 to about 30 5' nucleotides. In embodiments, the single-stranded nucleic acid sequence includes from about 5 to about 25 5' nucleotides. In embodiments, the single-stranded nucleic acid sequence includes from about 5 to about 20 5' nucleotides. In embodiments, the single-stranded nucleic acid sequence includes from about 5 to about 15 5' nucleotides. In embodiments, the single-stranded nucleic acid sequence includes from about 5 to about 10 5' nucleotides. In embodiments, the single-stranded nucleic acid sequence includes from about 5 to about 8 5' nucleotides. In embodiments, the single-stranded nucleic acid sequence includes from about 5 to about 7 5' nucleotides.

In embodiments, the single-stranded nucleic acid sequence includes from about 4 to about 48 3' nucleotides. In embodiments, the single-stranded nucleic acid sequence includes from about 4 to about 45 3' nucleotides. In embodiments, the single-stranded nucleic acid sequence includes from about 4 to about 40 3' nucleotides. In embodiments, the single-stranded nucleic acid sequence includes from about 4 to about 35 3' nucleotides. In embodiments, the single-stranded nucleic acid sequence includes from about 4 to about 30 3' nucleotides. In embodiments, the single-stranded nucleic acid sequence includes from about 4 to about 25 3' nucleotides. In embodiments, the single-stranded nucleic acid sequence includes from about 4 to about 20 3' nucleotides. In embodiments, the single-stranded nucleic acid sequence includes from about 4 to about 15 3' nucleotides. In embodiments, the single-stranded nucleic acid sequence includes from about 4 to about 10 3' nucleotides. In embodiments, the single-stranded nucleic acid sequence includes from about 4 to about 9 3' nucleotides. In embodiments, the single-stranded nucleic acid sequence includes from about 4 to about 8 3' nucleotides. In embodiments, the single-stranded nucleic acid sequence includes from about 4 to about 6 3' nucleotides. In embodiments, the single-stranded nucleic acid sequence includes about 6 3' nucleotides. In further embodiments, the single-stranded nucleic acid sequence includes about 5 5' nucleotides.

In embodiments the single-stranded nucleic acid sequence includes the sequence of SEQ ID NO:1 or fragment thereof at a length disclosed below. In embodiments, the single-stranded nucleic acid sequence is the sequence of SEQ ID NO:1. In embodiments, the single-stranded nucleic acid sequence is about 40 or less nucleotides in length. In embodiments, the single-stranded nucleic acid sequence is about 35 or less nucleotides in length. In embodiments, the single-stranded nucleic acid sequence is about 30 or less nucleotides in length. In embodiments, the single-stranded nucleic acid sequence is about 25 or less nucleotides in length. In embodiments, the single-stranded nucleic acid sequence is about 20 or less nucleotides in length. In embodiments, the single-stranded nucleic acid sequence is about 15 or less nucleotides in length. In embodiments, the single-stranded nucleic acid sequence is about 14 or less nucleotides in length. In embodiments, the single-stranded nucleic acid sequence is about 13 or less nucleotides in length. In embodiments, the single-stranded nucleic acid sequence is about 12 or less nucleotides in length. In embodiments, the single-stranded nucleic acid sequence is about 11 nucleotides in length. In embodiments, the single-stranded nucleic acid sequence is about 10 or less nucleotides in length. In embodiments, the single-stranded nucleic acid sequence is about 9 or less nucleotides in length. In embodiments, the single-stranded nucleic acid sequence is about 8 or less nucleotides in length. In embodiments, the single-stranded nucleic acid sequence is about 7 or less nucleotides in length. In embodiments, the single-stranded nucleic acid sequence is about 6 or less nucleotides in length. In embodiments, the single-stranded nucleic acid sequence is about 5 or less nucleotides in length. In embodiments, the single-stranded nucleic acid sequence is about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 nucleotides in length.

In embodiments, less than about 800 nucleic acid moieties are bonded to the nanoparticle core. In embodiments, less than about 750 nucleic acid moieties are bonded to the nanoparticle core. In embodiments, less than about 700 nucleic acid moieties are bonded to the nanoparticle core. In embodiments, less than about 650 nucleic acid moieties are bonded to the nanoparticle core. In embodiments, less than about 600 nucleic acid moieties are bonded to the nanoparticle core. In embodiments, less than about 550 nucleic acid moieties are bonded to the nanoparticle core. In embodiments, less than about 500 nucleic acid moieties are bonded to the nanoparticle core. In embodiments, less than about 450 nucleic acid moieties are bonded to the nanoparticle core. In embodiments, less than about 400 nucleic acid moieties are bonded to the nanoparticle core. In embodiments, less than about 350 nucleic acid moieties are bonded to the nanoparticle core. In embodiments, less than about 300 nucleic acid moieties are bonded to the nanoparticle core. In embodiments, from about 500 to about 600 nucleic acid moieties are bonded to the nanoparticle core. In embodiments, about 800, 750, 700, 650, 600, 550, 500, 450, 400, 350 or 300 nucleic acid moieties are bonded to the nanoparticle core.

In embodiments, the nucleic acid moiety includes a DNA. In embodiments, the nucleic acid moiety includes a RNA. In embodiments, the nucleic acid moiety is a DNA. In embodiments, the nucleic acid moiety is a RNA. In embodiments, the nucleic acid moiety includes a single-stranded DNA. In embodiments, the nucleic acid moiety includes a single-stranded RNA. In embodiments, the nucleic acid moiety is a single-stranded DNA. In embodiments, the nucleic acid moiety is a single-stranded RNA.

In embodiments, the single-stranded nucleic acid sequence includes a modified nucleotide. A "modified nucleotide" as referred to herein is a nucleotide including a chemical modification (e.g., methylation). Thus, in embodiments, the modified nucleotide is a 2'O-methylated nucleotide. In embodiments, the nuclease cleavage site includes an unmodified nucleotide. In embodiments, the unmodified nucleotide is a deoxythymidine.

In embodiments, the nuclease cleavage site is a bacterial nuclease cleavage site. In embodiments, the nuclease cleavage site is a micrococcal nuclease cleavage site.

In embodiments, each of the nucleic acid moieties further includes a water soluble moiety covalently attached to the single-stranded nucleic acid sequence through a second linker. Thus, in embodiments, each of the nucleic acid moieties consists essentially (e.g., consists of) a first linker binding the nucleic acid moiety to the nanoparticle core and a single-stranded nucleic acid sequence of about 50 or less nucleotides in length covalently attached to the first linker and a water soluble moiety covalently attached to the single-stranded nucleic acid sequence through a second linker. In embodiments, each of the nucleic acid moieties consists essentially (e.g., consists of) a first linker binding the nucleic acid moiety to the nanoparticle core and a single-stranded nucleic acid sequence of about 50 or less nucleotides in length covalently attached to the first linker and a water soluble moiety covalently attached to the single-stranded nucleic acid sequence through a second linker, if the nucleic acid moiety does not further include or is attached to anything than a first linker binding the nucleic acid moiety to the nanoparticle core and a single-stranded nucleic acid sequence of about 50 or less nucleotides in length covalently attached to the first linker and a water soluble moiety covalently attached to the single-stranded nucleic acid sequence through a second linker. In embodiments, each of the nucleic acid moieties consists essentially (e.g., consists of) a first linker binding the nucleic acid moiety to the nanoparticle core and a single-stranded nucleic acid sequence of about 50 or less nucleotides in length covalently attached to the first linker and a water soluble moiety covalently attached to the single-stranded nucleic acid sequence through a second linker, if the nucleic acid moiety is not further attached to or does not further include a biomolecule, a polypeptide moiety, a peptide moiety, a nucleic acid moiety, a carbohydrate moiety, an enzyme moiety, an oligosaccharide moiety, a polysaccharide moiety, a polymer moiety, a steroid moiety, a therapeutic moiety (e.g., drug, small molecule), a detectable moiety (e.g., a fluorescent moiety, luminescent moiety, colorimetric moiety, phosphorescent moiety, radioactive moiety or electroactive moiety), a pharmaceutically reactive moiety, a prodrug moiety, a conjugate chemistry reactive moiety, a contrast agent moiety (e.g., a magnetic resonance imaging (MRI) moiety, atomic force microscopy (AFM) moiety, transmission electron microscopy (TEM) moiety, Raman spectroscopy moiety, ultra-violet spectroscopy (UV-Vis) moiety, X-Ray diffraction moiety) or a cleavable moiety (e.g., an enzymatic cleavable moiety, a metal cleavable moiety, an acid cleavable moiety, a redox cleavable moiety, a photocleavable moiety, an electrically cleavable moiety.

In embodiments, the water soluble moiety is a water soluble polymer moiety. In embodiments, the water soluble polymer moiety is a biopolymer moiety, an alkylpolyamine moiety, an alkylpolyamide moiety, an alkylpolyether moiety, an alkylpolysulfonates moiety, a polyacrylamide moiety, a carbohydrate moiety or an alkylpolyalcohol moiety. In embodiments, the alkylpolyether moiety is a PEG moiety. The water soluble moiety is connected to the single-stranded nucleic acid sequence through a second linker. In embodiments the single-stranded nucleic acid sequence is bonded to the nanoparticle core through a first linker and to the water soluble moiety through a second linker. Thus, in embodiments, the single-stranded nucleic sequence connects the first linker to the second linker. In embodiments, the 5' terminus of the single-stranded nucleic acid sequence is bound to the first linker and the 3' terminus of the single-stranded nucleic acid sequence is bound to the second linker. In embodiments, the 3' terminus of the single-stranded nucleic acid sequence is bound to the first linker and the 5' terminus of the single-stranded nucleic acid sequence is bound to the second linker.

In embodiments, the nucleic acid moiety has the formula:

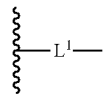

single-stranded nucleic acid sequence -$L^2$- water soluble moiety

The second linker or $L^2$ may be a chemical linker that connects the single-stranded nucleic acid sequence to the water soluble moiety. In embodiments, $L^2$ is a divalent linker formed by reacting a functional (reactive) group attached to the single-stranded nucleic acid sequence with the water soluble moiety (e.g. a functional (reactive) group of the water soluble moiety). $L^2$ may be a bond, —S—, —OSi(OR$^{5A}$)(OR$^{6A}$)(O)—, or —OP(O)(OR$^{7A}$)(O)—. $R^{5A}$, $R^{6A}$, and $R^{7A}$ are independently hydrogen, substituted or unsubstituted alkyl (e.g. $C_1$-$C_5$), substituted or unsubstituted heteroalkyl (2 to 5 membered heteroalkyl), substituted or unsubstituted cycloalkyl (3 to 6 membered cycloalkyl), substituted or unsubstituted heterocycloalkyl (2 to 6 membered heterocycloalkyl), substituted or unsubstituted aryl (2 to 6 membered aryl), or substituted or unsubstituted heteroaryl (2 to 6 membered heteroaryl). $R^{5A}$, $R^{6A}$, and $R^{7A}$ may independently be hydrogen, substituted or unsubstituted alkyl (e.g. $C_1$-$C_5$). $R^{5A}$, $R^{6A}$, and $R^{7A}$ are independently hydrogen or unsubstituted alkyl (e.g. $C_1$-$C_5$).

$L^2$ may be $C_1$-$C_5$ substituted or unsubstituted alkylene (e.g. unsubstituted). $L^2$ may be 3 to 7 membered substituted or unsubstituted heteroalkylene (e.g. unsubstituted). $L^2$ may be 5 to 6 membered substituted or unsubstituted cycloalkylene (e.g. unsubstituted). $L^2$ may be 5 to 6 membered substituted or unsubstituted heterocycloalkylene (e.g. unsubstituted). $L^2$ may be 5 to 6 membered substituted or unsubstituted arylene (e.g. unsubstituted). $L^2$ may be 5 to 6 membered substituted or unsubstituted heteroarylene (e.g. unsubstituted).

In embodiments, $L^2$ is a bond, —C(O)—, —C(O)O—, —O—, —S—, —NH—, —NR$^{1A}$—, —C(O)NR$^{2A}$—, —S(O)$_{n.1}$—, —S(O)NR$^{3A}$—, —OP(O)(OR$^{4A}$)O—, substituted or unsubstituted alkylene (e.g. $C_1$-$C_{10}$), substituted or unsubstituted heteroalkylene (e.g. 2 to 10 heteroalkylene), substituted or unsubstituted cycloalkylene (e.g. 3 to 8 membered cycloalkylene), substituted or unsubstituted heterocycloalkylene (e.g. 3 to 8 membered heterocycloalkylene), substituted or unsubstituted arylene (e.g. 3 to 8 membered arylene), or substituted or unsubstituted heteroarylene (e.g. 3 to 8 membered heteroarylene), an amino acid sequence linker, or a nucleic acid sequence linker. $R^{1A}$, $R^{2A}$, $R^{3A}$ and $R^{4A}$, are independently hydrogen, halogen, —$N_3$, —$NO_2$, —$CF_3$, —$CCl_3$, —$CBr_3$, —$Cl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$OCH_3$, —$NHCNHNH_2$, substituted or unsubstituted alkyl (e.g. $C_1$-$C_{10}$), substituted or unsubstituted heteroalkyl (e.g. 2 to 10 heteroalkyl), substituted or unsubstituted cycloalkyl (e.g. 3 to 8 membered cycloalkyl), substituted or unsubstituted heterocycloalkyl (e.g. 3 to 8 membered heterocycloalkyl), substituted or unsubstituted aryl (e.g. 3 to 8 membered aryl), or substituted or unsubstituted heteroaryl (e.g. 3 to 8 membered heteroaryl). The symbol n.1 is independently 1 or 2.

The compositions provided herein include a plurality of functionalized nanoparticles as described herein. Thus, in one aspect, a plurality of functionalized nanoparticles is provided and each functionalized nanoparticle is a functionalized nanoparticle as provided herein including embodiments thereof. In embodiments, the nanoparticles are in a vessel. In embodiments, the vessel is in a spectrophotometry device. The plurality of functionalized nanoparticles may be supplied as an aqueous suspension or as a powder within the vessel. The vessel may be a storage device or other readily usable container capable of storing and protecting the functionalized nanoparticles contained within.

III. METHODS OF USE

The methods provided herein are, inter alia, useful for forming nanoparticle aggregates and for the detection of nuclease activity. The nucleic acid moiety of the functionalized nanoparticle provided herein includes a nuclease cleavage site. In the presence of a nuclease the cleavage site is cleaved, thereby forming a cleaved functionalized nanoparticle. A cleaved functionalized nanoparticle as provided herein has an increased ability to interact (aggregate) with other cleaved functionalized nanoparticles relative to a functionalized nanoparticle wherein the cleavage site is intact. The electrostatic repulsion of a cleaved functionalized nanoparticle may be decreased compared to a functionalized nanoparticle wherein the cleavage site is intact. A decreased electrostatic repulsion enables the cleaved functionalized nanoparticle to interact (aggregate) with other cleaved functionalized nanoparticles thereby forming aggregates. Thus, a nanoparticle aggregate as described herein includes a plurality of cleaved functionalized nanoparticles as provided herein, wherein the plurality of cleaved functionalized nanoparticles are bound together. The plurality of cleaved functionalized nanoparticles may be bound by non-covalent bond (e.g. electrostatic interactions (e.g. ionic bond, hydrogen bond, halogen bond), van der Waals interactions (e.g.

dipole-dipole, dipole-induced dipole, London dispersion), ring stacking (pi effects), hydrophobic interactions and the like.

In one aspect, a method of forming a nanoparticle aggregate is provided. The method includes (i) contacting a nuclease with the plurality of functionalized nanoparticles as provided herein including embodiments thereof. (ii) The nuclease is allowed to cleave the single-stranded nucleic acid sequence at the nuclease cleavage site of the plurality of functionalized nanoparticles, thereby forming a plurality of cleaved nanoparticles. (iii) The plurality of cleaved nanoparticles are allowed to bind to each other, thereby forming a nanoparticle aggregate.

In one aspect, a method of forming a nanoparticle aggregate is provided. The method includes (i) contacting a nuclease with the plurality of functionalized nanoparticles provided herein including embodiments thereof. (ii) The nuclease is allowed to cleave the single-stranded nucleic acid sequence at the nuclease cleavage site of the plurality of functionalized nanoparticles, thereby forming a nanoparticle aggregate. In embodiments, the nuclease cleaves the single-stranded nucleic acid sequence at the cleavage point. In embodiments, the nanoparticle aggregate is formed in vitro. In embodiments, the nanoparticle aggregate is formed in vivo. In embodiments, the nuclease is derived from a biological sample. In embodiments, the nuclease is derived from a human subject. In embodiments, the nuclease is derived from a bodily fluid. In embodiments, the nuclease is derived from a food sample. In embodiments, the nuclease is derived from a water sample (e.g., ground water, seawater). A water sample may be a sample derived from seawater, fresh water from an aquifer, ground water, a river or a lake. In embodiments, the sample is derived from seawater. In embodiments, the sample is derived from fresh water from an aquifer. In embodiments, the sample is derived from ground water. In embodiments, the sample is derived from a river. In embodiments, the sample is derived from a lake. In embodiments, the method includes detecting the nanoparticle aggregate. In embodiments, the detecting includes colorimetric detection of the nanoparticle aggregate. In embodiments, the allowing of step (ii) includes forming a plurality of cleaved functionalized nanoparticles including a cleaved single-stranded nucleic acid sequence. In embodiments, the cleaved single-stranded nucleic acid sequence is less than about 20 nucleotides in length. In embodiments, the cleaved single-stranded nucleic acid sequence is less than about 10 nucleotides in length. In embodiments, the cleaved single-stranded nucleic acid sequence is about 5 nucleotides in length.

In one aspect, a method of detecting a nuclease activity in a sample is provided. The method includes contacting a sample with a functionalized nanoparticle provided herein including embodiments thereof, thereby detecting the nuclease activity. In embodiments, the sample is a water sample. In embodiments, the water sample is a ground water sample. In embodiments, the sample is a water sample. In embodiments, the water sample is a creek water sample. Where the water sample is a creek water sample, the water sample is derived from a creek. In embodiments, the method includes contacting the sample with a plurality of functionalized nanoparticles, wherein each functionalized nanoparticle is a functionalized nanoparticle provided herein including embodiments thereof.

IV. EXAMPLES

Example 1

Colorimetric Detection of *Staphylococcus aureus* Contaminated Solutions Without Purification Recreational waters, such as lakes, rivers, and beaches, are common sources of *Staphylococcus aureus* (*S. aureus*), which can cause life-threatening infections.[1-4] Definitive detection of *S. aureus* in water samples using growth-based methods, such as chromogenic agars, can take as long as 72 hours. This presents a potential public hazard due to the delay in sample processing.[5,6] There is thus a need for novel methods to rapidly and selectively detect *S. aureus*. A variety of colorimetric assays have been explored, including ELISA and oligonucleotide-embedded agar matrices to detect the presence and activity of micrococcal nuclease (MN), which is specifically expressed by *S. aureus*.[7,8] Other in vitro methods include PCR to amplify *S. aureus* specific genes in serum samples and using labeled bacteriophage that infect *S. aureus*.[9,10] However, all of these methods require either culturing, which is time consuming and dependent on a laboratory infrastructure, or sophisticated instrumentation. Due to this, there is a pressing need for a portable, simple point-of-care diagnostic for *S. aureus*. Applicants have previously developed a chemically modified fluorescent probe that selectively detects micrococcal nuclease and is resistant to many other nucleases, including serum nucleases.[11] Here, Applicants sought to develop a simple in vitro assay with this oligonucleotide probe as a foundation. While Applicants previously used a fluorescence readout for non-invasive imaging applications, Applicants favored a colorimetric readout for in vitro applications because colorimetric assays do not require instrumentation and can therefore be implemented in a wider variety of settings, including remote locations. Applicants demonstrate that oligonucleotide-functionalized gold nanoparticles (Oligo-AuNPs) can be used to rapidly and selectively detect *S. aureus* simply through a change in color. The particles can be stored as a lyophilized powder and reconstituted at time of use. This approach requires minimal sample preparation and no extraneous instrumentation. This rapid and simple diagnostic read-out could be used in field tests to monitor food and water sources.

The oligonucleotide probe has been previously reported for the species specific detection of *S. aureus* consists of nine 2'-O-methylated chemically modified nucleotides with an unmodified pair of deoxythymidines in the center of the sequence and a fluorophore and quencher on either ends. The chemical modifications render it resistant to mammalian serum nucleases. In the presence of MN, the oligonucleotide strand is cleaved, presumably between the unmodified deoxythymidines, producing a fluorescent signal.[11] This probe has also been applied to analyze patient plasma samples.[12]

Using a fluorescent probe enabled non-invasive imaging of *S. aureus* infections via localized probe activation. For many in vitro applications, an ideal assay for *S. aureus* would avoid the need for instruments that measure fluorescence. Applicants hypothesized that the same oligonucleotide sequence used for non-invasive imaging could be used to functionalize gold nanoparticles such that when it was cleaved by MN, the Oligo-AuNPs would aggregate and undergo a color change from red to purple (FIG. 1A). The result would then be a highly sensitive colorimetric assay selective for S. aureus provided by this chemically modified oligonucleotide.

Oligo-AuNPs have been used extensively as colorimetric biosensors.[13,14] AuNPs have a surface plasmon resonance that is influenced by size, geometry, ligand and proximity to other nanoparticles. Due to this, nanoparticle aggregation results in a shift in SPR related absorption (~520 nm to ~650 nm) causing a colorimetric change in solution from red to purple.[14,15] The color change seen in solution during the aggregation of AuNPs provides the basis for a practical platform for biosensing. The assembly/aggregation or disassembly/anti-aggregation of Oligo-AuNPs can be induced by proteins, DNA sequences, small molecules, or metal ions.[16-23] Of particular relevance, DNase I, a human endonuclease, has been detected via its cleavage of oligonucleotides on AuNPs.[18,21] AuNPs have been used to detect staph bacteria by direct coating of the intact bacteria mediated by antibodies[24], aptamers[25], hybridization of PCR-amplified S. aureus DNA[26], or phenylboronic acid[27], and AuNPs have been used to transform PCR detection of staph bacteria into a colorimetric method.[28] Moreover, in the context of selective bacterial strain detection, Oligo-AuNPs have only been used to detect specific, purified DNA sequences.[29] There is no current system for direct colorimetric detection of specific S. aureus contamination in unpurified water samples. In this setting, it is likely that due to sample collection many samples will contain low numbers or no S. aureus bacteria themselves and detection will require sensitivity to S. aureus byproducts present. Applicants thought it would be possible to develop such a system based on the specificity of cleavage previously observed for their oligonucleotide probe. Applicants found that AuNPs functionalized with their probe sequence aggregated when exposed to MN and exhibited a comparable limit of detection as the fluorescent probe. This is noteworthy in the context of colorimetric detection as this is one of the shortest DNA coatings shown to control the aggregation state of gold nanoparticles. Applicants show that detection occurs via cleavage between the unmodified deoxythymidines when MN is used at low concentrations, however, multiple sites of the 11-mer oligonucleotide are cleaved at high concentrations of MN. When stabilized with trehalose, the Oligo-AuNPs could be stored as a lyophilized powder and reconstituted to achieve the initial limit of detection for MN. Finally, these Oligo-AuNPs were used for the selective detection of S. aureus versus three other bacterial species. Using readily obtained solution samples, this new platform is able to provide a rapid, visually-definitive result that requires no extraneous instrumentation. This has the potential to expedite S. aureus detection for a variety of food and water testing applications, including those in remote locations.

Results

The Oligo-AuNPs were prepared according to a protocol previously reported by Mirkin and coworkers.[30] Applicants' 11-mer oligonucleotide sequence was synthesized bearing a protected thiol on the 5' end. For particle preparation, the oligonucleotide was reduced and then added to the 20 nm AuNPs in a 5,000-fold excess. Following salt-aging to achieve maximal oligonucleotide functionalization on the surface, the particles were then purified by centrifugation. The Oligo-AuNPs were well dispersed, with an average size of 33 nm and had a zeta potential of −20.65 (Table 1). An established DTT displacement protocol was used to determine that each AuNP was functionalized with an average of 877 strands of DNA.[31]

TABLE 1

Oligo-AuNPs were characterized by DLS, Zeta Potential, and DTT Displacement (quantified number of oligonucleotide strands per particle). Particles were determined to be stable, monodisperse, and negatively charged. Characterization of Oligo-AuNPs

| | |
|---|---|
| DLS (avg) | 33.3 ± 0.753 nm |
| PDI (avg) | 0.049 ± 0.006 |
| Zeta Potential | −20.65 ± 2.375 |
| Oligo/AuNP | 876.5 ± 60 strands |

Figure 6A:
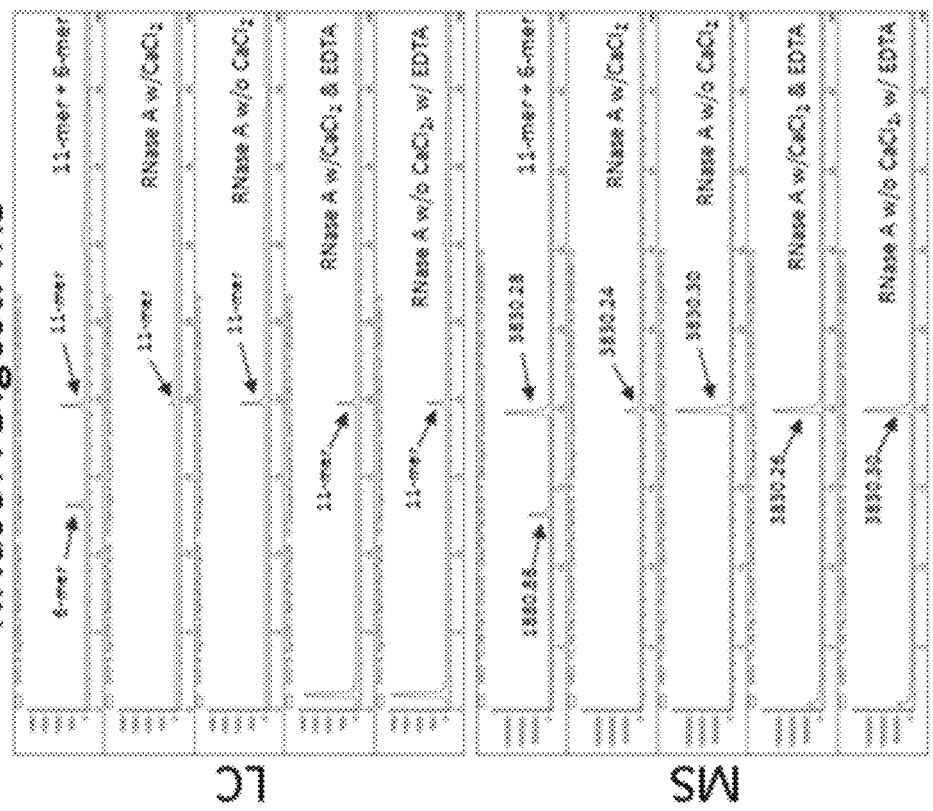
FIGS. 6A-6B.
Figure 6B:
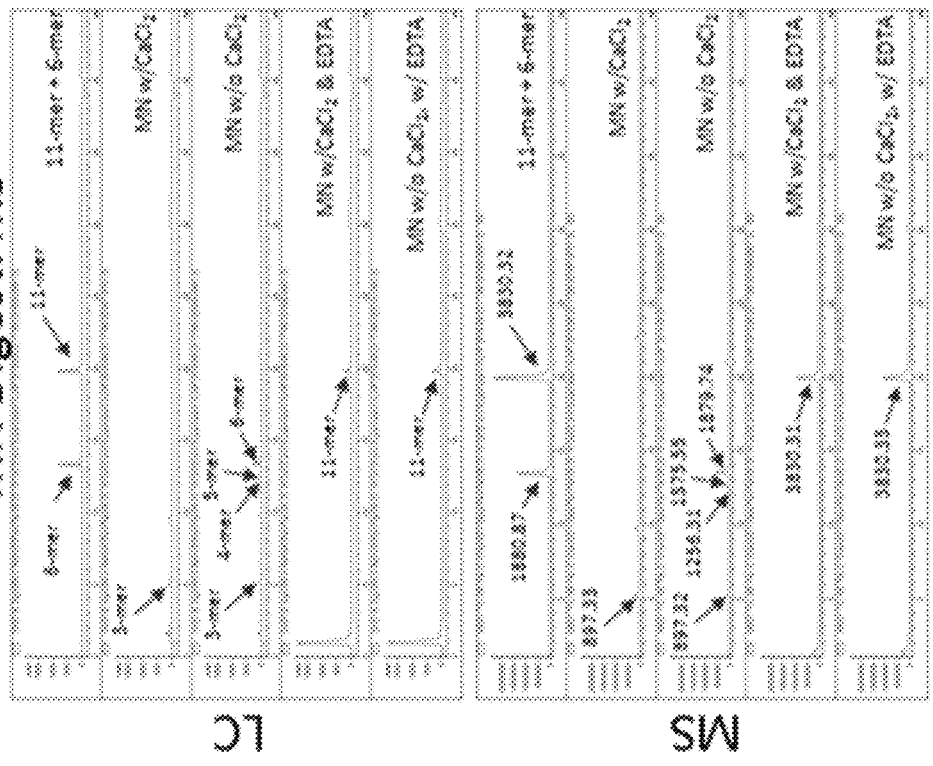
Figure 7:
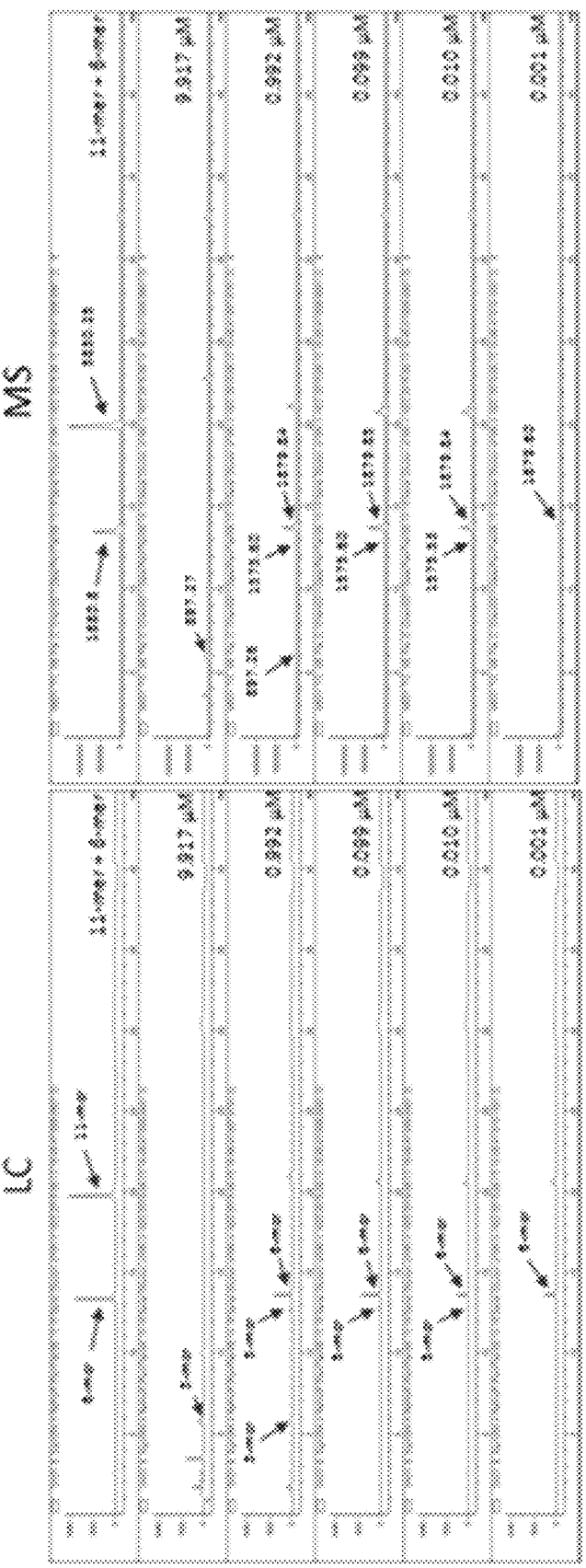
FIG. 7. MN was serially diluted and used to digest the 11-mer oligonucleotide (400 pmoles). At the highest concentration used, MN cleaved multiple sites within the 11-mer. However, from 0.992 µM to 0.001 µM MN, the primary cleavage site was between the unmodified deoxythymidines.

Prior to experimenting with the Oligo-AuNPs, Applicants validated the behavior of the oligonucleotide probe to ensure that removing the fluorophore and quencher did not affect its function. It is known that MN requires a salt co-factor to function[32,33], so Applicants evaluated the cleavage of the 11-mer oligonucleotide under three conditions: background levels of salt, high levels of salt via the addition of $CaCl_2$ and no salt via the addition of EDTA to scavenge metal ions. Using LC-MS, Applicants found that in the high salt condition with exogenous $CaCl_2$ the MN (9.917 µM) was highly promiscuous and cleaved the 11-mer oligonucleotide at multiple sites, while in the background salt condition, it appeared that cleavage was site specific as the 6-mer oligonucleotide was detected indicating cleavage between the deoxythymidines (FIG. 6A). Applicants found that the activity of MN in the high salt conditions could be returned to selective cleavage through sufficient dilution (0.992 µM, FIG. 7). The addition of EDTA completely suppressed cleavage of the 11-mer at all concentrations of MN. RNase A was chosen to test cleavage of the oligonucleotide because it is part of a superfamily of RNases that exists in all organisms and within most environments, with the primary environmental source being bacteria and fungi).[28,34,35] When RNase A (0.126 µM) was added to the 11-mer oligonucleotide, it remained intact and no digestion was observed (FIG. 6B).

TABLE 2

The digested oligonucleotides and their sequences are listed along with their molecular weights for LC-MS analysis.

| Oligonucleotide | Sequence | Molecular Weight (g/mol) |
|---|---|---|
| 11-mer | mCmUmCmG-T-T-mCmGmUmUmC (SEQ ID NO: 1) | 3830.7 |
| HS-5-mer (remains on particle after cleavage) | mCmUmCmG-T | 1888.5 |
| 6-mer (cleaved off sequence) | T-mCmGmUmUmC | 1880.3 |
| 5-mer (cleaved off sequence) | mCmGmUmUmC | 1576.1 |
| 4-mer (cleaved off sequence) | mGmUmUmC | 1256.9 |
| 3-mer (cleaved off sequence | mUmUmC | 897.6 |
| 2-mer (cleaved off sequence | mUmC | 577.4 |

Figure 1B:
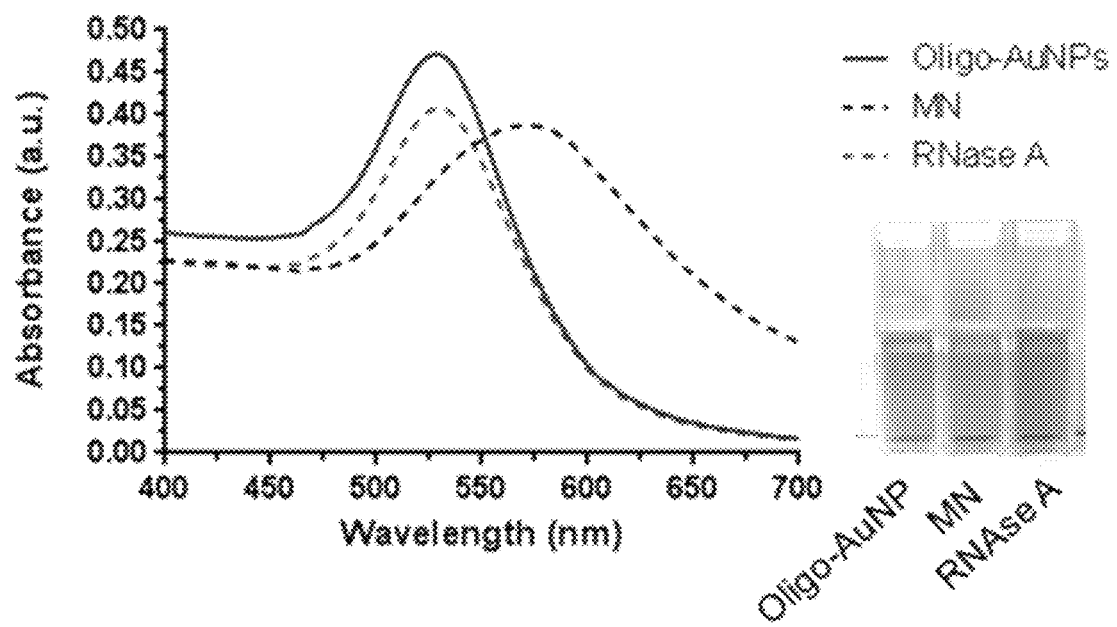

After demonstrating that the 11-mer was cleaved by MN, the aqueous solution of Oligo-AuNPs was treated with 0.05 µM MN or RNase A and 2 mM $CaCl_2$ (FIG. 1B). The Oligo-AuNP solution was then incubated at 37° C. in a water bath. After 5 minutes, the MN-treated Oligo-AuNPs experienced a color change from red to purple in solution as well as a shift in $\lambda_{max}$ from 530 nm to 570 nm. The RNase A condition did not result in a color change and the $\lambda_{max}$ remained at 530 nm.

Figure 2A:
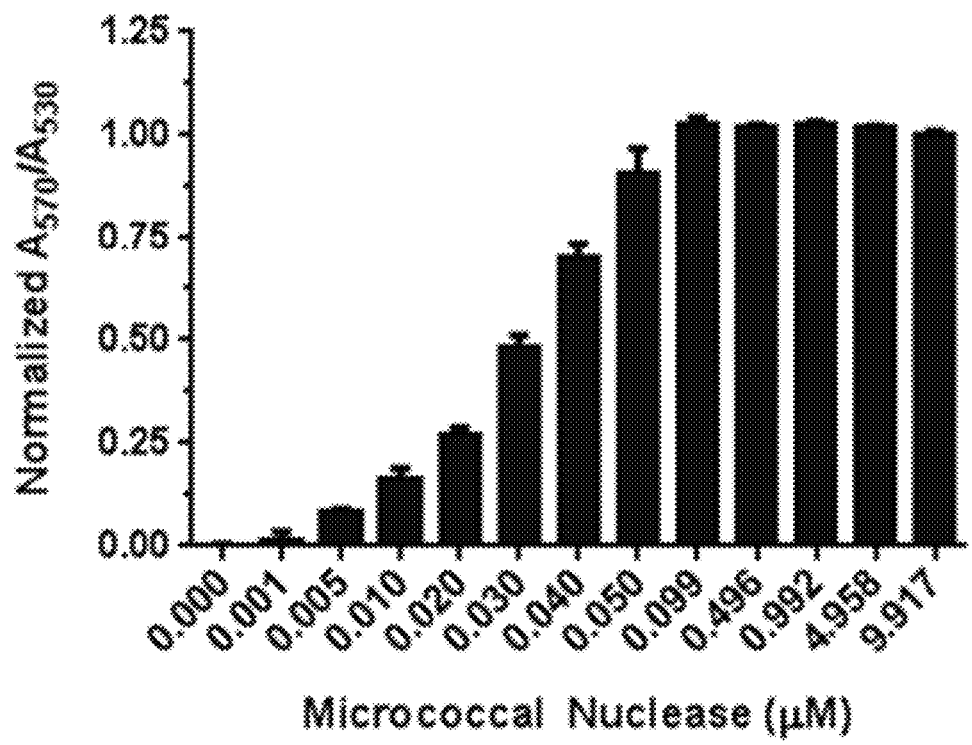
FIGS. 2A-2F. Specificity of Oligo-AuNPs to Micrococcal Nuclease.
Figure 2B:
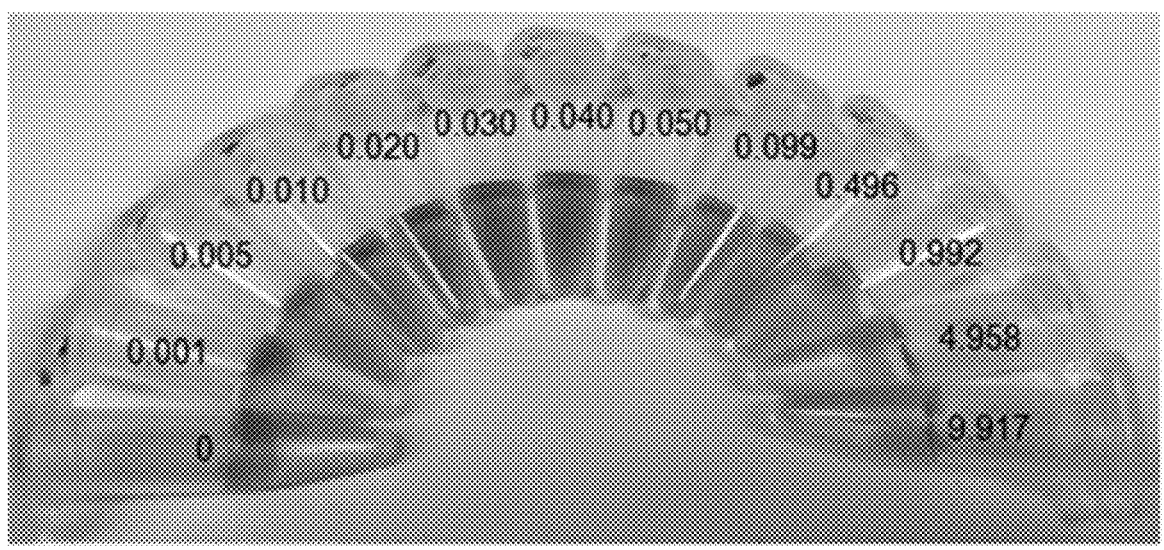
Figure 8:
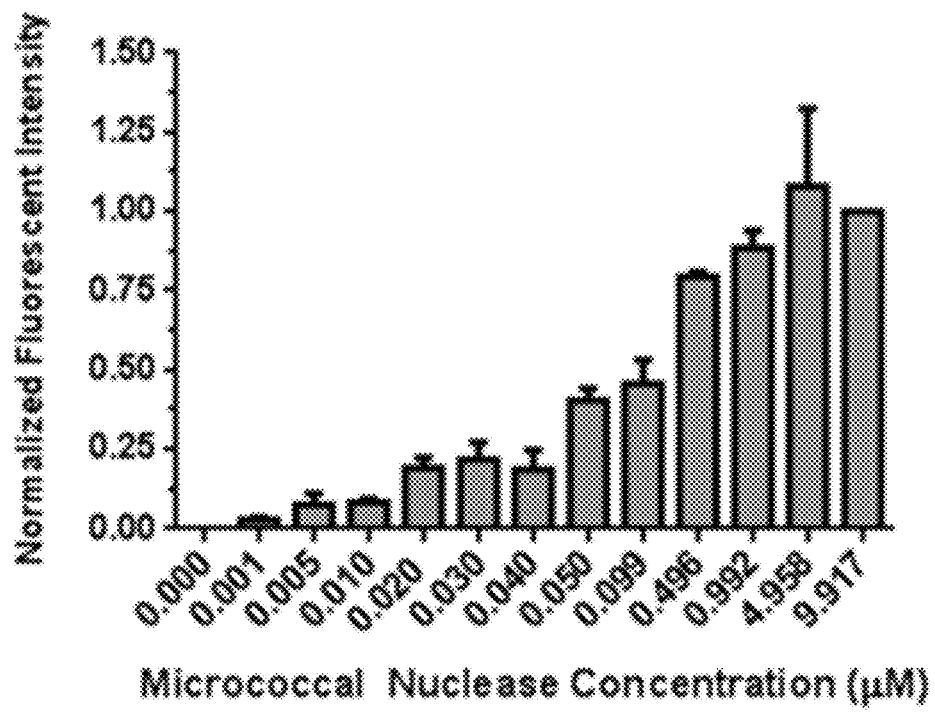
FIG. 8. The limit of detection of the fluorescent probe was determined to be 0.496 µM MN.
Figure 11:
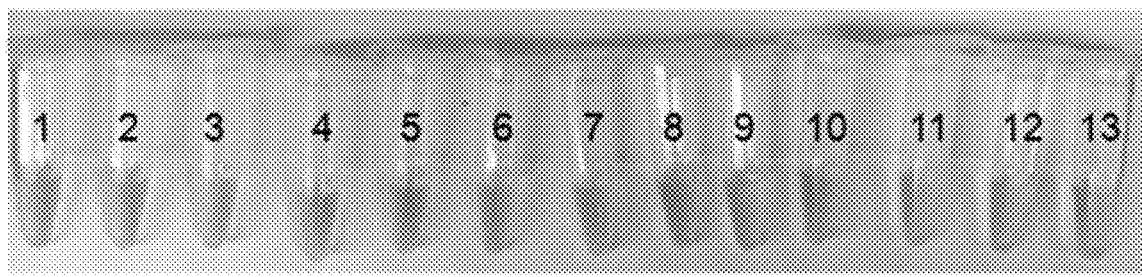
FIG. 11. 11-mer Oligo-AuNPs were treated with varying concentrations of MN and the tubes were scrambled. Participants were able to sort and differentiate between aggregated and non-aggregated samples.
Figure 11:
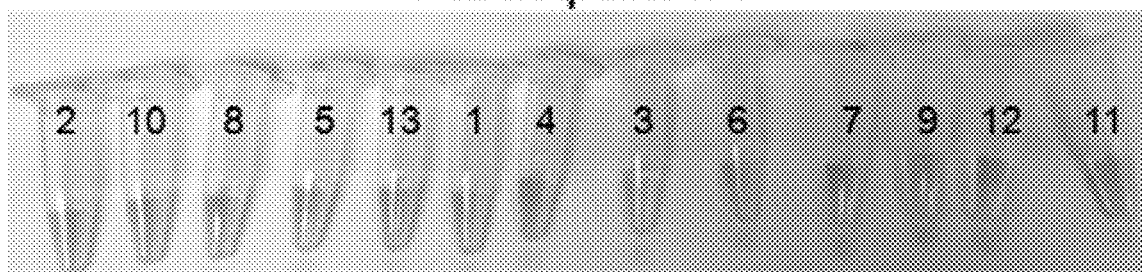
Figure 11:
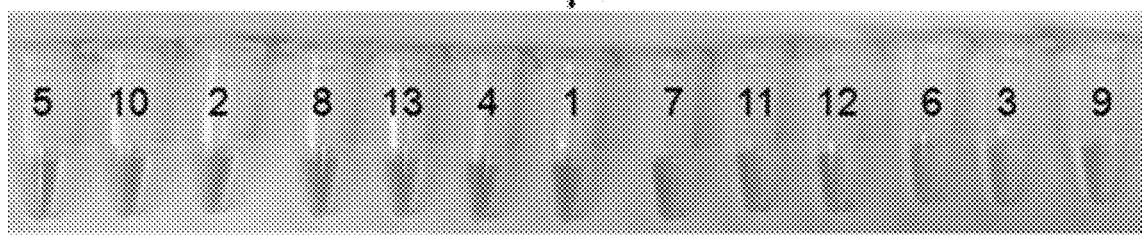
Figure 11:
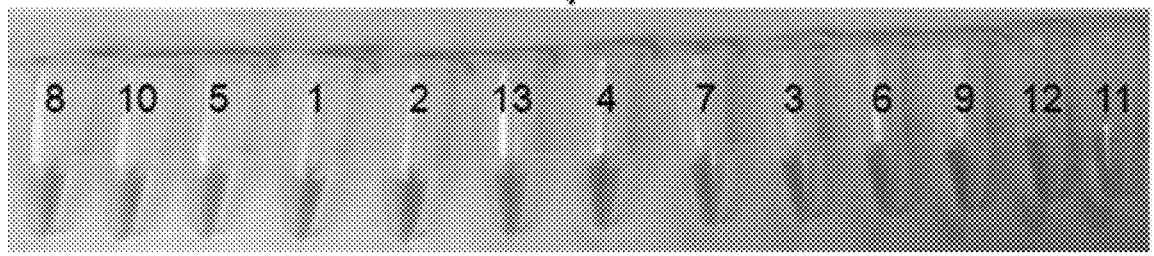

Having demonstrated colorimetric detection of MN using Oligo-AuNPs, Applicants sought to determine the limit of detection of the system in order to enable comparison to the fluorescent probe. Cleavage was measured as the ratio of the UV signal at 570 nm to 530 nm. In order to definitely determine limit of detection of the Oligo-AuNPs to MN, the UV absorbance curve needed to shift to at least 550 nm, the ratio of the UV signal 570 nm to 530 nm needed to be greater 0.5, and there needed to be a visible colorimetric change in solution. The sensitivity of the Oligo-AuNPs (0.5 nM) was determined to have a limit of detection of 0.04 µM MN (FIGS. 2A and 2B), whereas the RNase A limit of detection was 4.958 µM (FIGS. 2E and 2F). This suggests that the Oligo-AuNPs were sensitive to MN since less of it was needed to cause aggregation, whereas a greater amount of RNase A was needed in order for aggregation to occur. The fluorescent probe had a limit of detection of 0.496 µM (FIG. 8). It is rather remarkable that under these conditions the colorimetric sensor has a higher sensitivity than the fluorescent probe. Applicants hypothesize this is due to the fact that only a small number of oligonucleotides on each particle need to be cleaved to induce aggregation. To test the general utility of colorimetric detection with the Oligo-AuNPs, Applicants conducted a blind study where participants were presented with vials of Oligo-AuNPs treated with 13 different concentrations of MN and asked to sort the samples (FIG. 11, Table 2). In all 3 cases, participants grouped all samples below the limit of detection separately from all samples above the limit of detection, confirming that non-expert users could easily detect the color change.

TABLE 3

Listing of the thirteen different MN concentrations and the corresponding tube numbers used for the blind study testing the limit of detection (see also FIG. 11).

| Tube # | Concentration (µM) |
|---|---|
| 1 | 0.040 |
| 2 | 0.005 |
| 3 | 4.958 |
| 4 | 0.030 |
| 5 | 0.001 |
| 6 | 0.992 |
| 7 | 0.050 |
| 8 | 0 |
| 9 | 9.917 |
| 10 | 0.010 |
| 11 | 0.099 |
| 12 | 0.496 |
| 13 | 0.020 |

Figure 9A:
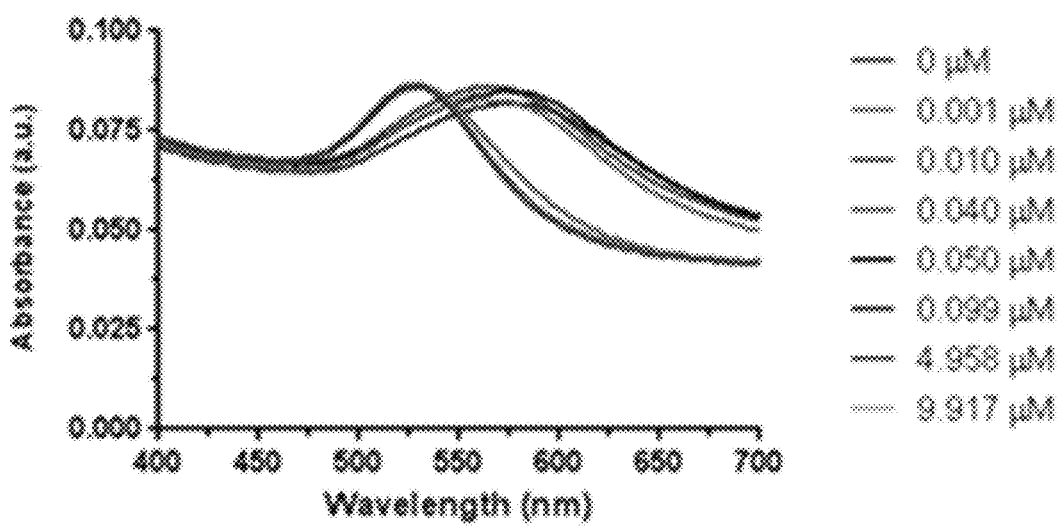
FIGS. 9A-9F.
Figure 9B:
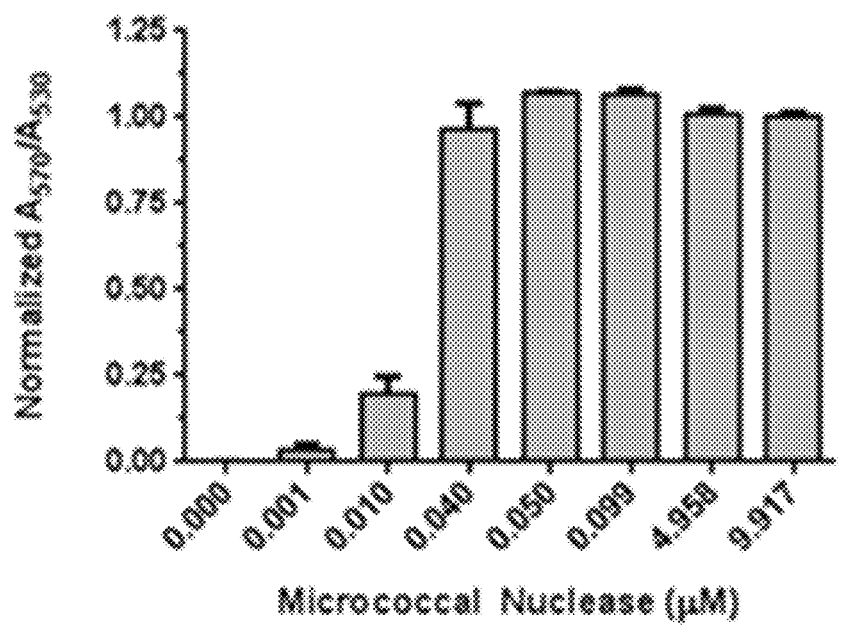
Figure 9C:
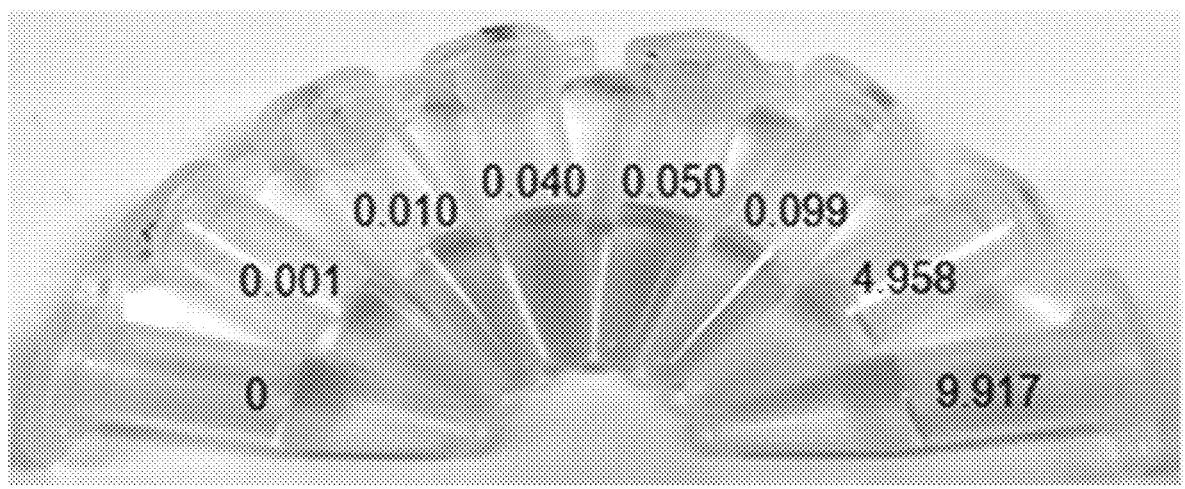
Figure 9D:
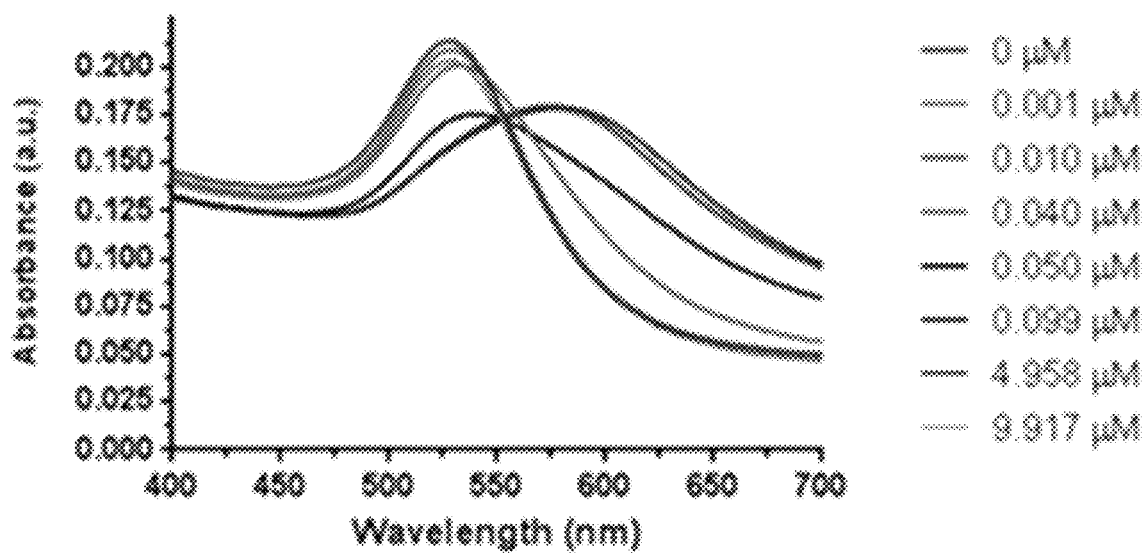
Figure 9E:
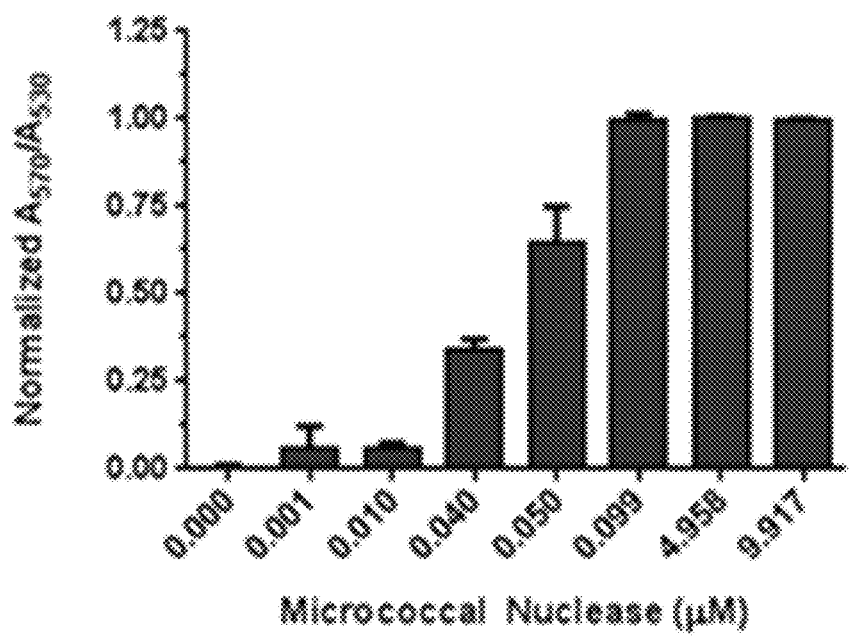
Figure 9F:
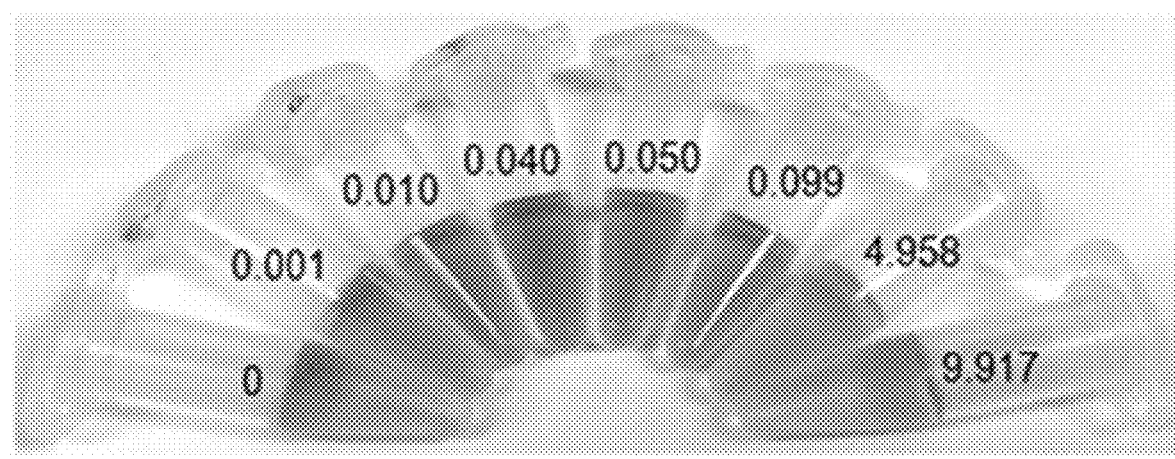
Figure 10A:
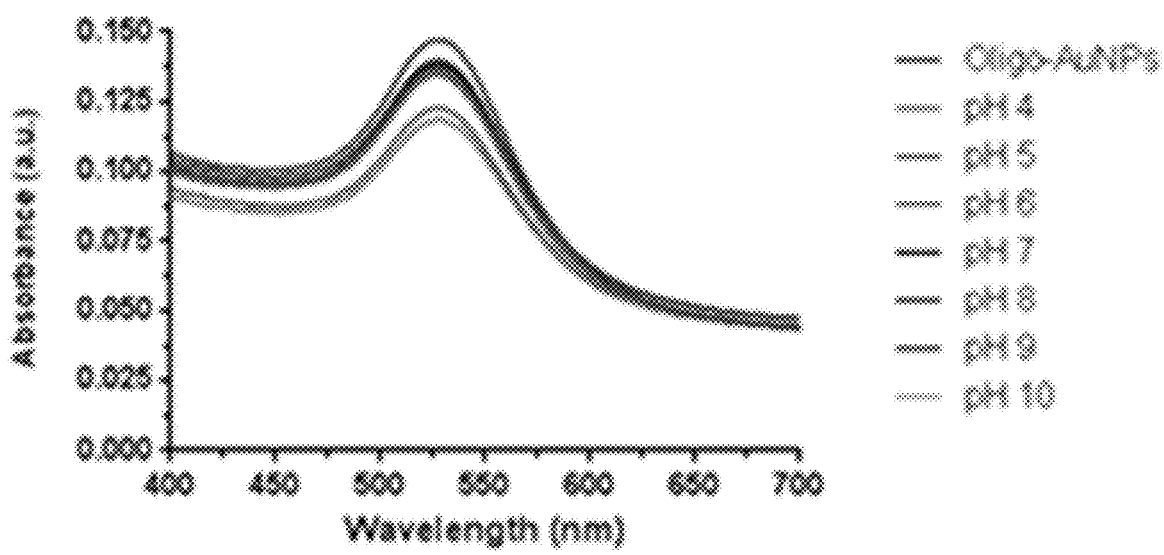
FIGS. 10A-10I.
Figure 10B:
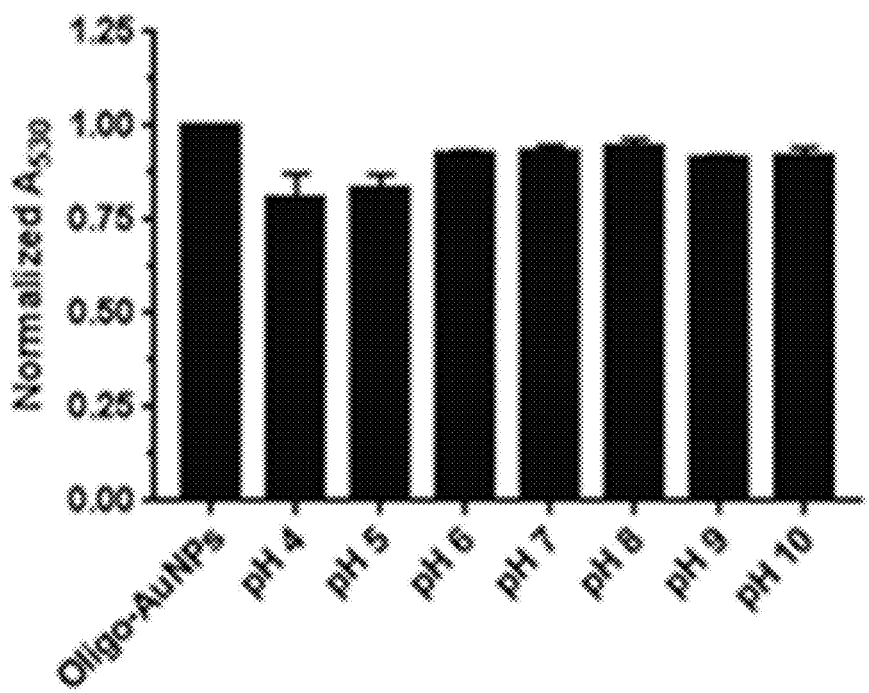
Figure 10C:
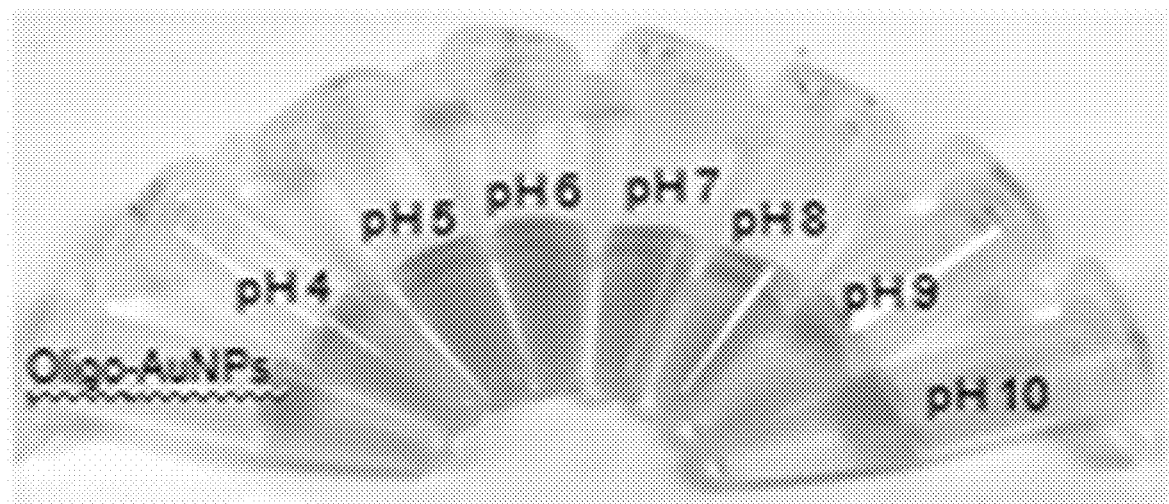
Figure 10D:
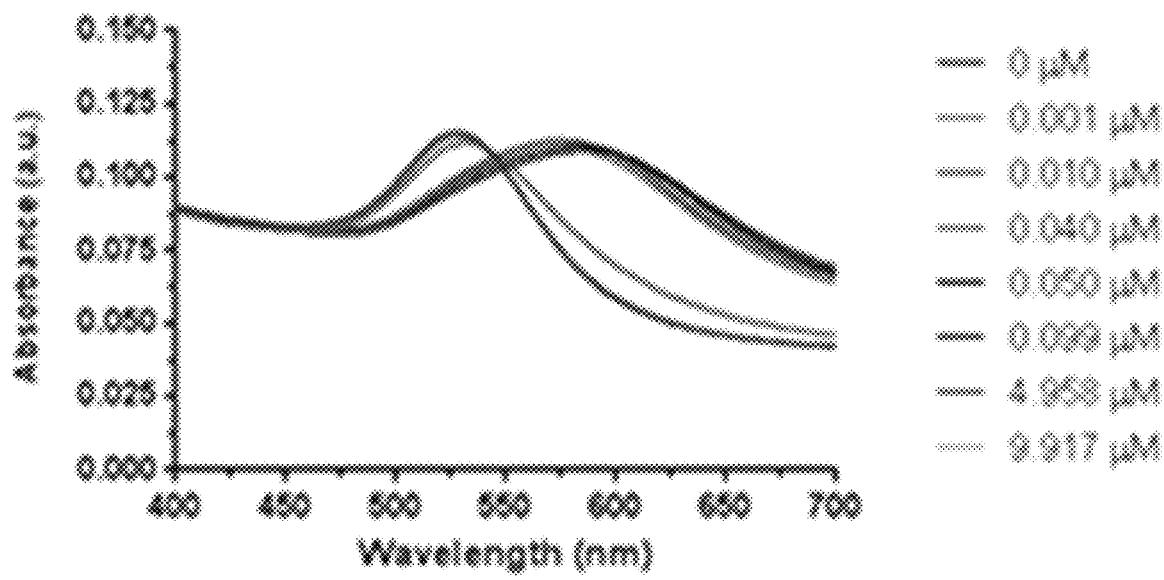
Figure 10E:
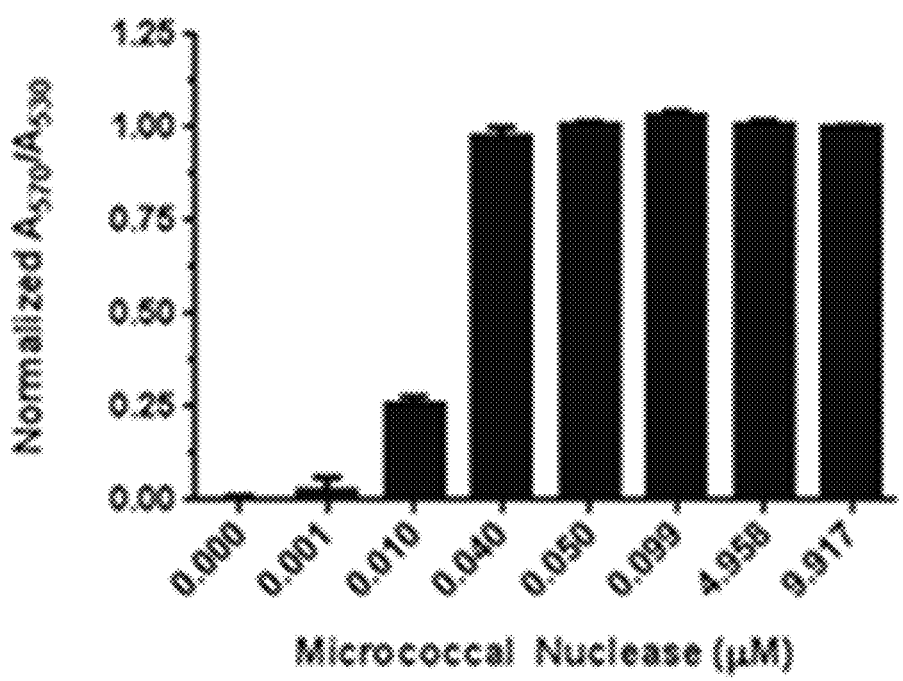
Figure 10F:
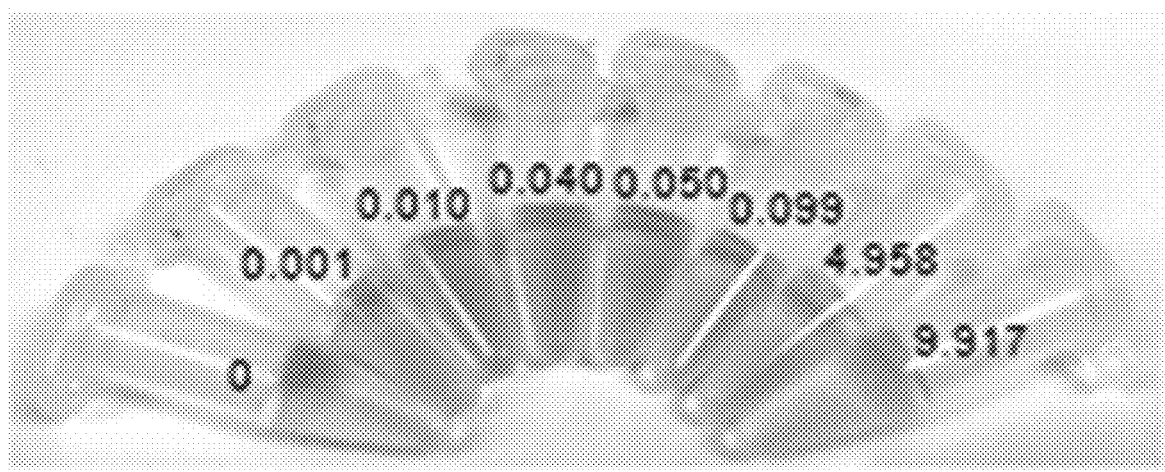
Figure 10G:
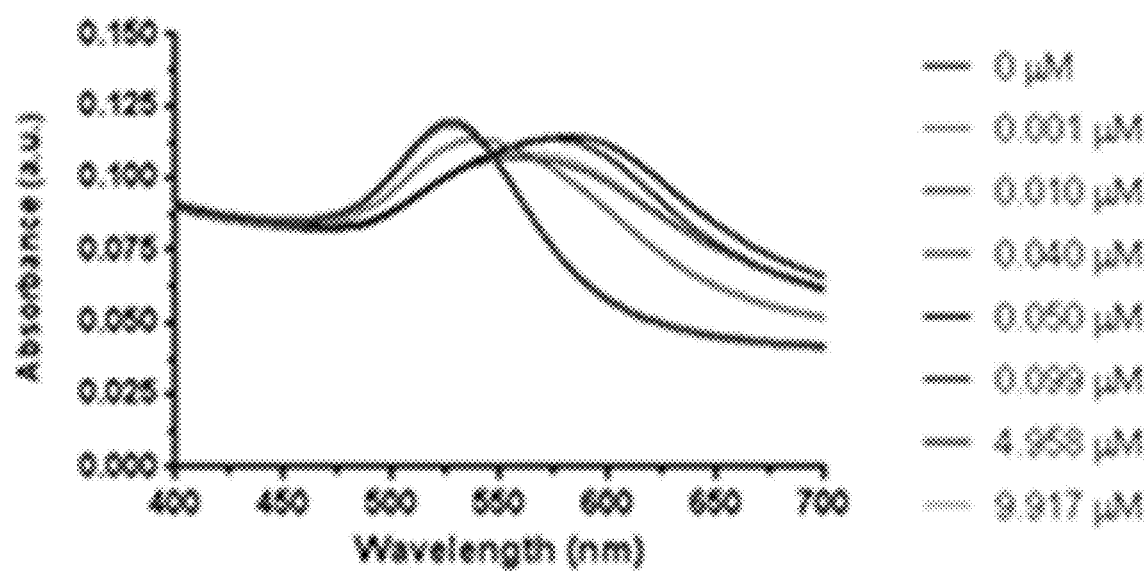
Figure 10H:
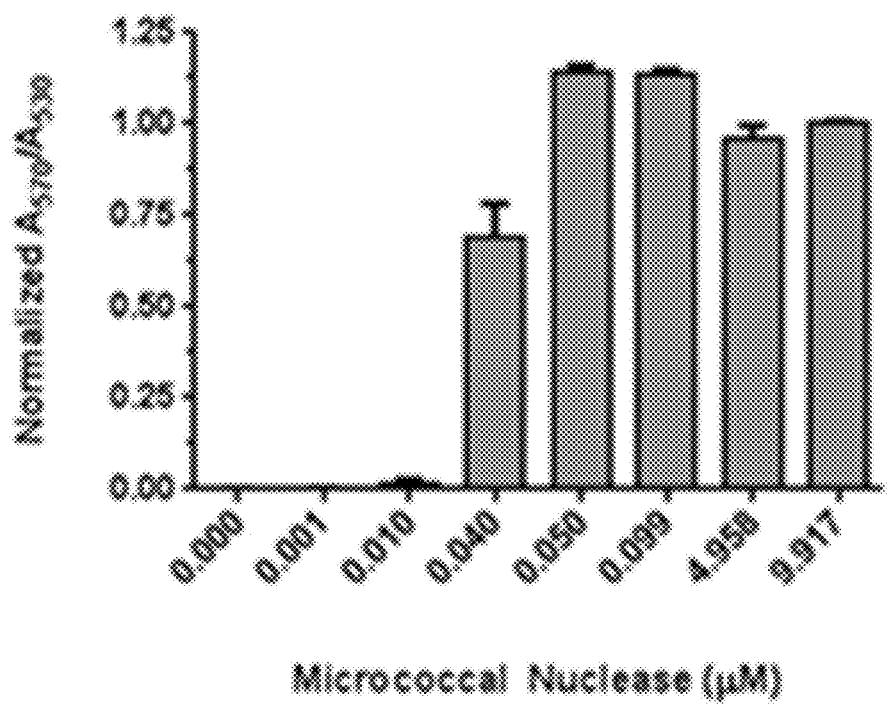
Figure 10I:
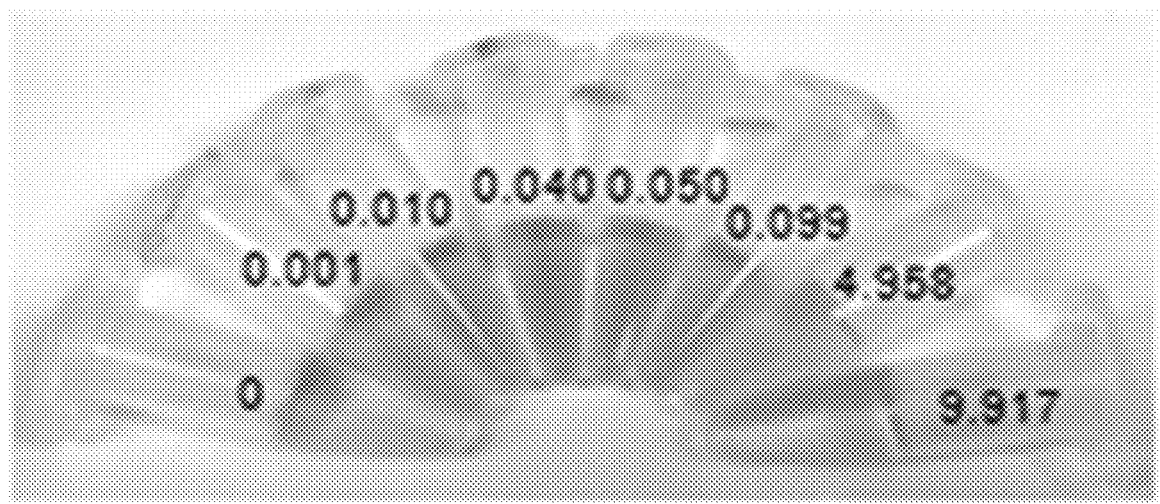

Next, to understand constraints on testing conditions, the concentration of the Oligo-AuNPs (0.5 nM in FIG. 1 and FIG. 2) and pH (7 in FIG. 1 and FIG. 2) were investigated to determine if they affected the limit of detection. When the concentration of Oligo-AuNPs was reduced by half to 0.25 nM the sensitivity to MN remained unchanged (FIG. 9A-9C), and when it was increased to 1 nM Oligo-AuNPs the sensitivity was again unchanged (FIG. 9D-9F). In order to be used in applications, the Oligo-AuNPs must be able to function in various pH solutions. The particles proved to be stable in solutions ranging from pH 4-10 (FIG. 10A-10C) with no meaningful change in limit of detection (0.04 µM MN at pH 4 and 0.05 µM at pH 10, FIG. 10D-10I). These experiments showed that under a reasonable working range the sensitivity of the Oligo-AuNPs was not concentration or pH dependent.

Figure 3A:
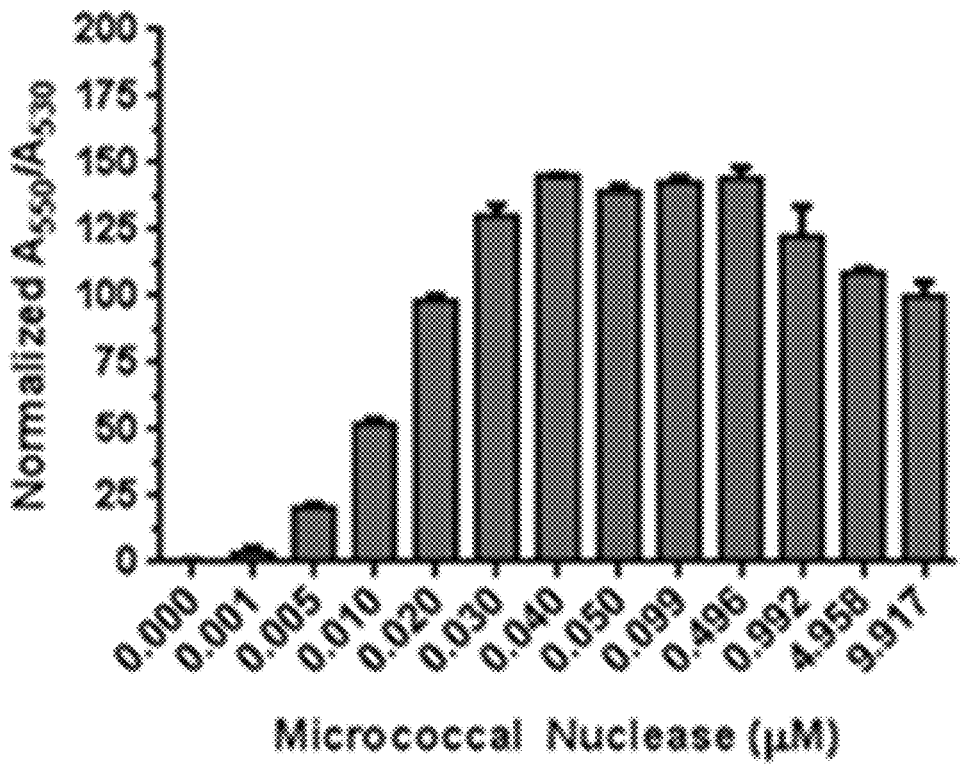
FIGS. 3A-D. Oligo-AuNP mechanism of detection.
Figure 3B:
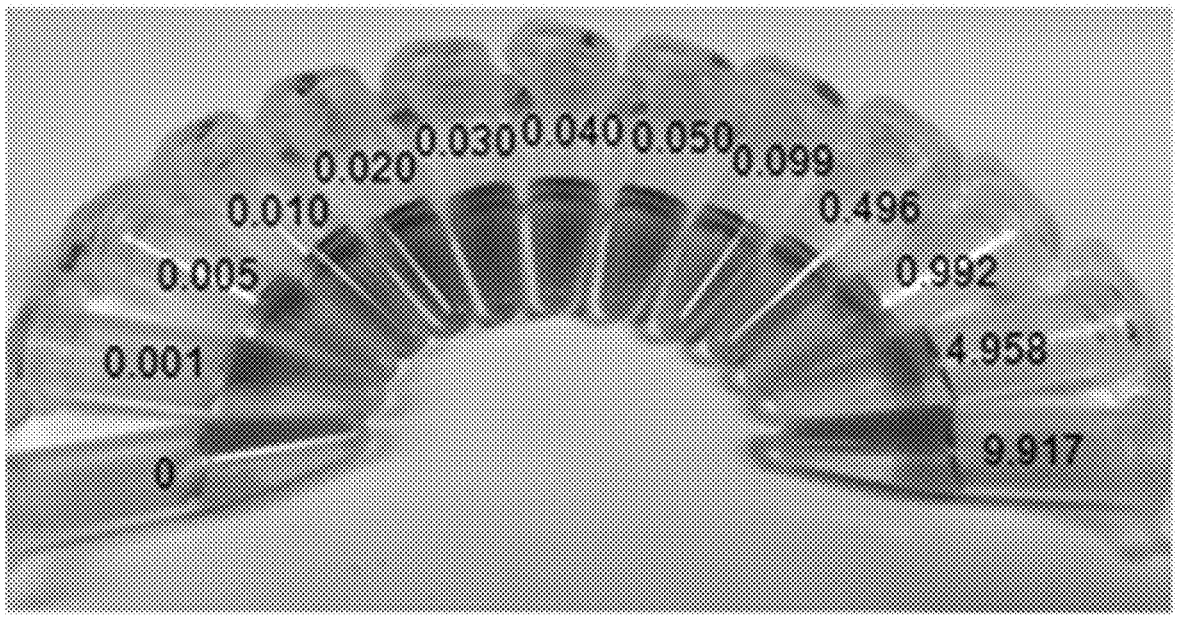
Figure 3C:
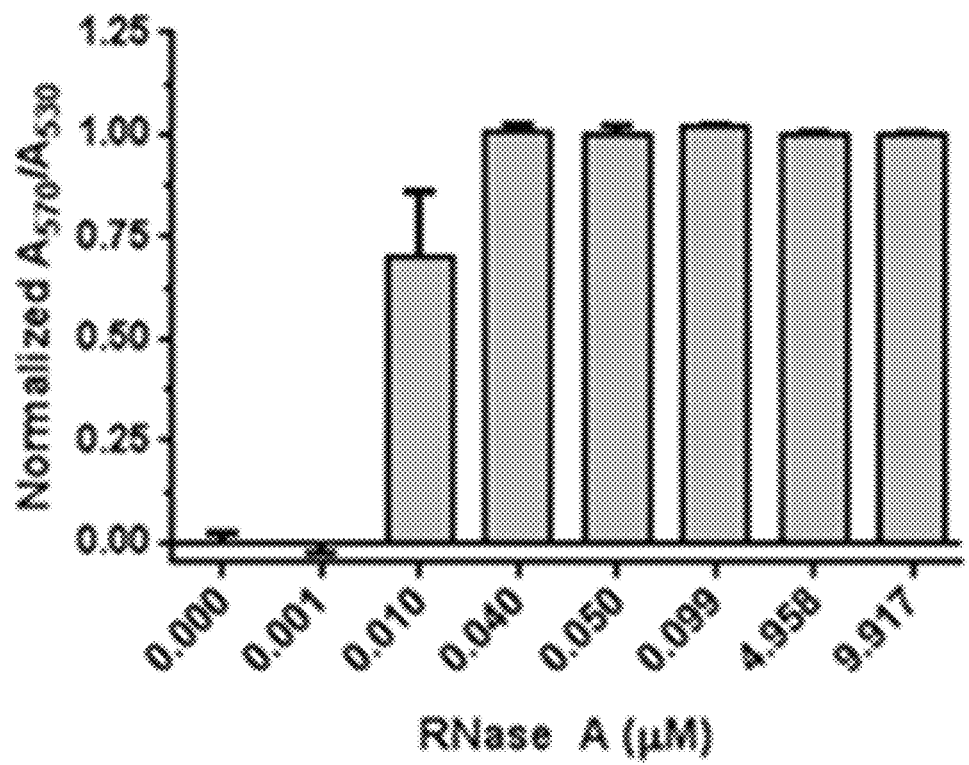
Figure 3D:
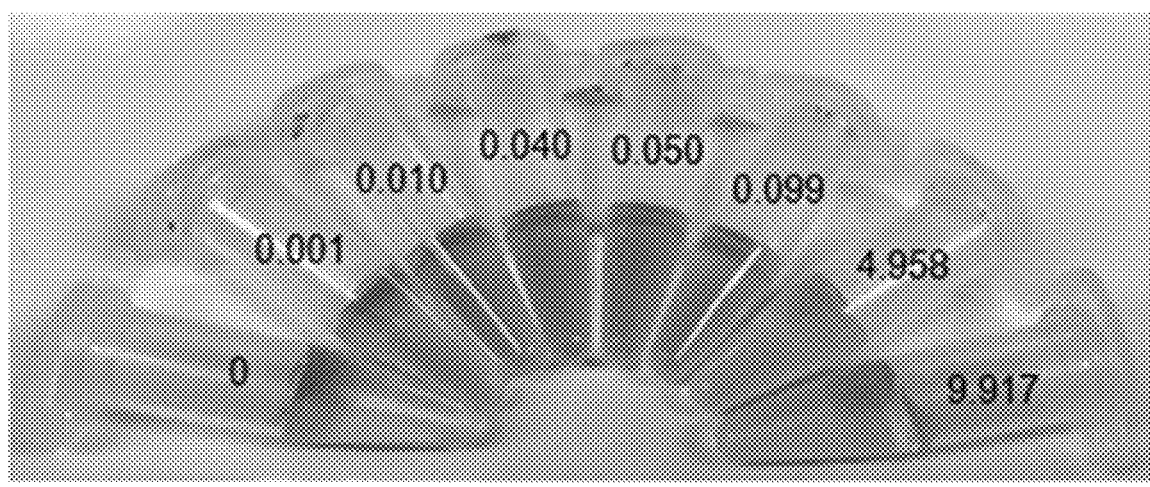
Figure 13A:
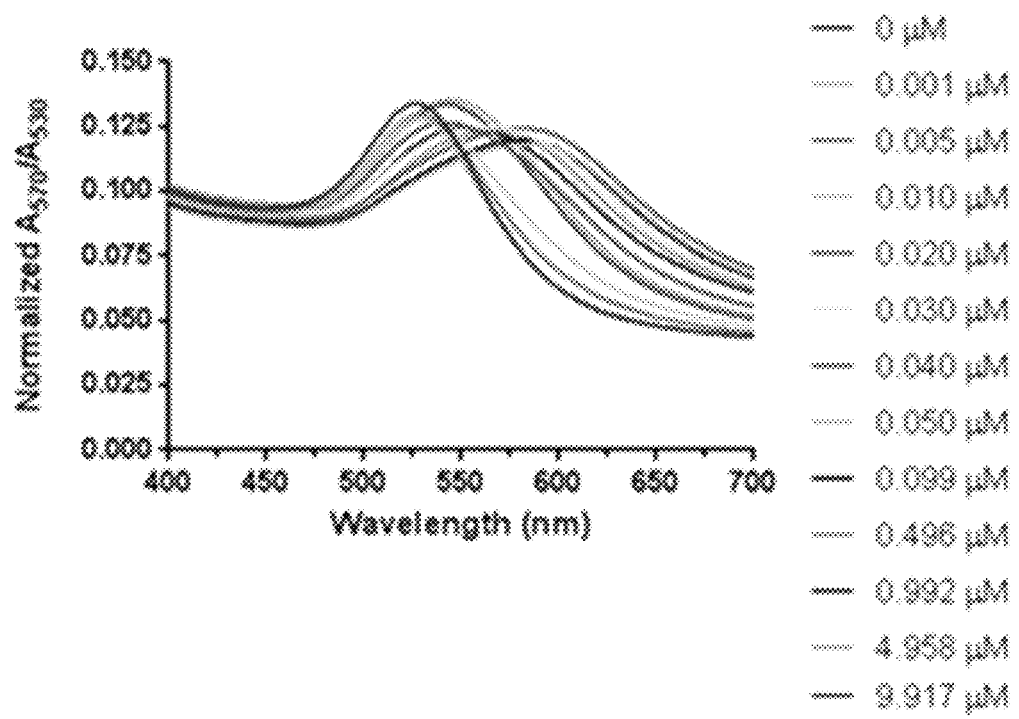
FIGS. 13A-13B.
Figure 13B:
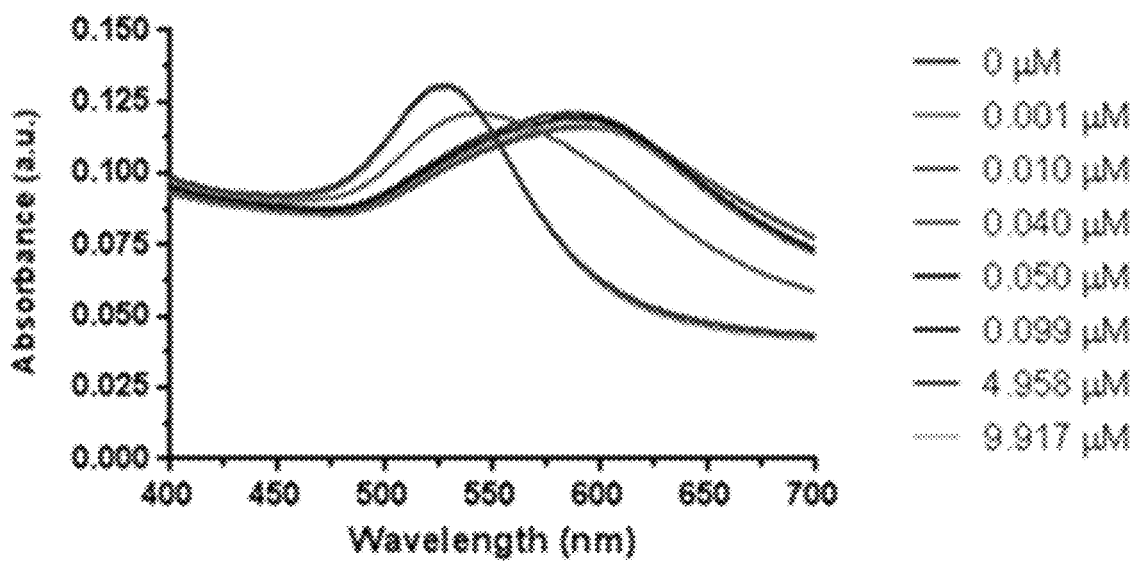

At the outset of the studies, Applicants hypothesized that cleavage of the oligo coating on the AuNPs would occur between the deoxythymidines leaving behind a 5-mer coating and it was unclear if the relatively modest change in coating from an 11-mer to a 5-mer following cleavage would induce aggregation of the AuNPs. Having observed that aggregation did occur in a rapid fashion, Applicants investigated why this process occurred by preparing AuNPs directly functionalized with the thiolated 5-mer oligonucleotide. The 11-mer and 5-mer Oligo-AuNPs were very similar in size, charge, UV-spectrum, and TEM imaging (Table 4, FIGS. 13A-13C). The one significant difference was the number of oligonucleotide strands coating the AuNPs, with the 5-mer Oligo-AuNPs having 1327 strands/AuNP and the 11-mer Oligo-AuNPs having 877 strands/AuNP. This difference likely arises because the larger and more highly charged 11-mer cannot be packed as densely on the AuNP surface. Thus, one possible mechanism of detection is that when the 11-mer coating is cleaved there are not enough 5-mer strands to fully coat the AuNP surface and aggregation occurs. However, a second possibility is that the 5-mer coating is further degraded. Indeed, Applicants found that the 5-mer Oligo-AuNPs were sensitive to MN with a limit of detection of 0.020 µM MN (FIGS. 3A and 3B and FIG. 13A). With higher concentrations of MN used (4.958 µM to 9.917 µM) the Oligo-AuNPs rapidly aggregate and coat the eppendorf tube, causing the solution of aggregated Oligo-AuNPs to appear as light purple. Also, the $\lambda_{max}$ at 9.917 µM MN shifted to 550 nm. In order to determine limit of detection, the ratio of the UV absorbance signal at 550 nm to 530 nm was taken instead. Interestingly, the 5-mer Oligo-AuNPs had limited selectivity as aggregation was also observed with RNase A and the limit of detection was 0.010 µM RNase A (FIGS. 3C and 3D and FIG. 13B) indicating that the full sequence is required for selective detection. Based on this data, the working hypothesis is that detection occurs via initial cleavage between the deoxythymidines and subsequent continued degradation of the residual 5-mer sequence.

TABLE 4

Oligo-AuNPs were characterized by DLS, Zeta Potential, and DTT displacement. Both the 5-mer and 11-mer Oligo-AuNPs were equivalent in diameter and surface charge. However, there were more strands of oligonucleotides on the 5-mer Oligo-AuNPs compared to the 11-mer Oligo-AuNPs.

| Oligo-AuNP Comparison | 11-mer Oligo-AuNP | 5-mer Oligo-AuNP |
|---|---|---|
| DLS | 33.3 ± 0.753 nm | 29 ± 0.737 |
| PDI | 0.049 ± 0.006 | 0.06 ± 0.016 |
| Zeta Potential | −20.65 ± 2.375 | −17.34 ± 0.245 |
| Oligo/AuNP | 876.5 ± 60 strands | 1327.16 ± 81 strands |

Figure 4A:
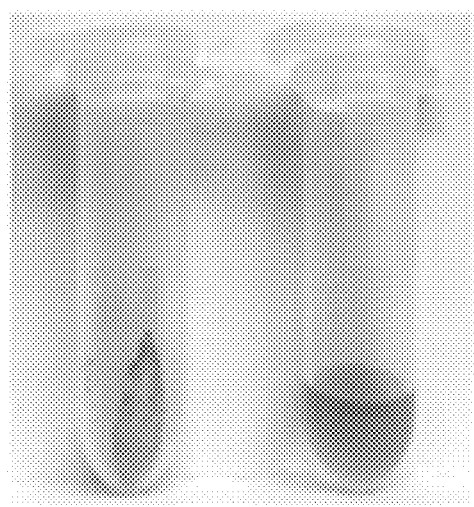
FIGS. 4A-4G.
Figure 4B:
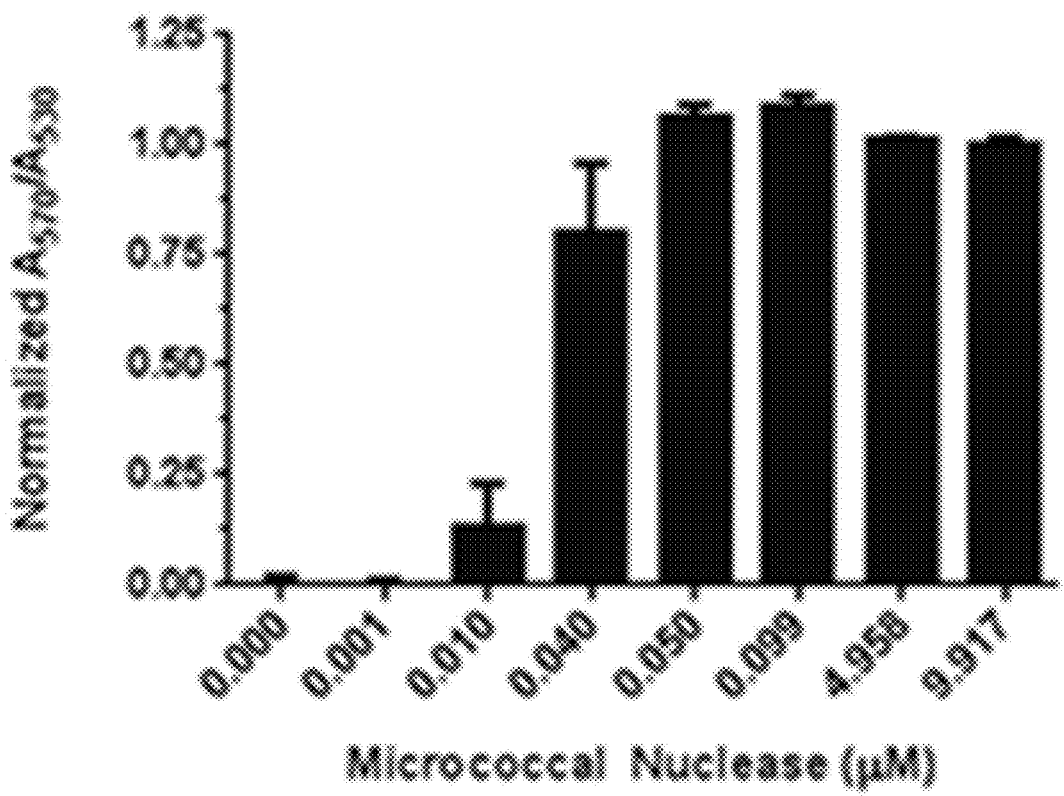
Figure 4C:
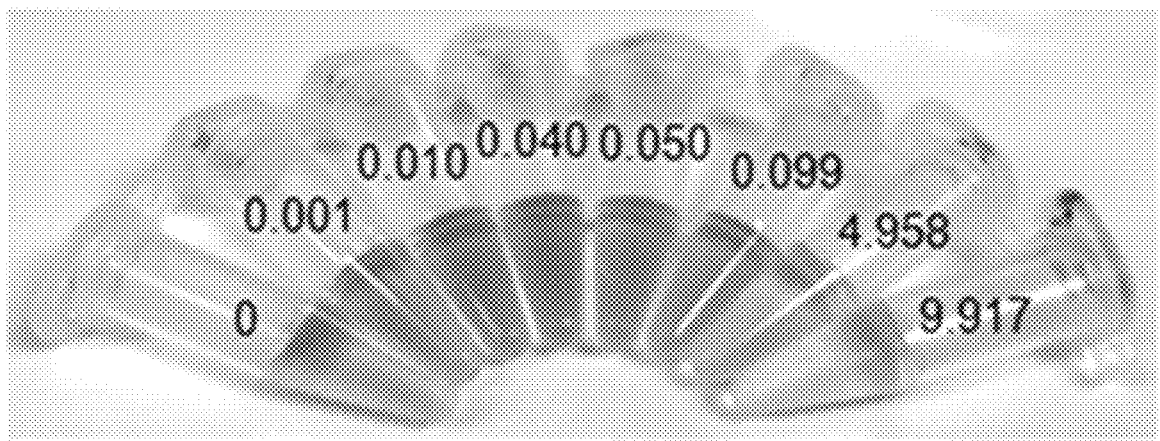
Figure 4D:
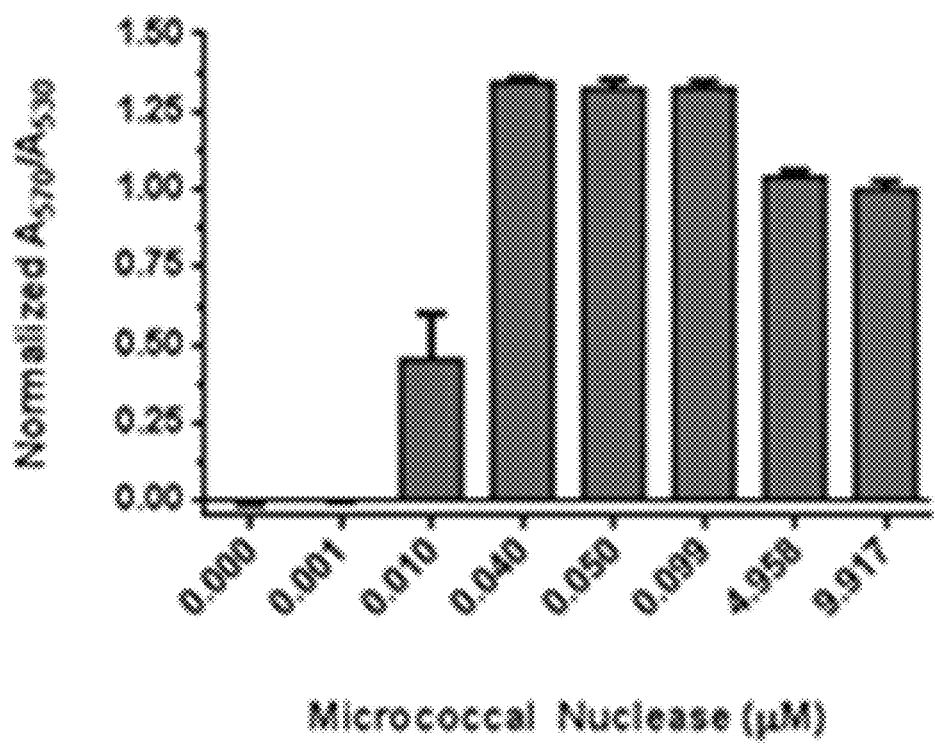
Figure 4E:
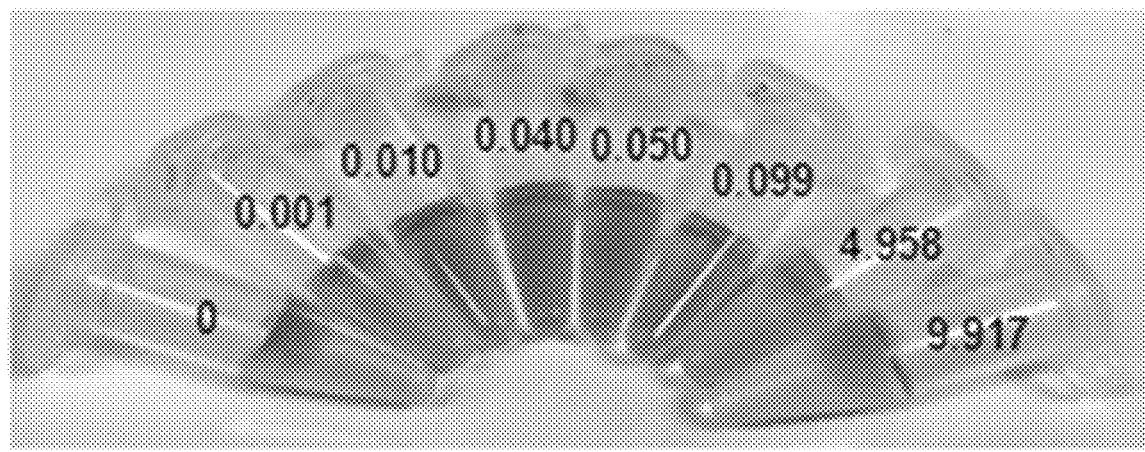
Figure 4F:
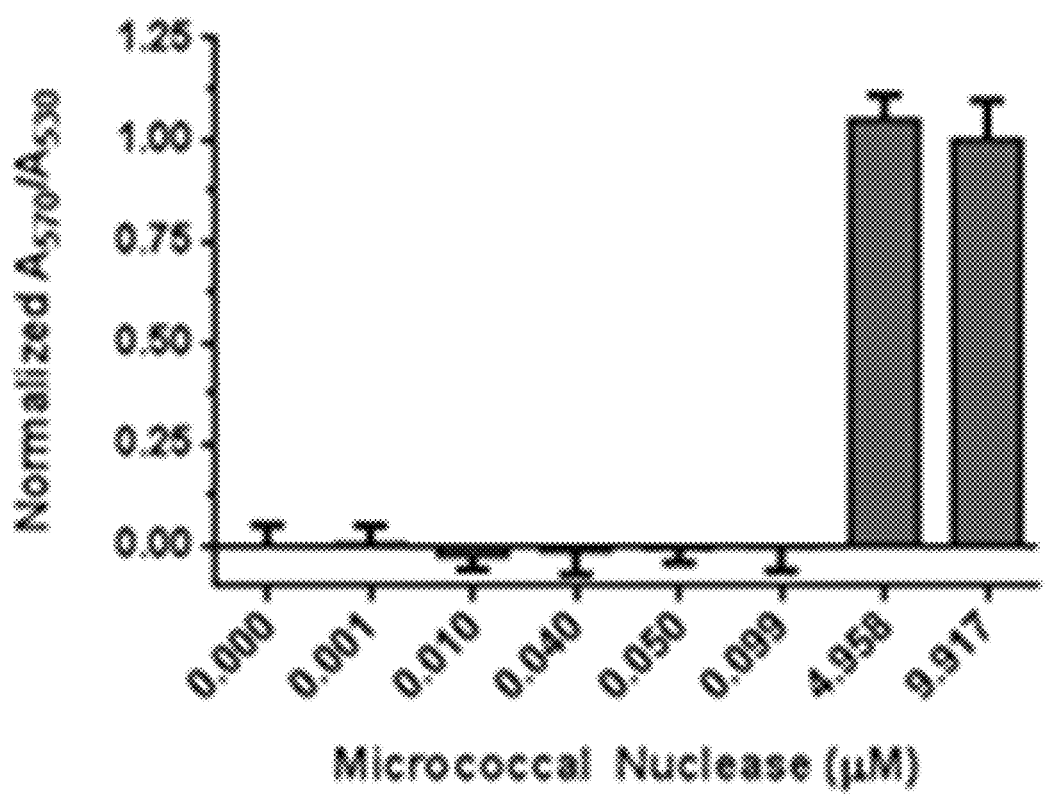
Figure 4G:
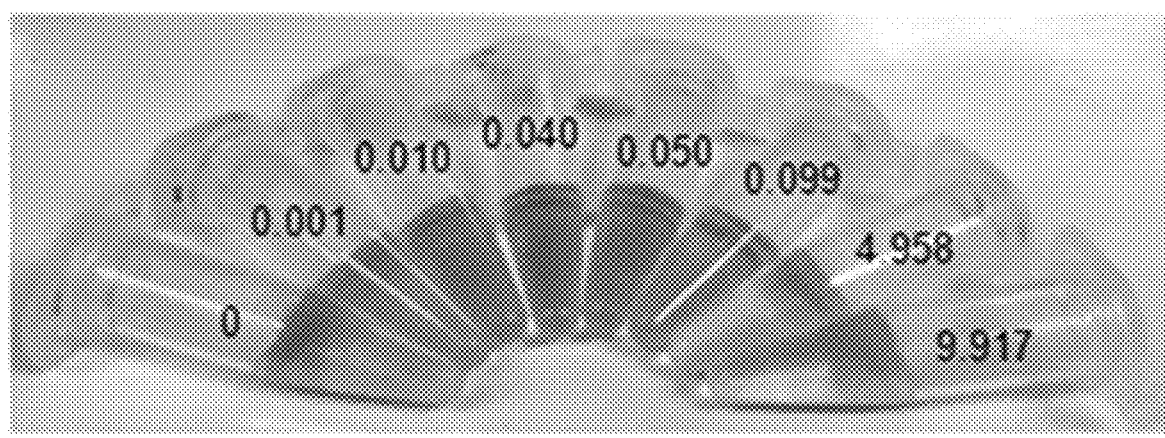
Figure 14A:
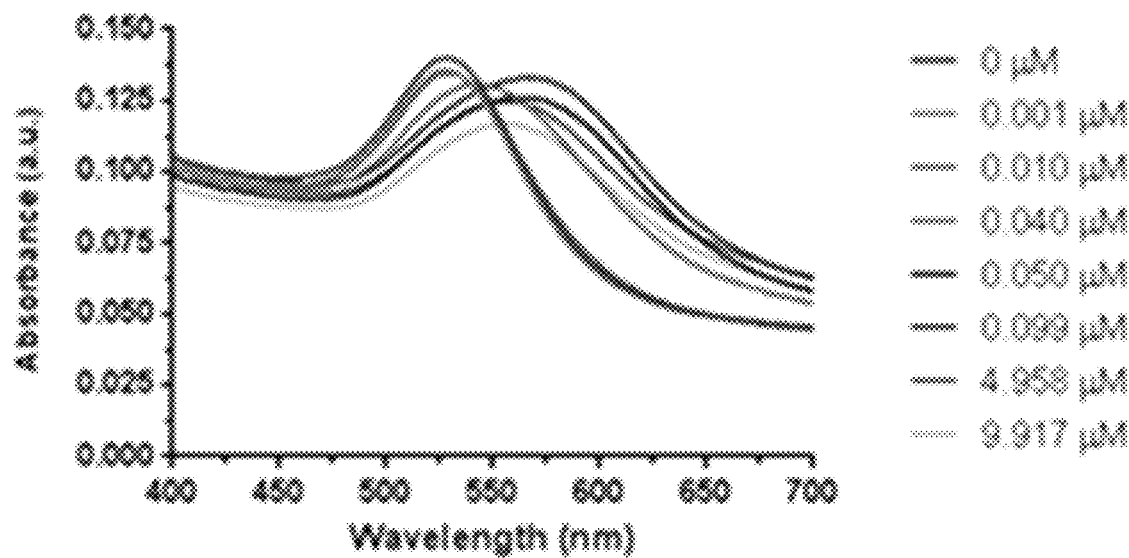
FIGS. 14A-14C.
Figure 14B:
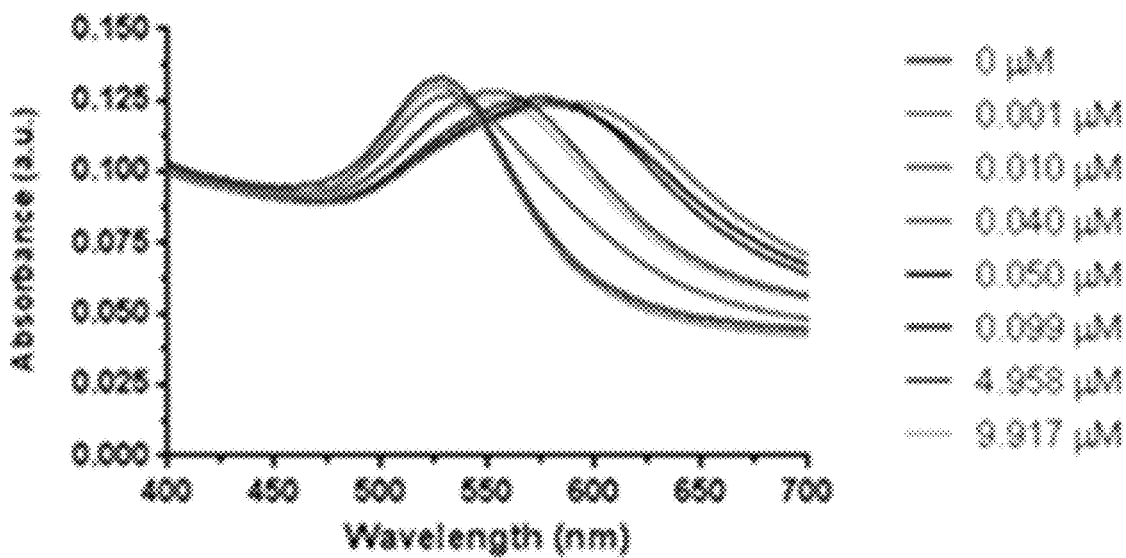
Figure 14C:
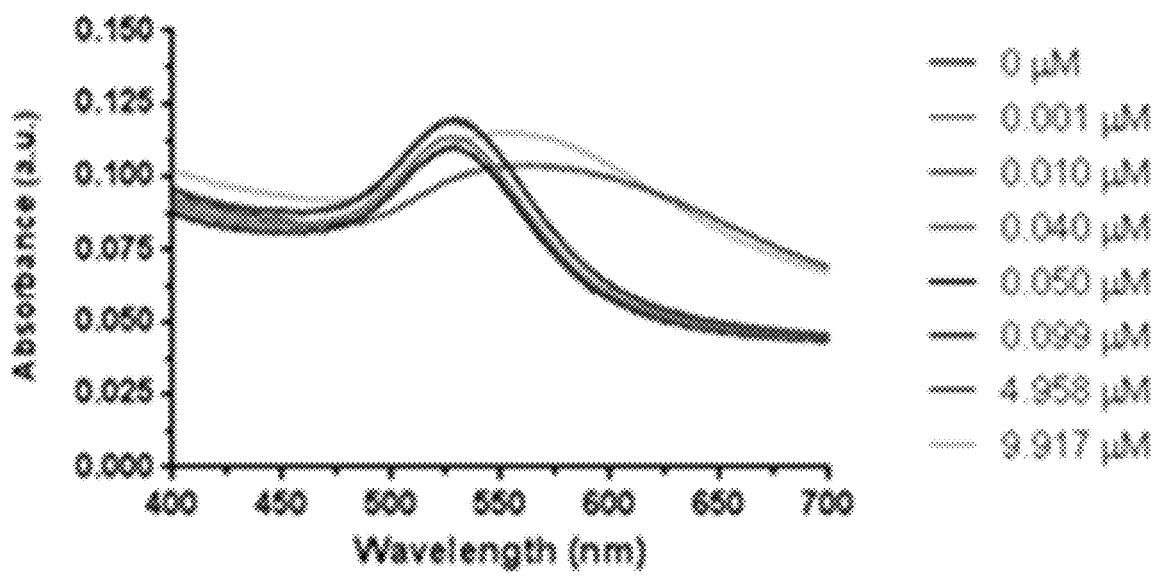
Figure 15A:
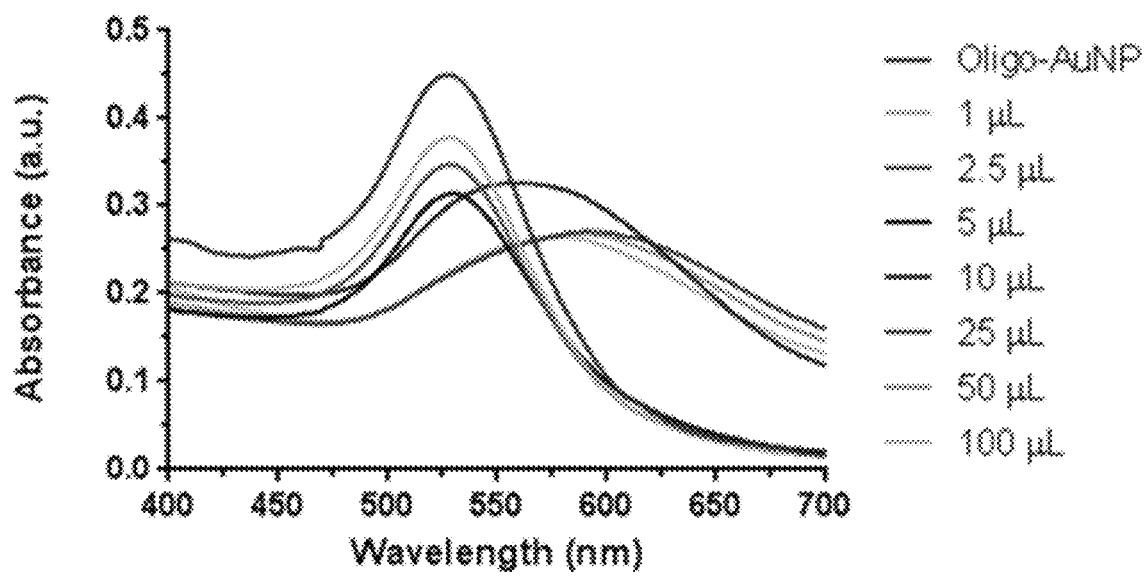
FIGS. 15A-15B.
Figure 15B:
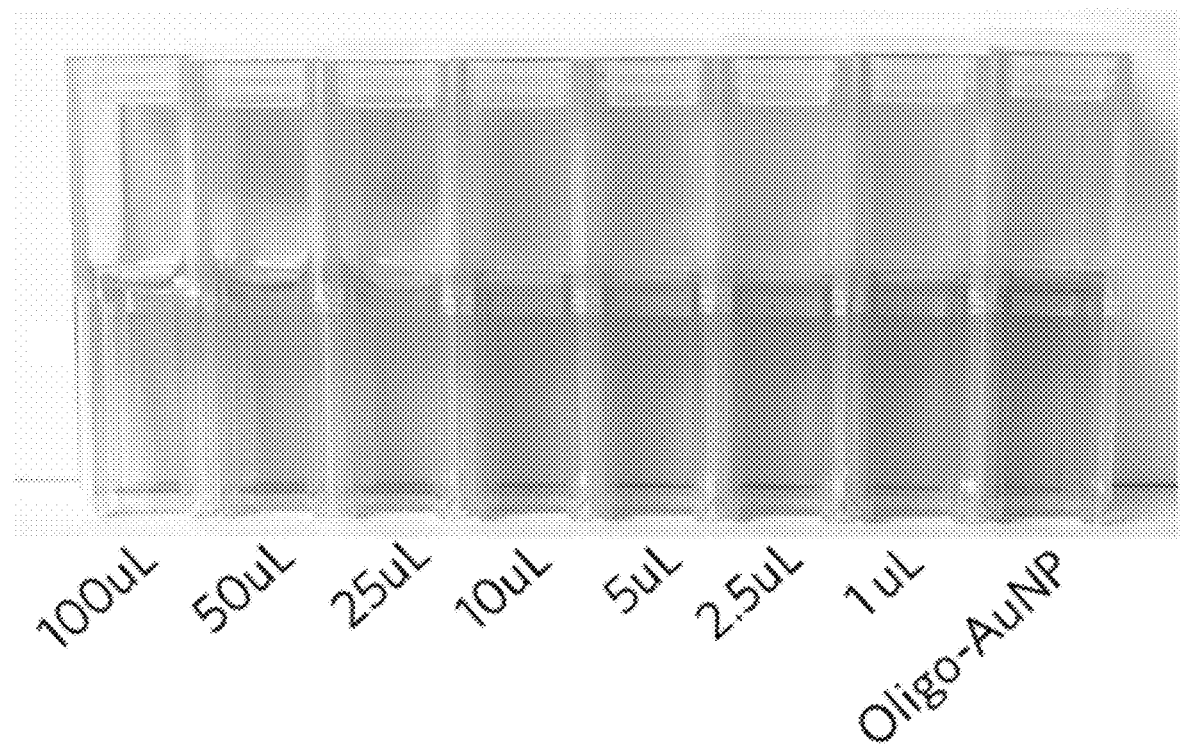

In order to facilitate transportation and use of the Oligo-AuNPs, Applicants next identified conditions that allowed the Oligo-AuNPs to be lyophilized and stored as a dry powder while retaining their limit of detection. Adapting a protocol previously reported by Stone and co-workers,[36] trehalose was added to Oligo-AuNPs and the mixture was lyophilized overnight. The lyophilized Oligo-AuNPs were able to be reconstituted in water (FIG. 4A). When the dry powder was reconstituted, the limit of detection was found to be 0.040 almost identical to the as-prepared Oligo-AuNPs (FIGS. 4B and 4C, FIG. 14A). The trehalose-stored Oligo-AuNPs were further tested by using them in a more complex media, such as creek water and ocean water spiked with various concentrations of MN. When resuspended into creekwater, the Oligo-AuNPs had a limit of detection of 0.04 µM MN (FIGS. 4F and 4G and FIG. 14B). Oligo-AuNPs treated with 4.958 µM to 9.917 µM MN undergo a colorimetric change from pink to light purple. This is due to rapid aggregation of the Oligo-AuNPs, which causes precipitation of the aggregates and adherence on the eppendorf tube causing the solution to be a lighter shade of purple. A colorimetric detection was observed in the ocean water sample, albeit with a decrease in sensitivity in limit of detection to 4.958 μM MN (FIGS. 4H and 4I, and FIG. 14C). This suggests that the Oligo-AuNPs may be suitable for real world application.

Figure 5A:
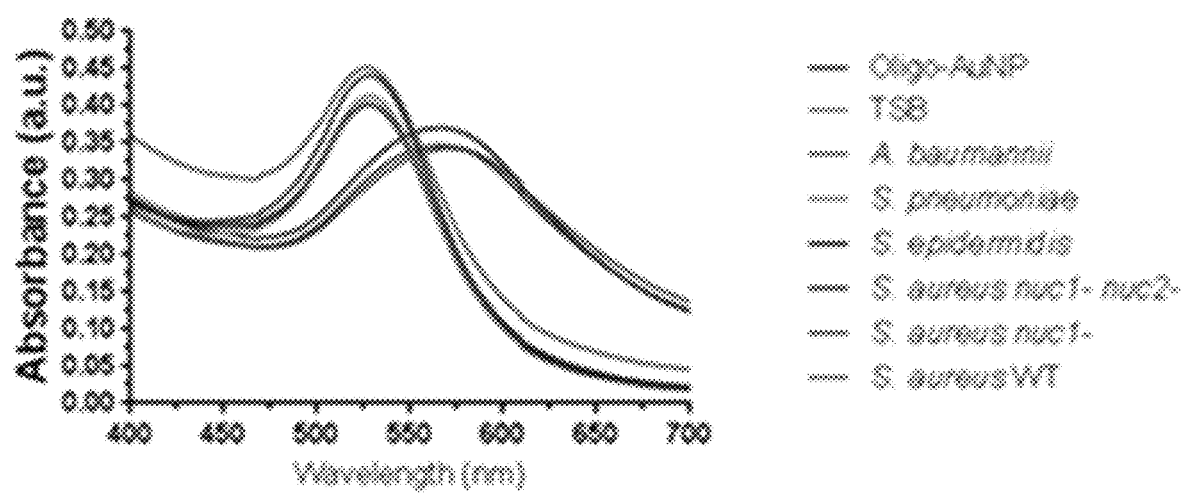
FIGS. 5A-5D. Oligo-AuNPs were treated with various bacterial supernatants.
Figure 5B:
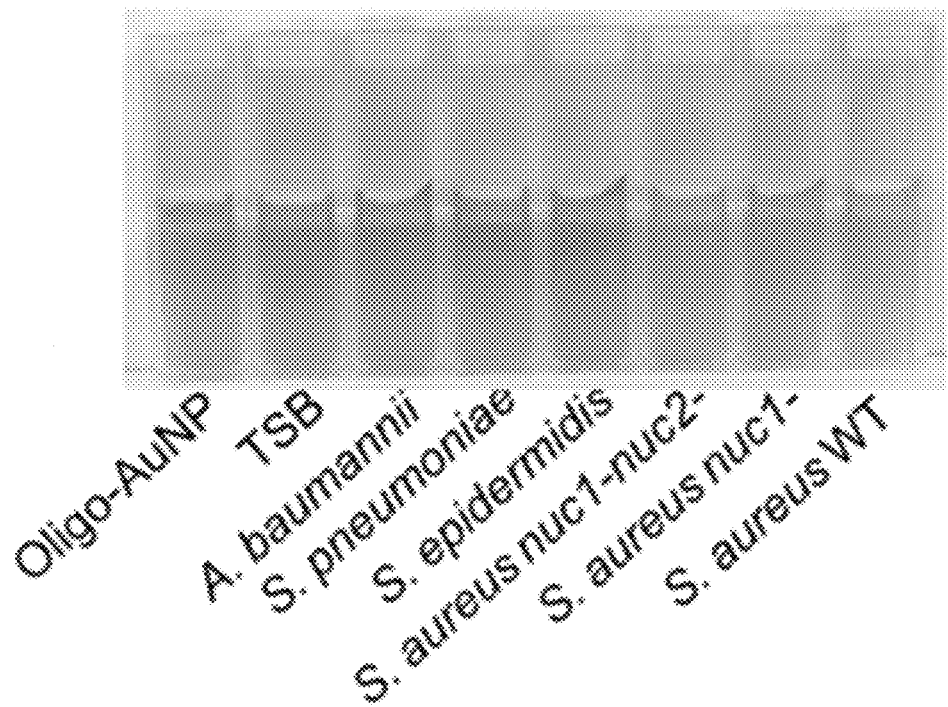
Figure 5C:
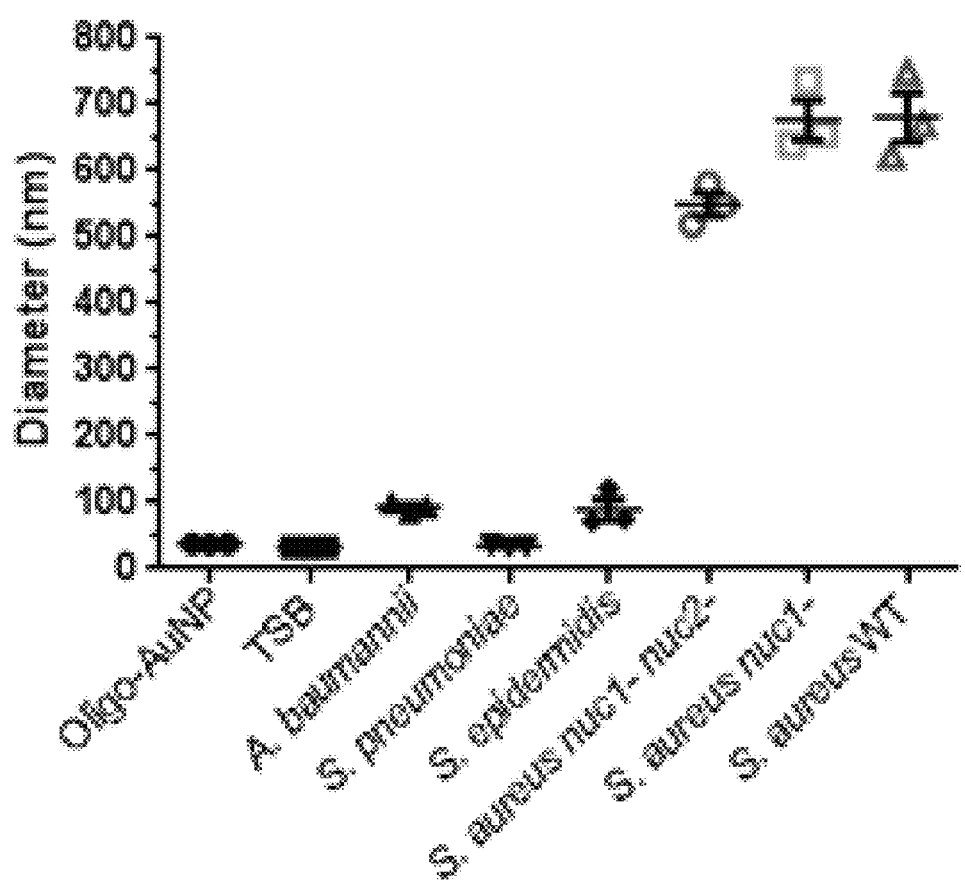
Figure 5D:
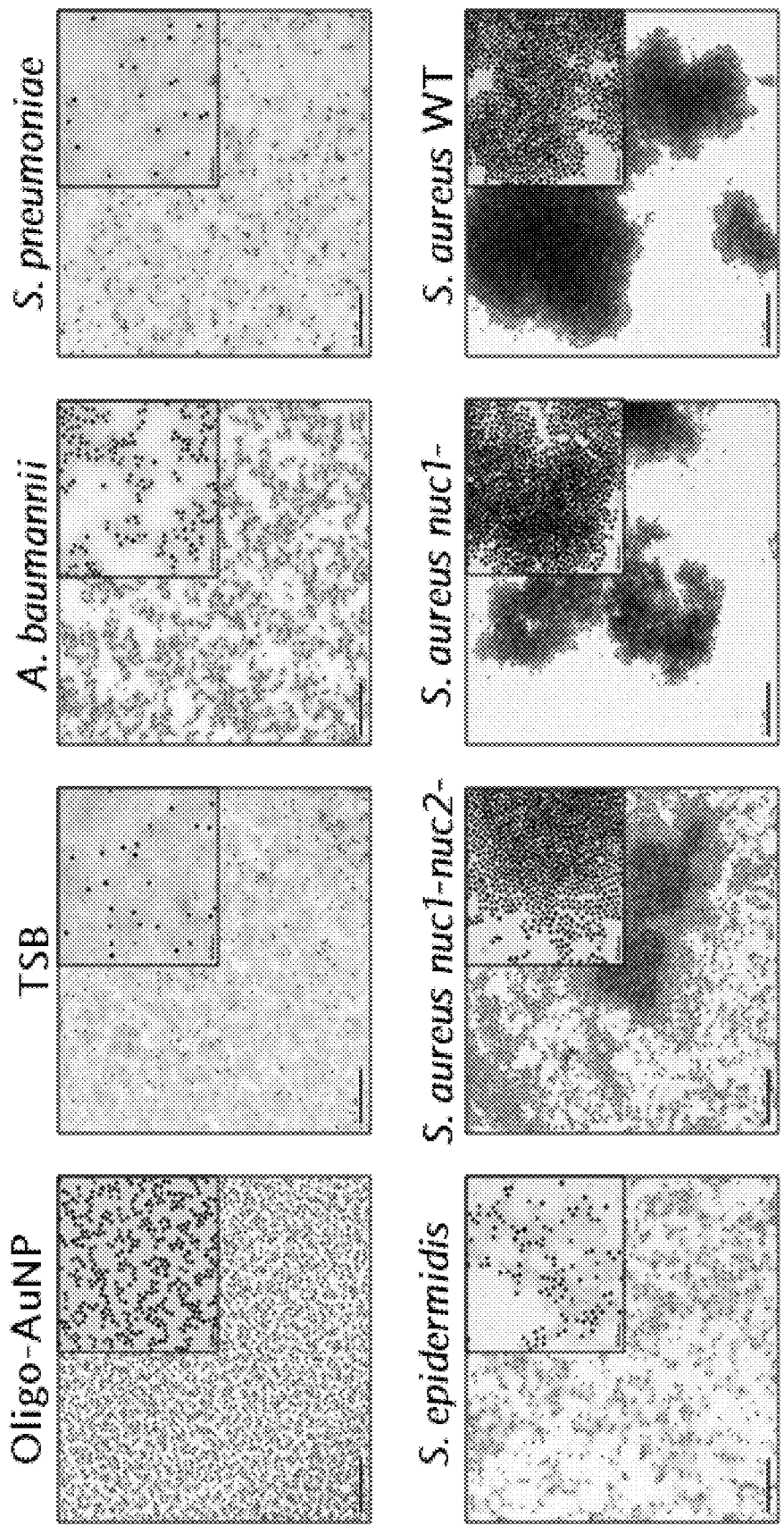
Figure 16A:
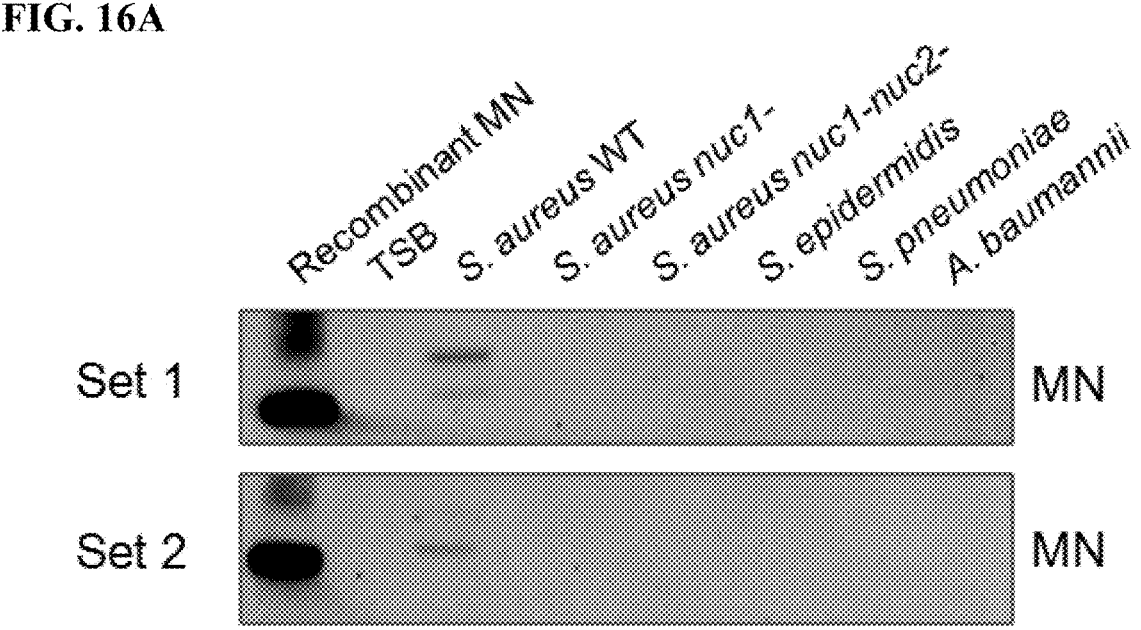
FIGS. 16A-16B.
Figure 16B:
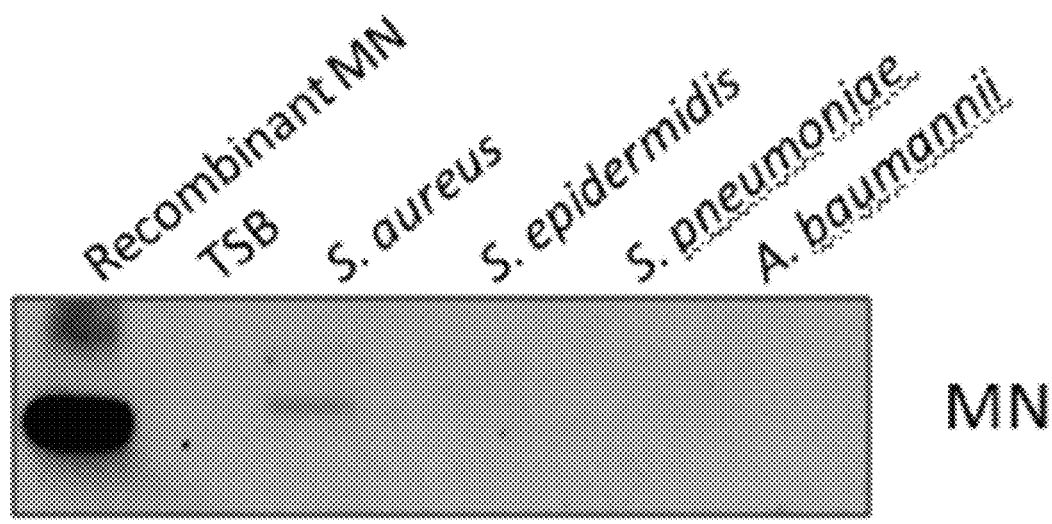
Figure 17A:
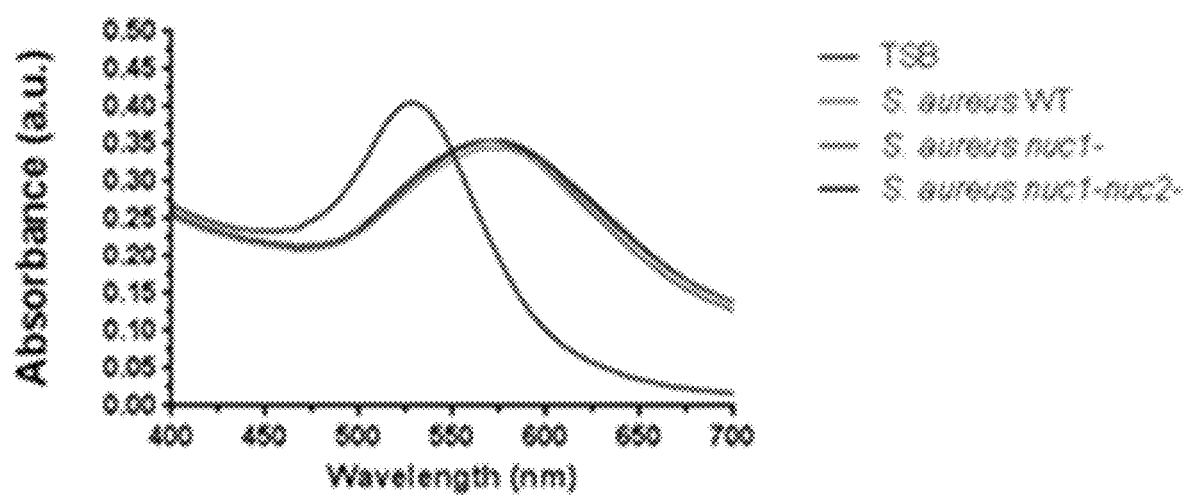
FIGS. 17A-17F.
Figure 17B:
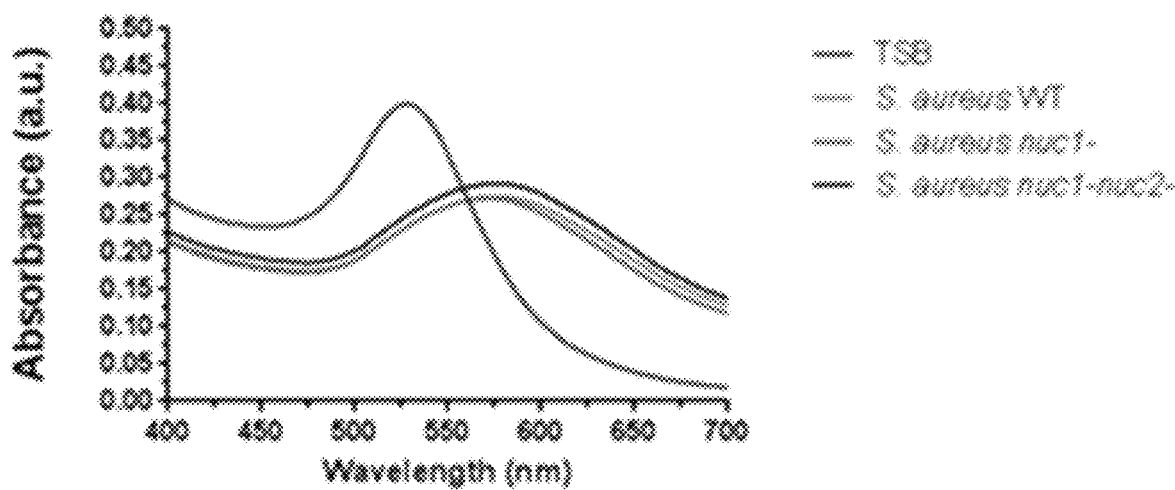
Figure 17C:
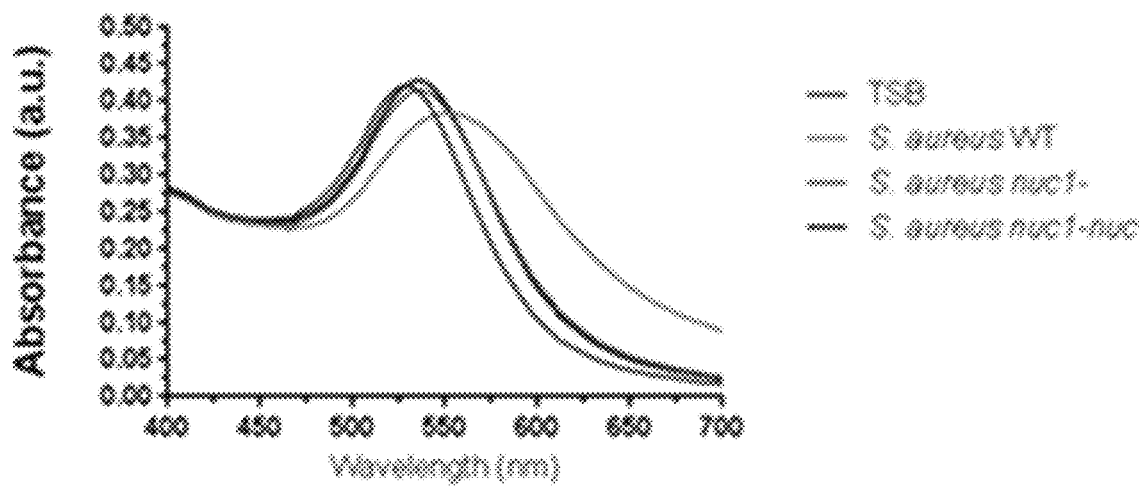
Figure 17D:
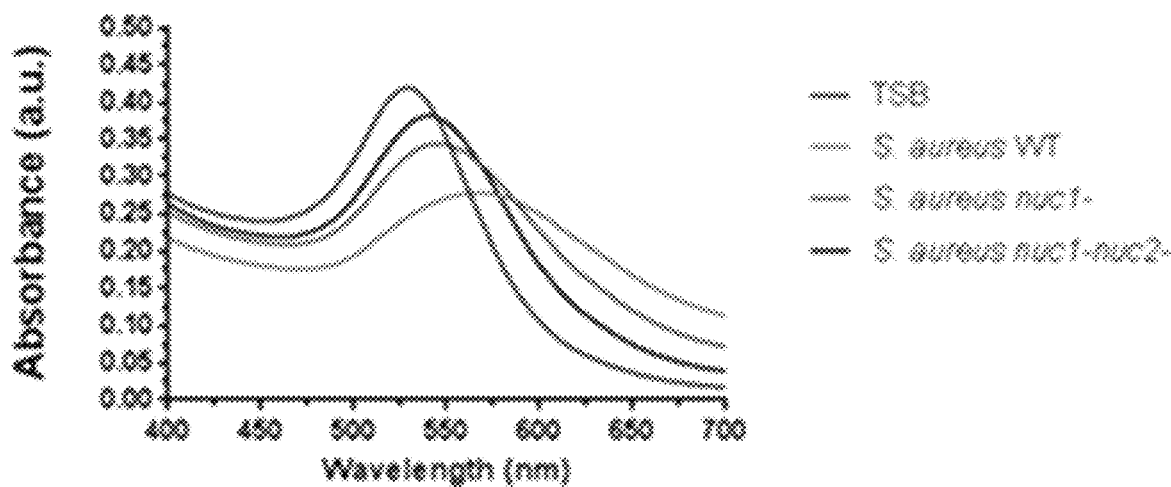
Figure 17E:
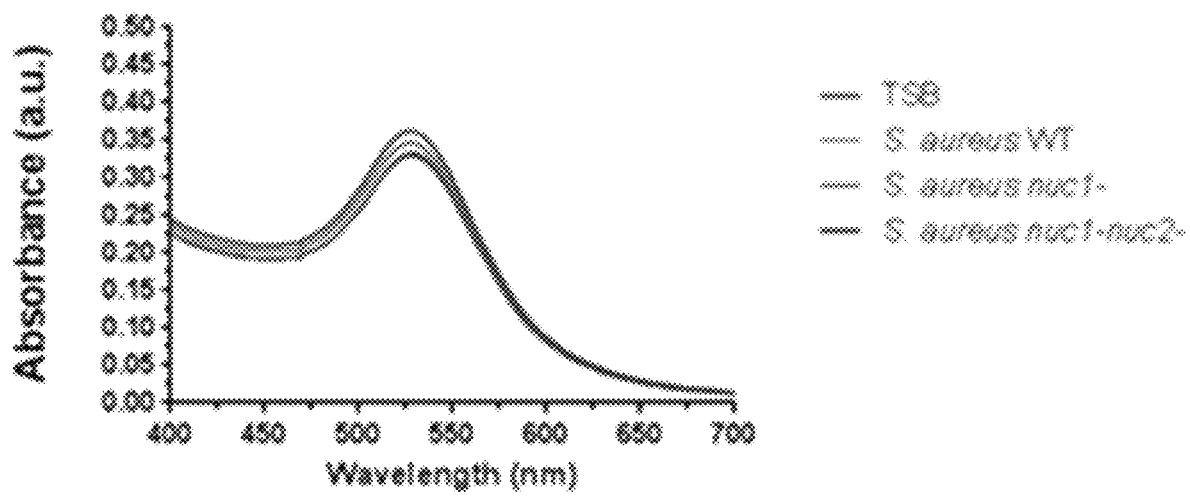
Figure 17F:
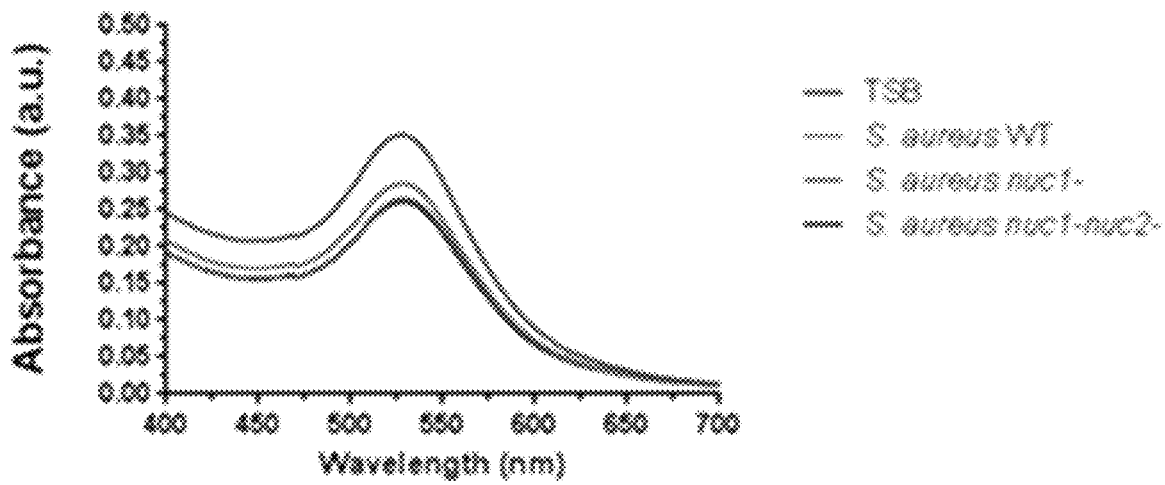

Finally, having observed selective aggregation using purified enzyme, Applicants proceeded to test the Oligo-AuNPs against culture supernatants of various bacterial species: *Acinetobacter baumannii* (*A. baumannii*), *Streptococcus pneumoniae* (*S. pneumoniae*), *Staphylococcus epidermidis* (*S. epidermidis*), and *Staphylococcus aureus* (*S. aureus*) WT. The bacteria were cultured in Tryptic Soy Broth (TSB) (*S. aureus* WT, *S. pneumoniae* and *S. epidermidis*) or Nutrient Broth (*A. baumannii*). The culture supernatants were separated from the bacteria via centrifugation. The various samples were then added to a solution of Oligo-AuNPs (0.5 nM) in water and within 5 minutes, the Oligo-AuNPs exposed to *S. aureus* culture supernatants changed color from red to purple with a corresponding shift in $\lambda_{max}$ from 530 nm to 570 nm (FIGS. 5A and 5B). Oligo-AuNPs treated with supernatant from *A. baumannii*, *S. pneumoniae*, and *S. epidermidis* did not aggregate or change color in solution even after 1 hour, which validates the Oligo-AuNPs specificity to *S. aureus*. As measured by DLS, the Oligo-AuNPs dramatically increased in size following treatment with *S. aureus* supernatant but not the other supernatants (FIG. 5C). By TEM, Applicants also observed mass aggregation of Oligo-AuNPs when treated with *S. aureus* culture supernatant while the particles were unchanged for all other treatments (FIG. 5D). The minimum volume of *S. aureus* WT supernatant needed to cause Oligo-AuNPs to aggregate was determined to be 10 μL (FIGS. 16A and 16B). The fluorescent probe showed equivalent specificity to the Oligo-AuNPs when tested using these supernatants (FIG. 18A).

Figure 18A:
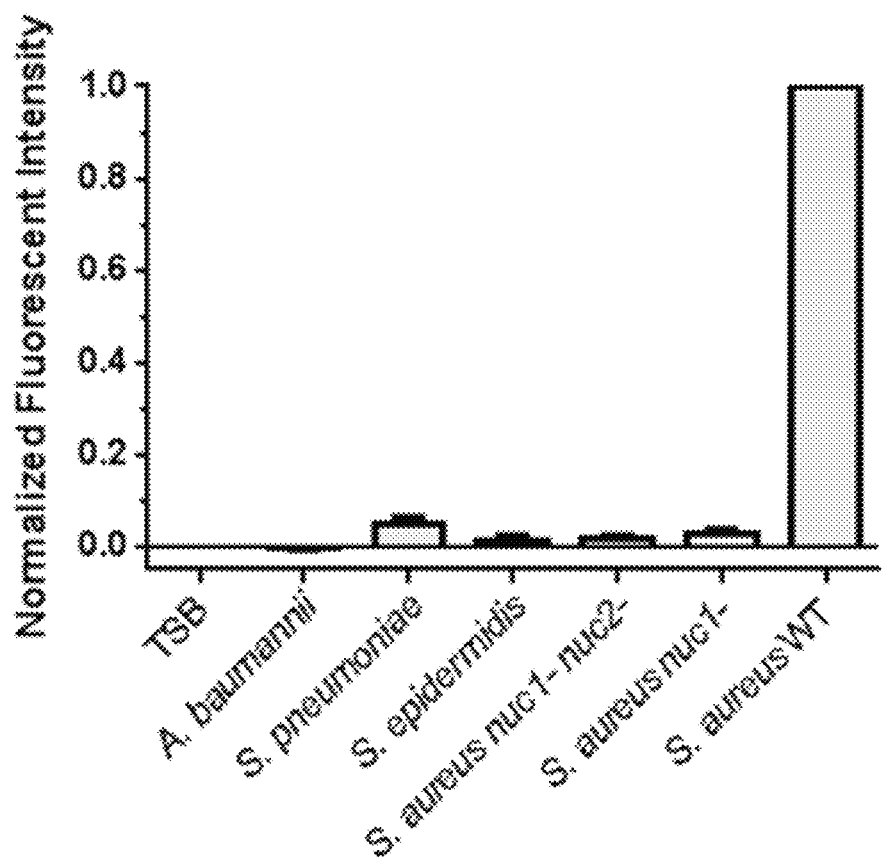
FIG. 18A. The fluorescent probe was treated with various bacterial supernatants. The fluorescent probe was specific to only the S. aureus WT supernatant.

In an attempt to validate that selective detection of *S. aureus* in unpurified supernatants was functioning via the same mechanism as the studies with purified MN, Applicants tested the 5-mer Oligo-AuNPs and were surprised to find that they also only aggregated in the *S. aureus* supernatant (FIG. 18A). Applicants also tested supernatants from two knockout strains, *S. aureus* nuc1-, and *S. aureus* nuc1-nuc2-. Expression of Nuc1 (MN) was knocked out in *S. aureus* nuc1-. In *S. aureus* nuc1-nuc2-, MN and Nuc2, a second secreted nuclease, were both knocked out and verified by Western blot (FIGS. 16A and 16B). Surprisingly, the *S. aureus* nuc1- and *S. aureus* nuc1-nuc2- supernatants also caused the Oligo-AuNPs to aggregate as well. The aggregation and color change seen in Oligo-AuNPs treated with supernatant from *S. aureus* WT, *S. aureus* nuc1-, and *S. aureus* nuc1-nuc2- suggests that other factors (e.g., other nucleases) could play a role in causing the Oligo-AuNPs to aggregate.

In order to better understand the mechanism of aggregation observed with the knockout strains, Applicants further tested the various *S. aureus* supernatants in the presence and absence of $CaCl_2$. For all *S. aureus* supernatants, the aggregation of Oligo-AuNPs was accelerated upon the addition of exogenous $CaCl_2$ and eliminated when EDTA was added (FIG. 17A-17F). In background salt conditions, Oligo-AuNPs treated with *S. aureus* WT supernatant aggregated in 5 min and the $\lambda_{max}$ shifted to 560 nm. However, supernatant from the two *S. aureus* knock-out strains did not cause aggregation or a shift in $\lambda_{max}$ to occur after 5 minutes. After 1 hour, the $\lambda_{max}$ of Oligo-AuNPs treated with *S. aureus* WT supernatant fully shifted to 570 nm. However, the $\lambda_{max}$ of *S. aureus* nuc1- shifted to 545 nm and the $\lambda_{max}$ of *S. aureus* nuc1-nuc2- shifted to 540 nm.

Conclusion

Applicants have demonstrated that Oligo-AuNPs can be used as rapid colorimetric detectors for *S. aureus*. The Oligo-AuNPs can be stored as a lyophilized powder, rendering packaging and transportation simple. Usage is also simplified since samples of interest can be used to directly resuspend the lyophilized Oligo-AuNPs. This platform has potential to be used to diagnose patients in point-of-care settings and to evaluate food and water sources, even in remote or low resource settings. Efforts to evaluate it in these circumstances are underway. By adjusting the coating, the platform should also be amenable to detecting enzymes secreted by other bacteria of interest.

Methods

All materials were used as supplied. Citrate stabilized colloidal 20 nm AuNPs were purchased from Ted Pella. Chemically modified 5-mer, 6-mer and 11-mer oligonucleotides were synthesized and purchased from the Synthetic Chemistry Core at City of Hope. The quenched fluorescent 11-mer probe was purchased from IDT. The purified MN was purchased from Worthington Biochemical Corporation. *S. aureus* AH2600, *S. pneumoniae* AH1102, and *S. epidermidis* AH2490 were provided by Dr. Alexander Horswill (University of Iowa). The clinical isolate of *A. baumannii* 3.3 was provided by Dr. Bradley Ford (University of Iowa). DTT, $NaHCO_3$, Acetic Acid, SDS, $Na_2HPO_4 \cdot 7H_2O$, NaCl, $CaCl_2$, and EDTA were purchased from Sigma Aldrich. RNase A, BCA Protein Assay Kit, 96-well microdialysis plate (3.5 k MWCO), and 1×DPBS with and without calcium and magnesium were purchased from Life Technologies. 1 k and 3 k MWCO spin filter devices were purchased from Pall Corporation. 384 Black Flat Bottom Polystyrene plate was purchased from Corning. The precast Any KD Mini-PROTEAN TGX gel was purchased from Biorad. Sheep anti-DNase IgG conjugated to horseradish peroxidase was purchased from Toxin Technology.

Fluorescent Oligonucleotide Synthesis: The oligonucleotide probes were synthesized by Integrated DNA Technologies (IDT) of Coralville, Iowa. The fluorescent 11-mer probe was synthesized using standard solid-phase phosphoramidite chemistry, followed by high-performance liquid chromatography (HPLC) purification.

TABLE 5

Name and sequence of the fluorescent 11-mer probe.

| Oligonucleotide | Sequence |
|---|---|
| TT probe (FAM labeled) | 5' FAM-mC-mU-mC-mG-T-T-mC-mG-mU-mU-mC-ZEN-RQ-3' (SEQ ID NO: 1) |

Oligonucleotide Synthesis: The 11-mer, 6-mer, and 5-mer oligonucleotides were synthesized and purified by the Synthetic and Biopolymer Chemistry Core at City of Hope. The oligonucleotide probes were synthesized on the Oligo Pilot10 plus synthesizer (GE, Piscataway, N.J. 08854) at the scale of 10 μmoles using standard phosphoramidite technology. Phosphoramidites were purchased from ThermoFisher (Milwaukee, Wis. 53202) and the remaining reagents from Tedia (Fairfield, Ohio 45014). Synthesized oligonucleotides were purified using Ion-Paired Chromatography (1). Identities of all the probes were confirmed by electron spray ionization mass spectrometry (ESI-MS) using an Oligo HTCS system (Novatia LLC). The measured molecular weights were within 1.5 Da of the expected molecular weights. The purity of the probes, as assessed with HPLC analysis, was typically greater than 90%. Quantitation of the probes was achieved by calculating from their ultraviolet absorption data and their nearest-neighbor-model-based extinction coefficients at 260 nm. Extinction coefficients of 2'-O-methyl-modified nucleotides were assumed to be the same as that of RNA.

TABLE 6

Sequences of the 11-mer, 6-mer, and 5-mer oligonucleotides.

| Oligonucleotide | Sequence |
| --- | --- |
| R-S-S-11-mer* | 5'-mC-mU-mC-mG-T-T-mC-mG-mU-mU-mC-3' (SEQ ID NO: 1) |
| 6-mer (cleaved off of AuNP) | 5'-T-mC-mG-mU-mU-mC-3' |
| R-S-S-5-mer (remains on AuNP after cleavage)* | 5'-mC-mU-mC-mG-T-3' |

*R-S-S = 5' Thiol Modifier C6 S-S?

Functionalizing Oligonucleotide onto AuNPs: Both the 11-mer (100 μL) and 5-mer (100 μL) oligonucleotides were reduced in 5 mL of 100 mM DTT and 100 mM NaHCO$_3$ for 1 hour on a shaker. DTT was removed from solution via purification by a spin filter device (3 k MWCO for 11-mer, 1 k MWCO for 5-mer). The solution was placed into the filter device and centrifuged for 20 minutes at 3220×g. After the filtrate was discarded, the oligonucleotides were washed with 30 mM acetic acid (4 mL) twice and then with H$_2$O (4 mL) three times. Following each washing the solution was centrifuged for 20 minutes at 3220×g to remove the liquid. The retentate (~100 uL) was pipetted into a new eppendorf tube and diluted with 2-3 mL H$_2$O. The absorbance at 260 nm was measured using the nanodrop spectrophotometer. If the absorbance exceeded 1, it was further diluted with H$_2$O. In order to calculate the concentration $$\left(C = \frac{A}{\varepsilon \times l}\right),$$

the absorbance (A) was divided by the product of either the extinction coefficient (ε) of the 11-mer (96,600 L/mol·cm) or the 5-mer (43,200 L/mol·cm) and the light path length. The light path length (l) used was 0.1 cm. To 10 mL of 20 nm AuNPs purchased from TedPella (1.1624 nmol AuNPs/L, 0.0116 nmol) was added a 5000× excess of oligonucleotide (1 mL, 58.12 nmol), which was then allowed to incubate on a shaker overnight at RT. The next morning, the AuNP solutions underwent salt-aging over five hours. At each hour, 22 or 75 μL of 1% SDS was added to the AuNPs and then quickly vortexed. Immediately after, 22 or 75 μL of 1M Na$_2$HPO$_4$·7H$_2$O was added followed by 550 μL of 2 M of NaCl. Each addition at every hour increased the buffers by 0.02% or 0.0075% SDS, 2 mM Na$_2$HPO$_4$·7H$_2$O, and 0.1 M NaCl. After each round of addition, the solution was sonicated for 10 seconds in a sonicator waterbath (VWR Symphony Ultrasonic Cleaner). The final buffer concentrations after 5 hours was 0.01% or 0.0375% SDS, 10 mM Na$_2$HPO$_4$·7H$_2$O, and 0.5 M NaCl. The Oligo-AuNPs were then incubated overnight. In order to remove unbound oligonucleotide strands, the AuNPs were centrifuged at 16,000×g for 20 minutes. The supernatant was discarded. The Oligo-AuNPs were then washed 3× and dispersed in 10 mL H$_2$O. UV absorbance of the Oligo-AuNPs was measured (525 nm) using a spectrophotometer. To determine the concentration, the absorbance of the Oligo-AuNPs at 525 nm was divided by the extinction coefficient of the 20 nm AuNPs (9.016×10$^8$ L/mol·cm). The path length used was 1 cm. The solution was then diluted with H$_2$O to reach a final concentration of 0.5 nM Oligo-AuNPs. The Oligo-AuNPs were then characterized by DLS, Zeta Potential, and TEM.

Quantification of Oligo Strands on AuNPs: 1 mL of 1 M DTT in 0.18 M phosphate buffer (pH 8) was used to displace the oligonucleotides from 500 μL of Oligo-AuNPs (0.5 nM). This solution was incubated overnight. After DTT addition and incubation, the solution turned clear. The solution was placed into the filter device (11-mer Oligo-AuNPs used 3 k MWCO filter, 5-mer Oligo-AuNPs used 1 k MWCO filter) and centrifuged for 20 minutes at 3220×g. The filtrate was discarded. The retentate was washed with 4 mL H$_2$O five times, following each washing, the solution was centrifuged for 20 minutes at 3220×g. The retentate was then pipetted into an eppendorf tube and placed into a speed vacuum overnight at 45° C. The pellet obtained contained only oligonucleotide with no AuNPs detected by UV (absorbance at 260 nm for oligonucleotides, but no absorbance at >500 nm for AuNPs). The oligonucleotide pellet was resuspended into 50 μL H$_2$O and the UV absorbance was measured at 260 nm using the nanodrop spectrophotometer. To determine the concentration of oligonucleotides, the absorbance at 260 nm was divided by the product of the extinction coefficient of the 11-mer (96,600 L/mol·cm) or the 5-mer (43,200 L/mol·cm) and the light path length. The light path length used was 0.1 cm. The amount of oligonucleotides per particle was determined by dividing the number of strands by the number of AuNPs in 500 μL (1.5055×10$^{11}$ AuNPs).

Digestion of 11-mer Oligonucleotide using Purified Enzyme: 15 μL of 400 pmoles oligonucleotide were used in each reaction. 1 μL of 100 mM CaCl$_2$ was added to reach a final concentration of 2 mM CaCl$_2$. For each digestion, 0.5-1 μL of MN or 9.917 μM MN or 0.2 μg/mL RNase A (negative control) or 0.126 μM RNase A (negative control) was used. After the addition of the enzyme, H$_2$O was added to reach a final reaction volume of 50 μL. This was incubated in a 37° C. water bath for 1 hour. The digest was filtered through a 0.2 μm filter and then run on a LC-MS (Agilent 1100 HPLC coupled with an Agilent 6120 Mass Spectrometer using an Acquity UPLC BEH Phenyl Column, 1.7 μm, 2.1 mm×50 mm with 100 mM HFIP and 4 mM TEA in H$_2$O and methanol gradient at 200 μL/min flow rate). As another negative control, 5 μL of 0.5 M EDTA was added to the oligonucleotide before the addition of the enzyme.

TABLE 7

Conditions for the LC-MS analysis.

| Time (minutes) | A (%) | B (%) | Flow (mL/min) | Max Pressure (bar) |
| --- | --- | --- | --- | --- |
| 0.00 | 95 | 5 | 0.200 | 400 |
| 4.50 | 95 | 5 | 0.200 | 400 |
| 27.00 | 45 | 55 | 0.200 | 400 |
| 27.01 | 0 | 100 | 0.200 | 400 |
| 36.00 | 0 | 100 | 0.200 | 400 |
| 36.01 | 95 | 5 | 0.200 | 400 |

A = 100 mM HFIP and 4 mM TEA in H$_2$O,
B = Methanol

Treatment of 5-mer and 11-mer Oligo-AuNPs using Purified Enzyme: To a 1 mL solution of 0.5 nM Oligo-AuNPs in deionized water was added 50 µL of 0.05 µM MN or 1 unit/µL MN or 0.05 µM RNase A or 10 µg/mL MN RNAse A and 20 µL of 100 mM CaCl$_2$ to a final concentration of ~2 mM CaCl$_2$. As a negative control 50 µL of 0.5 M EDTA was added to the Oligo-AuNPs before the addition of either MN or RNase A. The Oligo-AuNP solution was then incubated in a 37° C. water bath for 5 minutes. The color of each solution was noted. UV absorbance measurements were then taken (400 nm-700 nm).

Limit of Detection: A 200 µL solution of 0.5 nM Oligo-AuNPs was used for this study. Various concentrations of MN in solution were made by serially diluting the stock sample (20 unit/µL or 198.34 µM). The glycerol concentration and water used were kept constant. 10 µL of the MN solution at various concentrations were added to the Oligo-AuNPs along with 4.2 µL of 100 mM CaCl$_2$ to reach a final concentration of 2 mM CaCl$_2$. The Oligo-AuNPs were incubated in a 37° C. water bath for 5 minutes. The color of the solution was noted. 95 µL was taken from each condition and placed into a 96-well plate. The UV absorbance was then measured using a plate reader (400 nm-700 nm).

pH Stability of Oligo-AuNPs and limit of detection at pH 4 and pH 10: Diluted acetic acid or sodium hydroxide was added to 0.02 M sodium acetate buffer in order to create solutions ranging from pH 4-10. 200 uL of Oligo-AuNPs were centrifuged at 16,000×g for 20 minutes and the supernatant was discarded. The Oligo-AuNP pellet was resuspended into the various buffers ranging from pH 4-10. Oligo-AuNPs were incubated in a 37° C. water bath for 5 minutes. The color of the solution was noted. 95 µL was taken from each condition and placed into a 96-well plate. The UV absorbance was then measured using a plate reader (400 nm-700 nm). To test the limit of detection at pH 4 or pH 10, MN was serially diluted in either pH 4 or pH 10 buffers. The glycerol concentration and buffers used were kept constant. 2 mL of Oligo-AuNPs were centrifuged at 16,000×g for 20 minutes and the supernatant was discarded. The Oligo-AuNP pellet was resuspended into either 2 mL 0.02 M sodium acetate buffer at pH 4 or pH 10. 200 µL Oligo-AuNPs were aliquoted into 8 tubes. 10 µL of the MN solution at various concentrations was added to the Oligo-AuNPs along with 4.2 µL of 100 mM CaCl$_2$. The Oligo-AuNPs were incubated in a 37° C. water bath for 5 minutes. The color of the solution was noted. 95 µL was taken from each condition and placed into a 96-well plate. The UV absorbance was then measured using a plate reader (400 nm-700 nm).

Fluorescent Probe Digestion using Purified MN: Bacterial supernatants were dialyzed using a micro-dialysis cassette with a 3.5 MWCO. 110 µL of each bacterial supernatant was transferred to each dialysis cassette. 1.4 mL of 1×DPBS with calcium and magnesium was used as the dialysis buffer. The dialysis buffer was replaced with fresh 1×DPBS after 2 hours for a total of 3 washes. 2 µL of 25 µM probe (50 pmoles) in H$_2$O was used for each reaction. 8 µL of purified MN (various concentrations) was added to the probe then incubated in a water bath at 37° C. for 15 minutes. 290 µL of 1×DPBS without calcium or magnesium supplemented with 20 mM EDTA was added to each digestion condition to stop the reaction. 95 µL of each reaction condition was loaded into each well in a 384 black flat bottom well plate. The fluorescence levels were measured in a plate reader (excitation: 495 nm, emission: 516 nm). The background fluorescence level of the probe in DPBS was subtracted from the fluorescence values of the probe cleaved with purified MN prior to normalization.

Treatment of lyophilized Oligo-AuNPs with creek water or ocean water spiked with MN: Oligo-AuNPs were lyophilized using trehalose. To 200 µL of 0.5 nM Oligo-AuNPs was added 200 µL of 20 mg/mL trehalose leading to a final concentration of 10 mg/mL trehalose. The tip of a metal spatula was then heated with a bunsen burner and used to puncture the plastic cap of the eppendorf tube to create a hole. Filter paper was placed on the opening of the eppendorf tube before sealing with the cap. The Oligo-AuNPs within the eppendorf tube were then flash frozen using dry ice and ethanol and then lyophilized overnight. In order to determine the limit of detection of purified MN, the lyophilized Oligo-AuNPs were resuspended in 200 µL H$_2$O supplemented with 2 mM CaCl$_2$ and spiked with 10 µL of MN solution at various concentrations. In order to determine the limit of detection of MN in creek water or ocean water, lyophilized Oligo-AuNPs were reconstituted in either creek water or ocean water spiked with MN at various concentrations supplemented with 2 mM CaCl$_2$. Oligo-AuNPs were vortexed then incubated in a 37° C. water bath for 5 minutes. The color of the solution was noted. 95 µL of Oligo-AuNPs were loaded into a 96-well plate and the UV absorbance was measured using a plate reader (400 nm-700 nm).

Bacterial Cultures and Growth Conditions: Culture broth was inoculated from frozen stocks of each of the indicated bacterial species. *S. pneumoniae* was grown in 5 mL of TSB supplemented with 0.3% yeast extract; the tubes were capped to minimize airflow (anaerobic conditions). *A. baumannii* was grown in 5 mL of nutrient broth in aerobic conditions. *S. aureus* and *S. epidermidis* were grown in TSB (no yeast extract) in aerobic conditions. Bacteria were grown overnight (~18 hours) at 37° C. with shaking at 200 RPM. The 5 mL cultures were centrifuged at 4000×g for 20 minutes to pellet the bacteria. The supernatants were then transferred to fresh conical tubes and refrigerated.

TABLE 8

Description of bacteria, strain, and media used.

| Bacteria | Strain | Media used |
|---|---|---|
| *Staphylococcus aureus* (*S. aureus*) | AH2600 | TSB |
| *Acinetobacter baumannii* (*A. baumannii*) | *A. baumannii* 3.3 | Nutrient Broth |
| *Streptococcus pneumoniae* (*S. pneumoniae*) | AH1102 | TSB with 0.3% yeast extract |
| *Staphylococcus epidermidis* (*S. epidermidis*) | AH2490 | TSB |

Immunoblotting: Protein concentration in the various bacterial supernatants and TSB was determined by the BCA Protein Assay Kit. Equal amounts of protein (20 µg) were loaded on a precast Any KD Mini-PROTEAN TGX gel followed by transfer onto nitrocellulose. Membranes were blocked for 1 hour at 4° C. with 5% milk in Tris-buffered saline containing 0.1% Tween 20. The sheep anti-DNase IgG conjugated to horseradish peroxidase diluted 1:5000 in 5% milk and incubated with the membrane at room temperature for 1 hour. Immunoblots were quantified using Image J.

Treatment of Oligo-AuNPs using Bacterial supernatants: 1 mL of 0.5 nM Oligo-AuNPs was used in the cleavage experiments. 100 µL of supernatants from *S. aureus*, *A. baumannii*, *S. pneumoniae*, *S. epidermidis*, and TSB were used. The treated Oligo-AuNPs were vortexed quickly and then 20 μL of 100 mM $CaCl_2$ was added to reach a final concentration of 2 mM $CaCl_2$. The Oligo-AuNPs were then vortexed and quickly spun-down using a tabletop centrifuge to bring down residual liquid on the sides of the eppendorf tube. They were then incubated in a 37° C. water bath for 5 minutes. The color of each solution was noted. UV absorbance and DLS measurements were then taken. Oligo-AuNPs were then centrifuged at 16,000×g for 20 minutes. The supernatant was collected and placed into a new eppendorf tube. This was repeated 2 more times to ensure that there were no AuNPs in solution. The supernatant was then placed into a speed vacuum overnight at 45° C. 100 μL of $H_2O$ was added to each eppendorf tube and vortexed several times. The tubes were spun down quickly in a tabletop centrifuge to bring down residual liquid on the sides of the eppendorf. The solutions were then filtered through a 0.2 um filter and run on the LC-MS. The Oligo-AuNP pellet was resuspended into 250 μL of $H_2O$ and vortexed. 3 μL of treated Oligo-AuNPs were then loaded onto a 300-mesh copper grid for TEM imaging.

Example 2

Synthesis and Characterization of Oligo-AuNPs

Gold nanoparticles (AuNPs) are an attractive platform since they possess physical and optical properties that make them excellent candidates for colorimetric biosensors. AuNPs have a surface plasmon resonance (SPR) that is influenced by size, geometry, ligand and proximity to other nanoparticles. Due to this, nanoparticle aggregation results in a shift in SPR related absorption (~520 nm to ~650 nm) causing a colorimetric change in solution from red to purple.

By functionalizing AuNP with oligonucleotides, this new platform is able to provide a rapid, visually-definitive result that requires no extraneous instrumentation. This oligonucleotide-functionalized gold nanoparticles (Oligo-AuNP) platform can be used in potential applications in the clinic as well as in evaluating water sources in developing countries.

Contraction of *Staphylococcus aureus* (*S. aureus*) infections are oftentimes hospital-acquired. Patients that have weakened immune systems, surgical wounds, or invasive medical devices (urinary catheters, feeding tubes, breathing intubation, or intravascular catheters) are most at risk of contracting a staph infection. Other sources of infection can be from contaminated food and water sources. The diagnosis of *S. aureus* infections oftentimes requires biopsy with further culturing. This delay allows the bacterial infection to progress and can place patients in life-threatening situations (i.e. sepsis, endocarditis, osteomyelitis, toxic shock syndrome, and pneumonia).[3,11] Strides have been made in using LC-MS/MS to detect *S. aureus* using 15N metabolically labeled bacteriophage amplification and PCR to amplify a sequence of the nuc gene in serum samples.[9,10] Though these techniques are highly sensitive and quantitative, they are expensive and time intensive methods that are not ideal for testing in remote locations. Since current diagnostic procedures require hours to several days, there is an imminent need to create a point-of-care diagnostic platform that is rapid as well as sensitive, simple, and cost-effective.

Oligonucleotide-functionalized gold nanoparticles (Oligo-AuNPs) are an attractive platform since they possess physical and optical properties that make them excellent candidates for colorimetric biosensors.[13] AuNPs have a surface plasmon resonance (SPR) that is influenced by size, geometry, ligand and proximity to other nanoparticles. Due to this, nanoparticle aggregation results in a shift in SPR related absorption (~520 nm to ~650 nm) causing a colorimetric change in solution from red to purple.[14,15] The color change seen in solution during the aggregation of AuNPs provides the grounds for a practical platform for biosensing. AuNPs modified with oligonucleotides can be manipulated by enzymatic reactions allowing particles to assemble or disassemble.[3,9,10,11,13,14,15,18] Early work on oligonucleotide-functionalized AuNPs was pioneered by Mirkin and coworkers who created crosslinked networks of AuNP aggregates using complementary thiol-modified oligonucleotide strands to monitor endonuclease activity.[18,19] In the presence of DNAse I, these hybridized oligonucleotides were cleaved, causing the aggregate to disperse into single particles which allowed the solution to change from purple to red.[18] Mirkin and coworks have also used oligo-functionalized AuNPs for the detection of Hg2+ in rivers and lakes. This platform relies on the thymidine-Hg2+-thymidine coordination chemistry. The two thiolated DNA sequences used are complementary except for a thymidine-thymidine mismatch allowing the Hg2+ to selectively bind to the T-T mismatched site. Aggregates are formed in the presence of Hg2+ causing the solution to change in color from red to purple.[19] Other investigators, such as Liu and Lu have created a Pb2+ detection system using the "8-17" DNAzyme and its substrate to form AuNP aggregates. In the presence of Pb2+, the DNAzyme strand cleaves the substrate strand resulting in a color change from purple to red.[20] Li and coworkers have also created model colorimetric biosensors for the detection of enzymatic cleavage by DNase I and "8-17" DNAzyme. In this system, particles were functionalized with a S1 oligonucleotide strand, treated with 6-mercaptohexanol, then hybridized with the S2 strand. In the presence of DNase I, the DNA duplex is cleaved destabilizing the AuNPs, allowing the solution to change from red to purple. Their Pb2+ biosensor had a DNA substrate conjugated to AuNPs, followed by 6-mercaptohexanol treatment, then hybridization with the "8-17" DNA enzyme strand. In the presence of Pb2+, the substrate strand is cleaved causing a red-to-purple color change in solution.[21] These examples of oligonucleotide-functionalized AuNPs as biosensors exhibit how AuNPs can be easily used to create a rapid and simple diagnostic.

Recently, McNamara and coworkers have developed a quenched fluorescent bacterial imaging probe that is species specific towards *S. aureus*.[11] It is based on the enzymatic activity of microccal nuclease (MN) secreted by *S. aureus*.[40] The probe consists of 2'O-methylated chemically modified oligonucleotides with an unmodified pair of deoxythymidines in the center of the sequence and a fluorophore and quencher on either ends. The chemical modifications render it resistant to mammalian serum nucleases. In the presence of MN, the oligonucleotide strand is cleaved between the unmodified deoxythymidines, producing a fluorescent signal within 15 minutes and having a limit of detection at 0.05 units/μL.[11]

Based on this technology, Applicants decided to implement this oligonucleotide sequence and conjugate it onto a AuNP. In the presence of MN, the oligonucleotides are cleaved off of the AuNPs causing the individual particles to aggregate together. The aggregation phenomenon causes a red-to-purple color change within 5 minutes and is specific towards *S. aureus*. By functionalizing the probe onto a AuNP, this new platform is able to provide a rapid, visually-definitive result that requires no extraneous instrumentation. This oligonucleotide-functionalized gold nanoparticles (Oligo-AuNP) platform can be used in potential applications in the clinic as well as in evaluating water sources in developing countries.

Applicants have functionalized gold nanoparticles with an 11-mer oligonucleotide (5'-mCmUmCmGTTmCmGmU-mUmC-3' (SEQ. ID. NO:1)) that has been chemically modified to have 2'O methylations on all bases except for the two thymidines in the center. Enzymes within the body are not able to recognize the chemical modifications on the Oligonucleotide and will not cleave it, however, bacterial nucleases are able to digest chemically modified oligonucleotides. These functionalized gold nanoparticles are stable and red in solution, however, when it comes in contact with nuclease secreted by *S. aureus*, the oligonucleotide is cleaved causing particles to aggregate and undergo a colorimetric change in solution from red to purple. Detection of micrococcal nuclease secreted by *S. aureus* is rapid.

Applicants have also tested the AuNPs using various other bacterial supernatants such as *S. Epidermidis*, *S. pneumoniae*, *S. aureus*, and *A. baumannii*. A color change is only exhibited for some *S. Aureus* supernatant conditions.

Figure 19A:
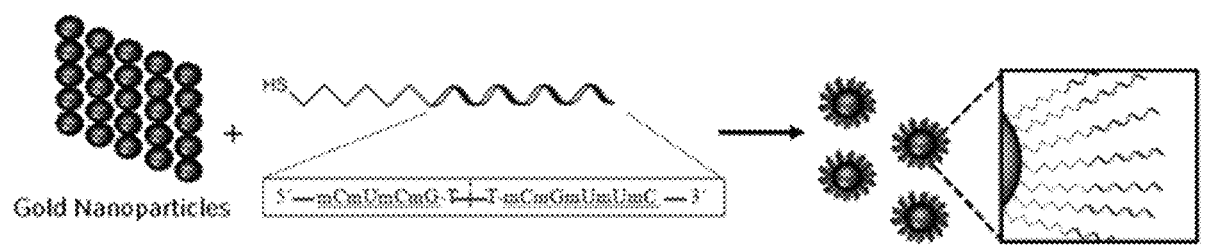
FIG. 19A-19C. Shows 20 nm AuNPs that were functionalized by using 5000 excess of oglionucleotides to AuNPs. AuNPs underwent a 5 hour salt aging process.
Figure 19B:
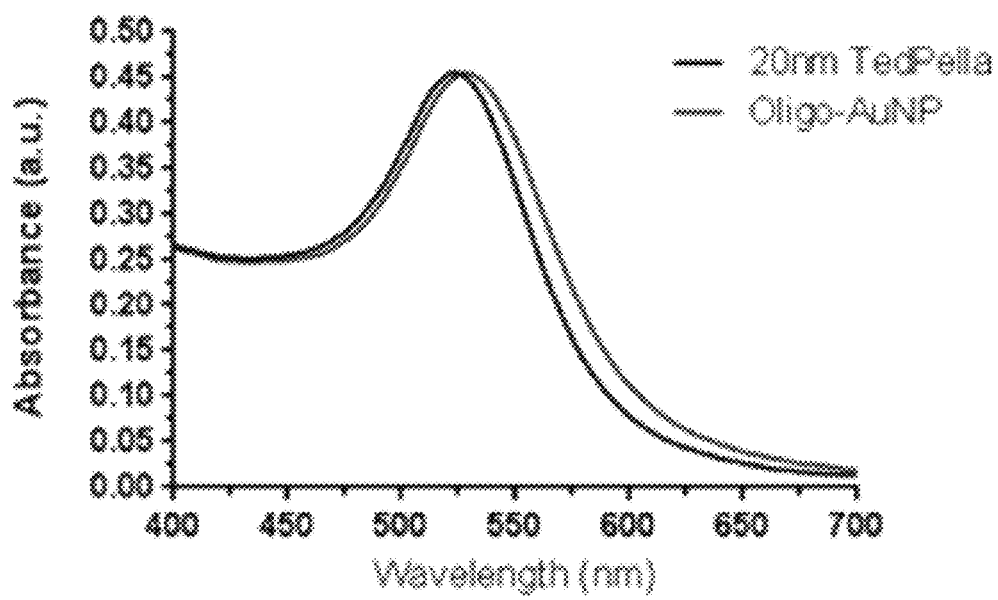
Figure 19C:
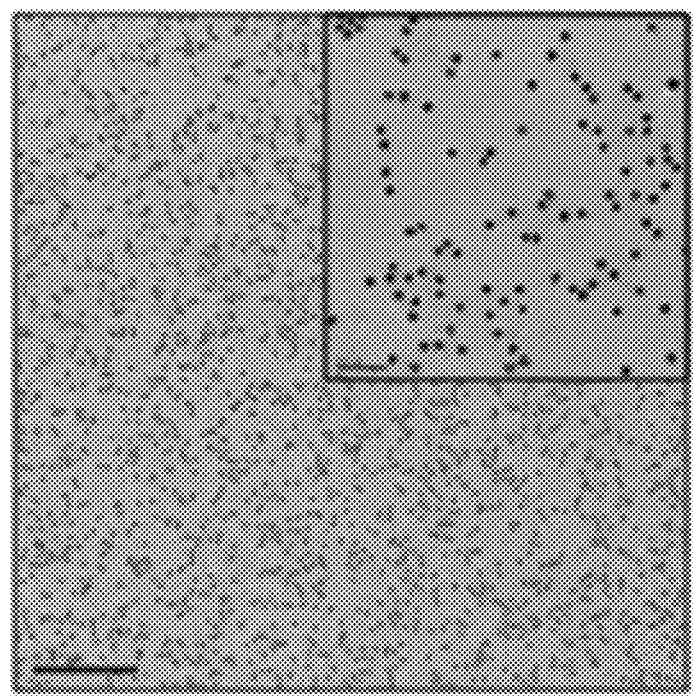
Figure 20:
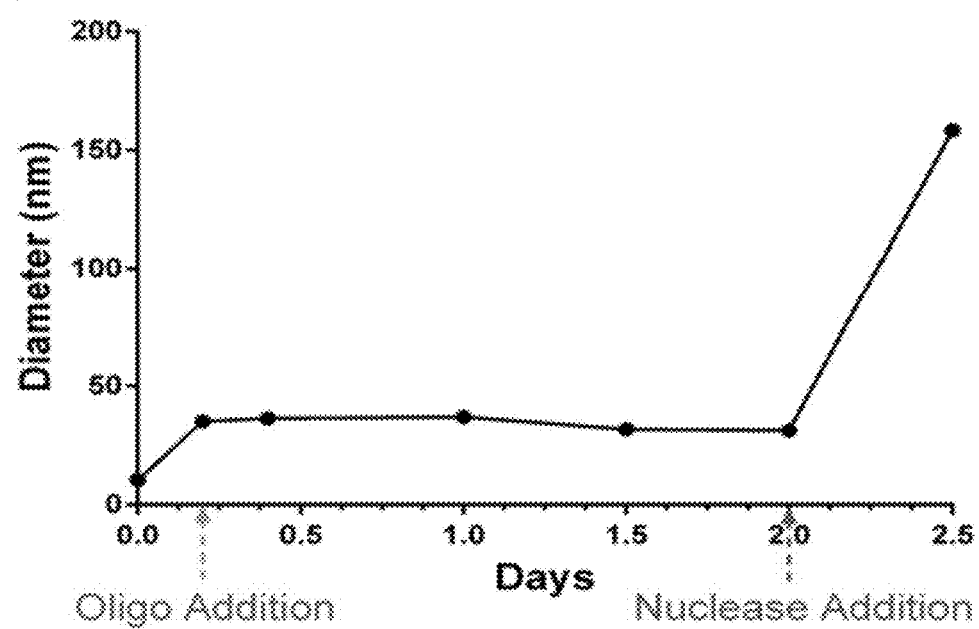
FIG. 20. 5 nm Oligo-AuNPs are stable until micrococcal nuclease addition, whereupon the aggregation occurs.
Figure 21:
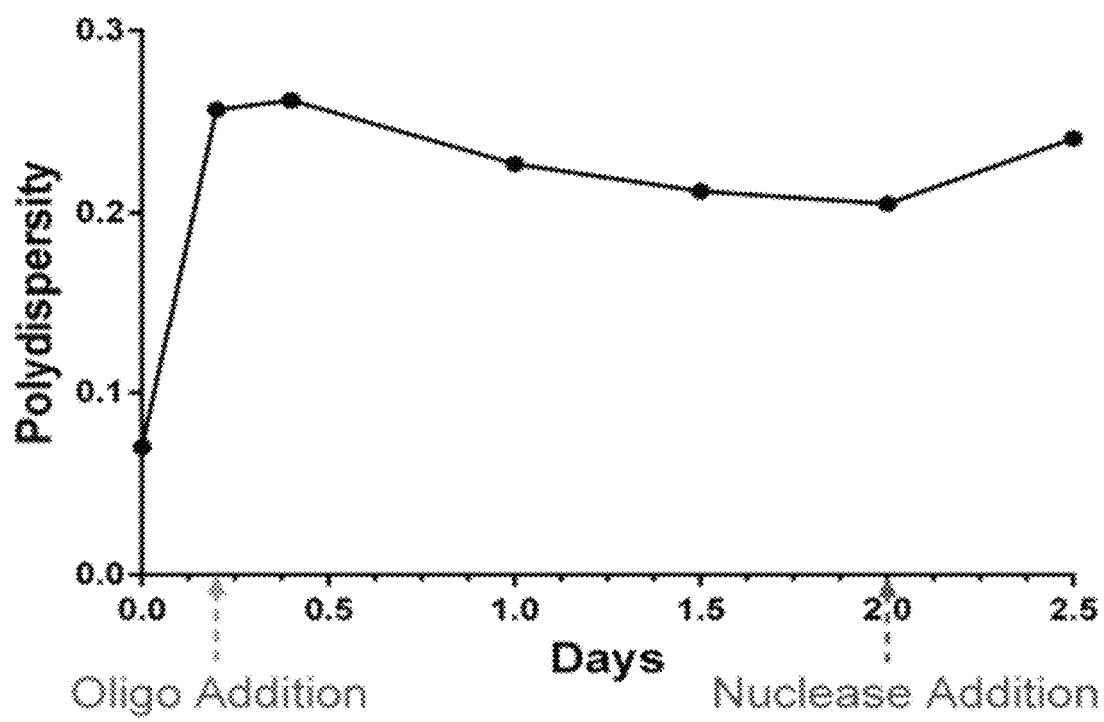
FIG. 21. the combination of oligonucleotide functionalization and salting-in results in high polydispersity index for the AuNPs.
Figure 22A:
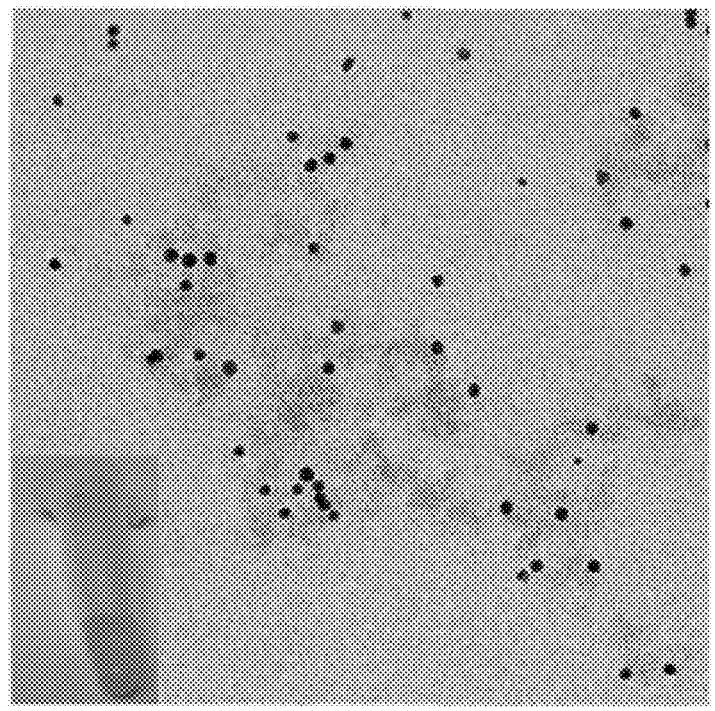
FIG. 22A-22B.
Figure 22B:
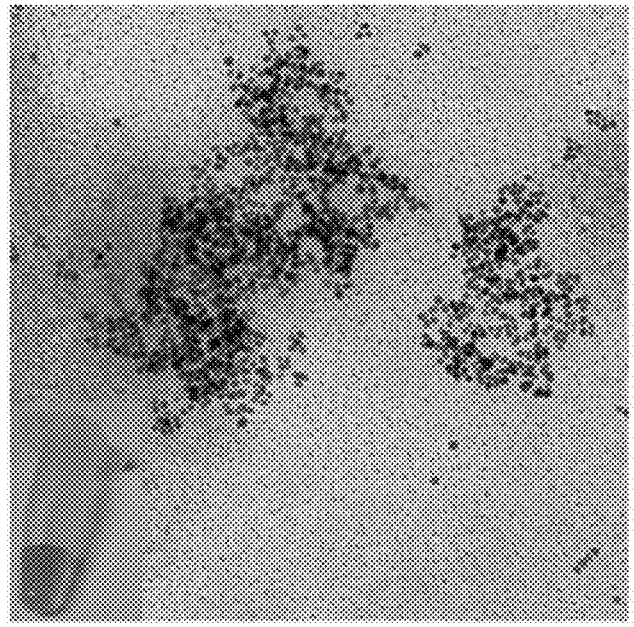
Figure 23:
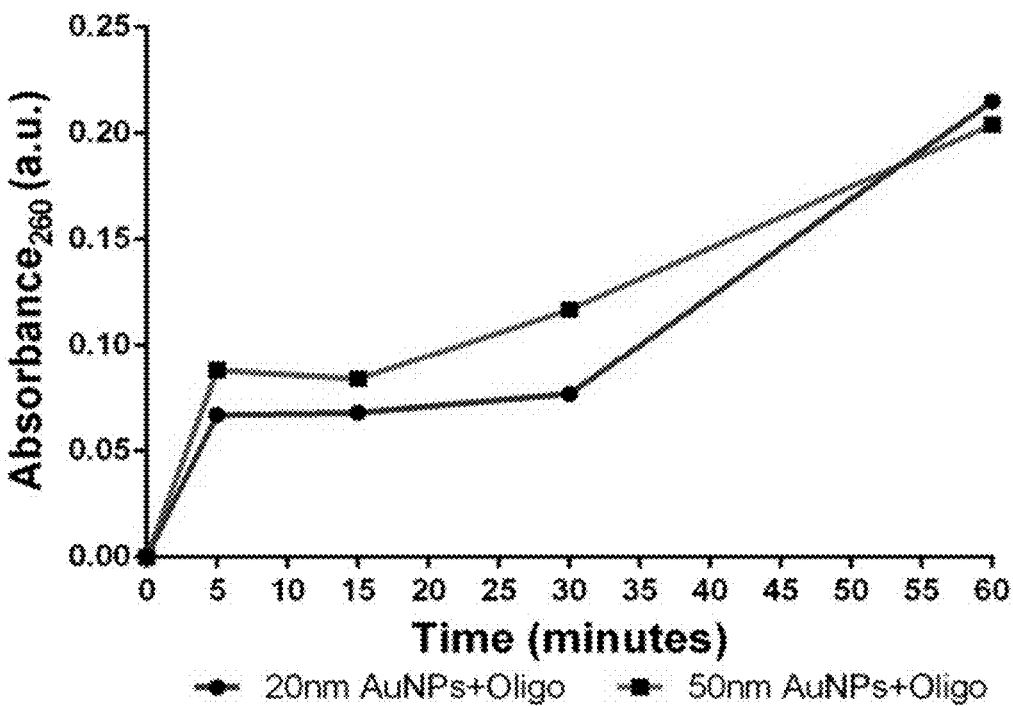
FIG. 23. An increase in oligonucleotide displacement of AuNPs is seen over time, as measured by DTT Displacement.
Figure 24:
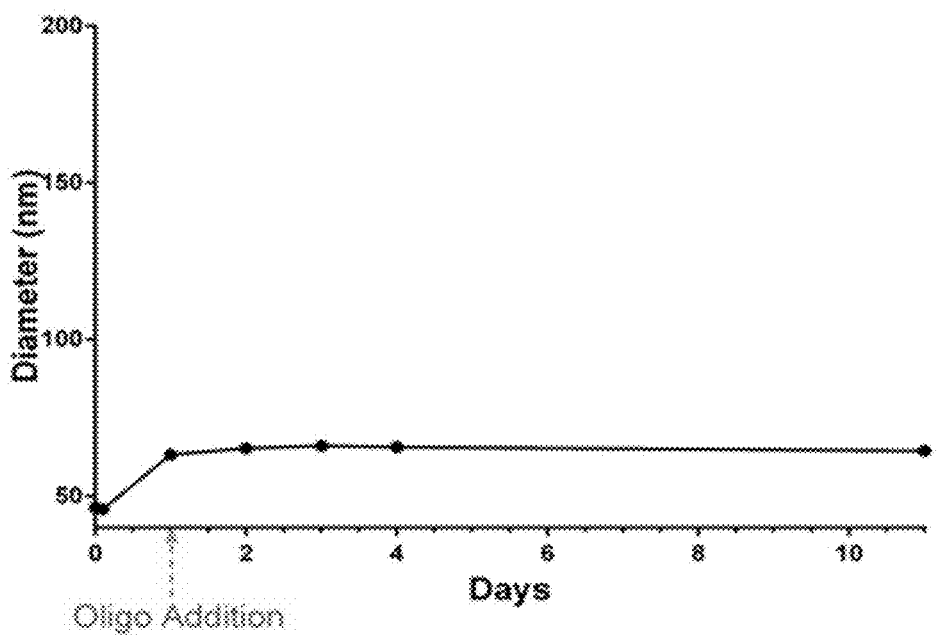
FIG. 24. Shows the stability of 50 nm Oligo-AuNPs over time.
Figure 25:
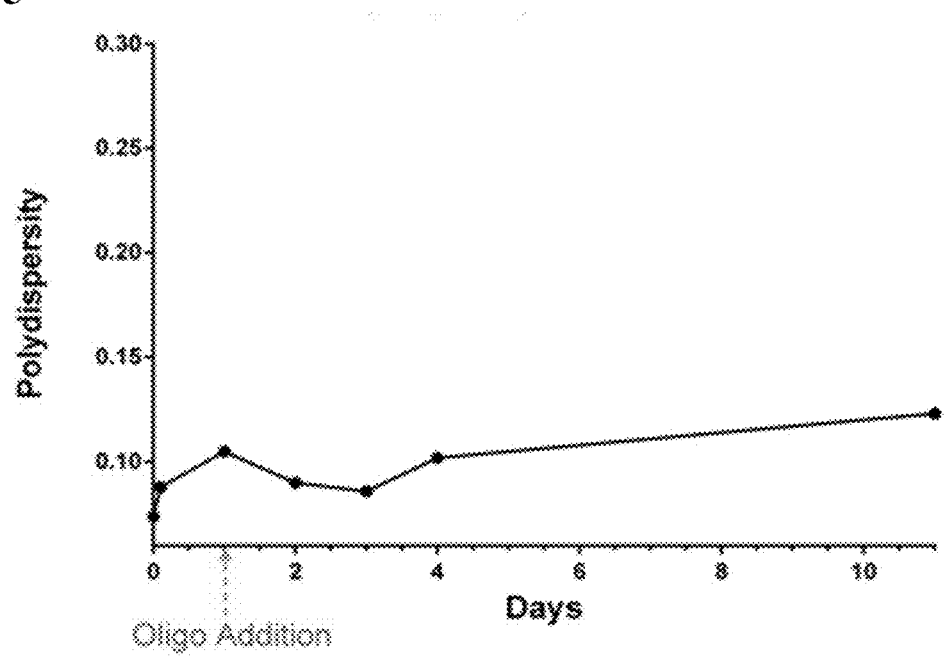
FIG. 25. The polydispersity of the 50 nm Oligo-AuNPs over time.
Figure 26A:
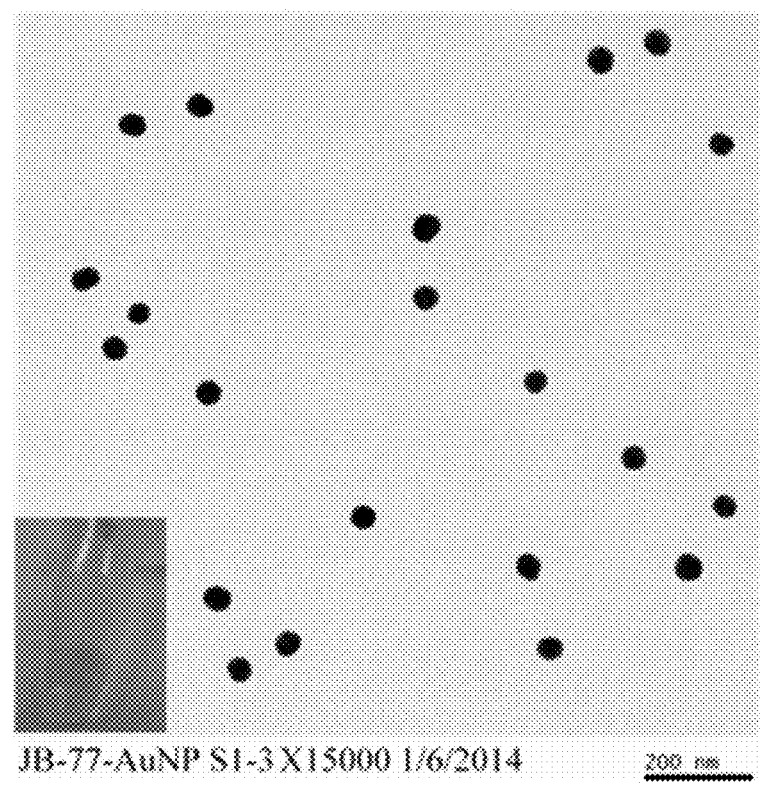
FIGS. 26A-26B. TEM Images of 50 nm Oligo-AuNPs.
Figure 26B:
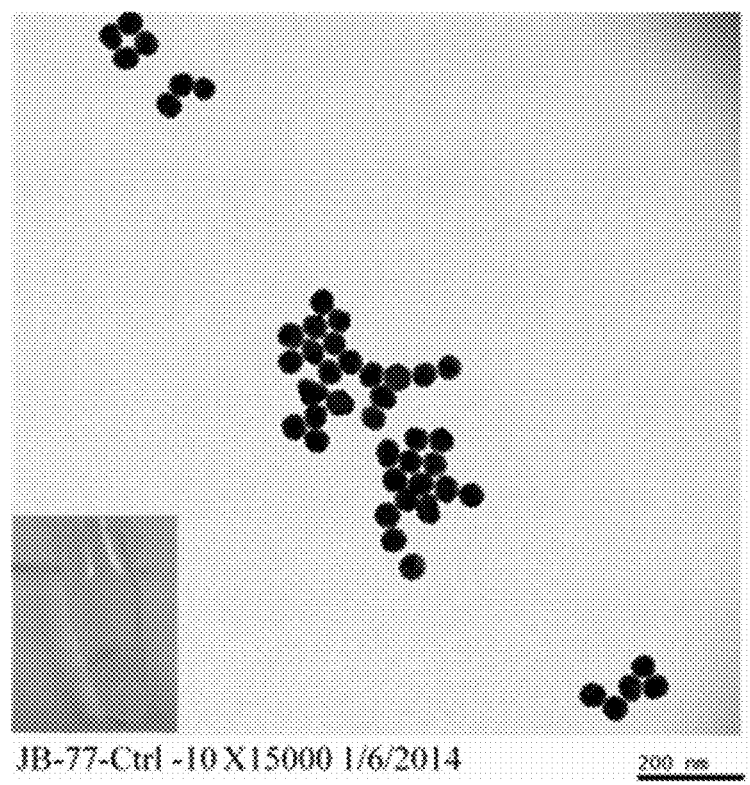
Figure 27:
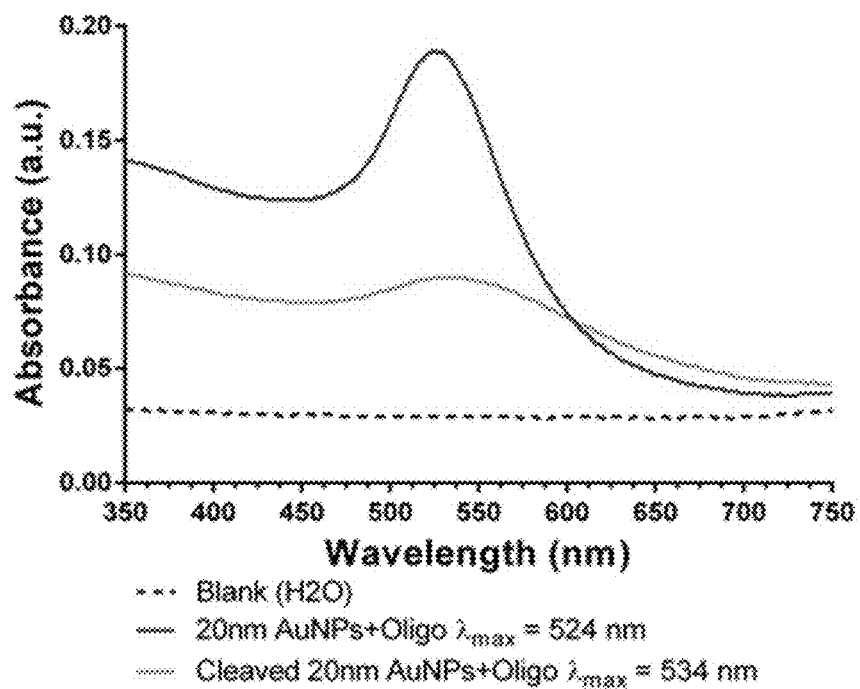
FIG. 27. The UV-Vis spectra of 20 nm AuNPs. The surface plasmon wavelength is shifted to the right when oligo-functionalized 20 nm AuNPs are cleaved.

Oligonucleotides were reduced with 100 mM DTT and 100 mM $NaHCO_3$ for 1 hour. DTT was removed through spin filtration. The oligonucleotides (58.12 nmol, 1 mL) were then added to the 20 nm AuNPs (0.0116 nmol, 10 mL) at 5,000× excess. AuNPs were allowed to incubate on a tabletop shaker overnight. AuNPs then underwent a 5 hour salt-aging process and were incubated on a tabletop shaker overnight. In order to remove unbound oligonucleotides, AuNPs were centrifuged at 16,000×g for 20 minutes and washed 3× with H2O. The Oligo-AuNPs were then diluted with H2O so that the stock concentration was 0.5 nM. The Oligo-AuNPs had an UV absorbance at 530 nm and were 33.8 nm in diameter as seen in FIG. 21B and Table 9. In FIG. 19C, TEM images show Oligo-AuNPs to be monodisperse after functionalization as seen. The zeta potential measurements gave a value of −20.65. In order to determine the amount of oligonucleotide on each AuNP, a DTT displacement protocol was used according to a protocol previously reported by Mirkin and coworkers[41]. DTT (1 M) in 0.18 M (pH=8) was used to displace the oligonucleotides on 500 μL of AuNPs. The solution was transferred to a 3 k MWCO spin filter and washed 5× with H2O to remove the DTT. The solution was then placed into a speed vac for ~16 hours. The pellet was then dispersed in 50 μL of H2O and the UV absorbance was taken at 260 nm. The amount of oligonucleotide strands was then divided by the amount of AuNPs in 500 μL (529 strands per AuNP).

TABLE 9

Olgio-AuNPs that were characterized by DLS, Zeta, and DTT displacement to quantitate the number of oglionucleotide strands per AuNP. Characterization of Oligo-AuNPs

| | |
|---|---|
| DLS (avg) | 33.8 ± 0.665 nm |
| PDI (avg) | 0.031 ± 0.001 |
| Zeta | −20.65 ± 2.375 |
| Oligo/AuNP | 529 ± 13 strands |

The 11-mer oligonucleotide was first digested with purified micrococcal nuclease (MN) and RNase (negative control) and analyzed by LC-MS (Agilent 1100 HPLC/Agilent 6120 Mass Spectrometer). In FIG. 6A, there are many peaks present at 254 nm due to MN digesting the 11-mer into many different sized oligonucleotides in the presence of $CaCl_2$. In the absence of $CaCl_2$, MN was still able to digest the 11-mer and the primary peak seen was the cleaved 6-mer. The 11-mer was intact when treated with RNase A as seen in FIG. 6B. In the presence of EDTA, the 11-mer was undigested when treated with MN or RNase A both with and without $CaCl_2$. After demonstrating that the 11-mer is susceptible to cleavage by MN, the Oligo-AuNPs were then treated with 1 unit/μL of MN or 10 μg/mL of RNase A in addition to 2 mM $CaCl_2$. The Oligo-AuNPs were then incubated in a water bath at 37° C. for 5 minutes. The MN treated Oligo-AuNPs experienced a colorimetric change in solution from red to purple as well as a shift in absorbance from 530 nm to 570 nm as seen in FIG. 1B. The RNase A condition did not result in a color change and the UV absorbance remained at 530 nm.

Oligo-AuNPs detection using bacterial supernatants: 1 mL of AuNPs was used. 100 μL of supernatants from *S. aureus*, *A. baumannii*, *S. pneumoniae*, *S. epidermidis*, and TSB were used. The treated Oligo-AuNPs were vortexed quickly and then 22 μL of 100 mM $CaCl_2$ was added to reach a final concentration of 2 mM $CaCl_2$. The Oligo-AuNPs were then vortexed and quickly spun-down using a tabletop centrifuge. They were then incubated in a 37° C. water bath for 5 minutes. The color of each solution was noted. UV absorbance and DLS measurements were then taken. Oligo-AuNPs were then centrifuged at 16,000×g for 20 minutes. The supernatant was collected and placed into a new eppendorf tube. This was repeated 2 more times to ensure that there were no AuNPs in solution. The supernatant was then placed into a speed vac. overnight at 45° C. 100 μL of H2O was added to each eppendorf tube and vortexed several times. The tubes were spun down quickly in a tabletop centrifuge to bring down residual liquid on the sides of the eppendorf. The solutions were then filtered through a 0.2 um filter and ran on the LC-MS. The Oligo-AuNP pellet was resuspended into 250 μL of H2O (one spin down is enough to get rid of the excess salt and broth) and vortexed. 3 μL of treated Oligo-AuNPs were then loaded onto a 300-mesh copper grid for TEM imaging.

Oligo-AuNPs were then treated with the various bacterial supernatants and monitored. After 5 minutes, the *S. aureus* supernatant condition experienced a color change from red to purple as well as a shift in absorbance from 530 nm to 570 nm as seen in FIGS. 5A and 5B. The broth and the other bacterial supernatants used to treat Oligo-AuNPs remained red in solution and did not shift in UV absorbance. In FIG. 5C, DLS showed a drastic increase in diameter when Oligo-AuNPs are treated with *S. aureus* supernatant. By TEM, Applicants see mass aggregation of Oligo-AuNPs when treated with *S. aureus* supernatant, whereas the other bacterial supernatant conditions remain monodisperse as seen in FIG. 5D. Oligo-AuNPs treated with bacterial supernatants were further allowed to incubate for 1 hour before centrifuged to pellet the AuNPs. The supernatant was then transferred to a new eppendorf tube and centrifuged (repeated twice) to remove AuNPs. A dilution study was also done on the Oligo-AuNPs to determine the minimum volume of *S. aureus* supernatant needed to cause a colorimetric change in solution and cleavage in FIGS. 16A and 16B. A minimum of 10 μL of *S. aureus* supernatant caused a colorimetic change in solution and a shift in absorbance.

Figure 12A:
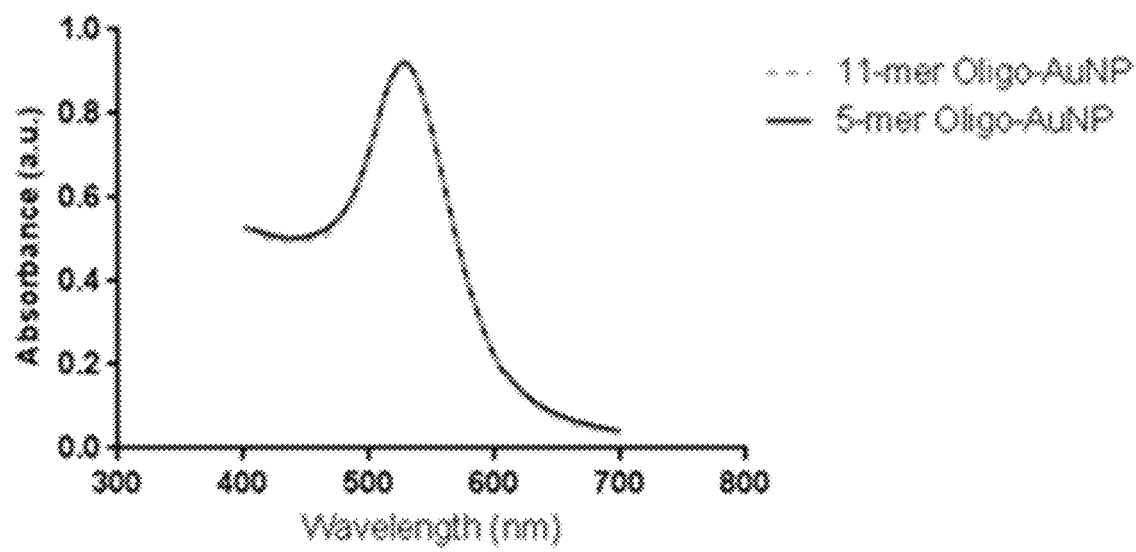
FIGS. 12A-12C.
Figure 12B:
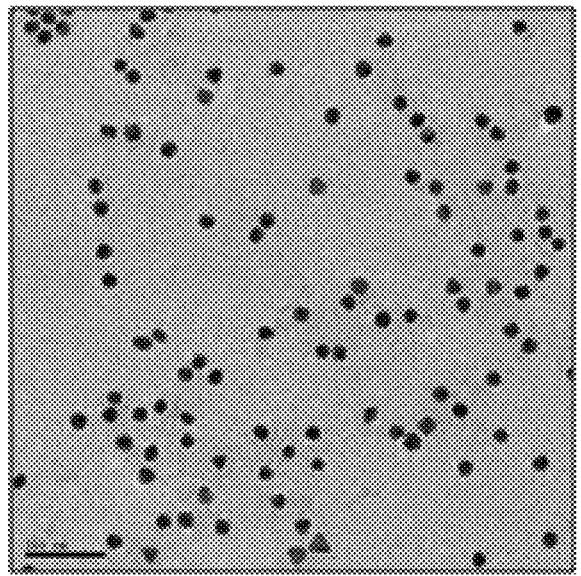
Figure 12C:
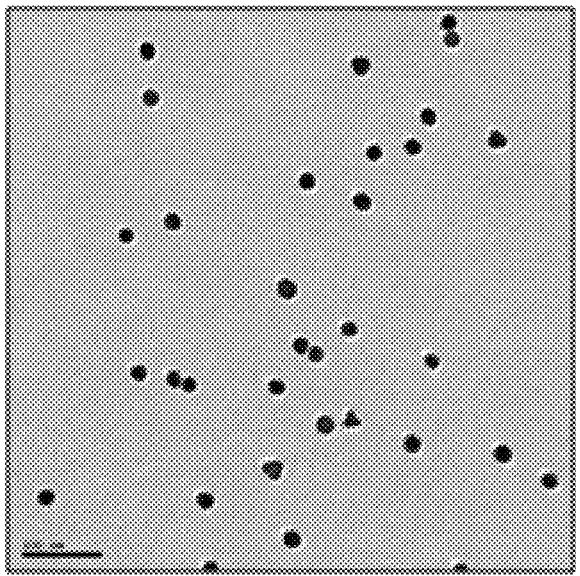

In the presence of MN, the 11-mer oligonucleotide is cleaved on the Oligo-AuNPs and the 6-mer oligonucleotide is dispersed in solution. However, the 5-mer oligonucleotide remains on the Oligo-AuNP. This led us to investigate how the Oligo-AuNPs were aggregating despite having 5-mers attached to the surface of the AuNPs. AuNPs were functionalized with a thiolated 5-mer oligonucleotide. The UV absorbance of the 11-mer and 5-mer Oligo-AuNPs were equivalent (530 nm) as seen in FIG. 12A. By TEM, the 5-mer Oligo-AuNPs were seen to be monodisperse, suggesting that oligonucleotides as small as a 5-mer can act as colloidal stabilizers. In FIG. 12B and Table 10, the diameter of the 5-mer Oligo-AuNPs was measured by DLS to be 30.73 nm. Through DTT displacement, the 5-mer Oligo-AuNPs were discovered to have more strands of oligonucleotides (823 strands/AuNP) on its surface compared to the 11-mer Oligo-AuNPs (529 strands/AuNP). This is due to the fact that the 5-mer has a smaller footprint (0.153 nm$^2$) and is more tightly packed than the 11-mer oligonucleotide (0.238 nm$^2$) which was calculated by using an equation previously reported by Mirkin and coworkers. This suggests that there are unfilled gaps on the 11-mer Oligo-AuNPs in which particles can interact due to the decrease in interparticle electrostatic repulsions as the 11-mer is cleaved on the Oligo-AuNPs.

TABLE 10

Oligo-AuNPs were characterized by DLS, Zeta Potential, and DTT displacement. Both the 5-mer and 11-mer Oligo-AuNPs were equivalent in diameter and surface charge. However, there were more strands of oligonucleotides on the 5-mer Oligo-AuNPs compared to the 11-mer Oligo-AuNPs.

| Oligo-AuNP Comparison | 11-mer Oligo-AuNP | 5-mer Oligo-AuNP |
|---|---|---|
| DLS | 33.8 ± 0.665 nm | 30.73 ± 0.484 |
| PDI | 0.031 ± 0.001 | 0.100 ± 0.016 |
| Zeta Potential | −20.65 ± 2.375 | −17.34 ± 0.245 |
| Oligo/AuNP | 529 ± 14 strands | 823 ± 45 strands |

Figure 2C:
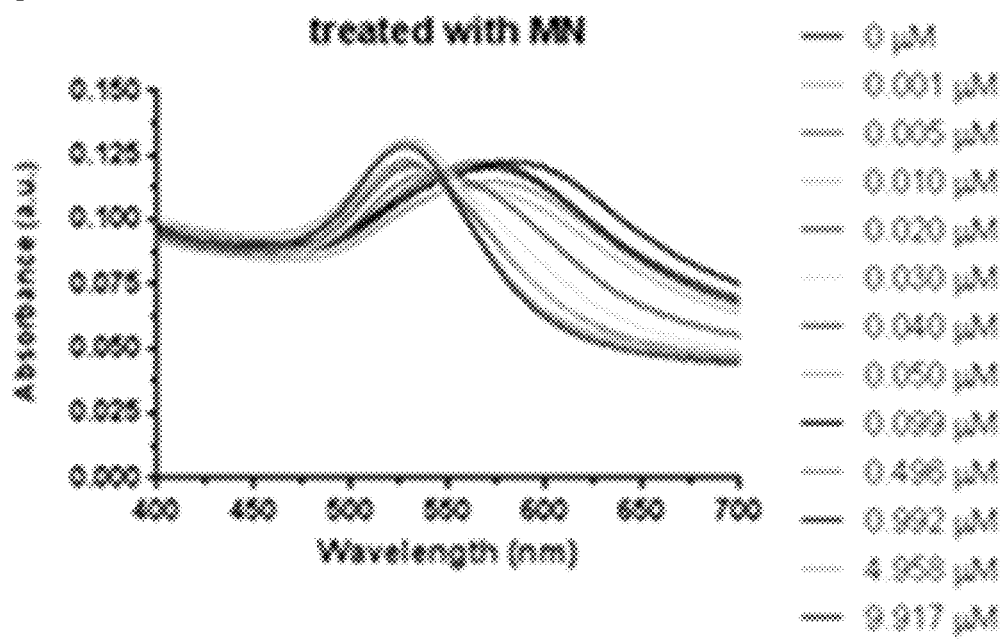
Figure 2D:
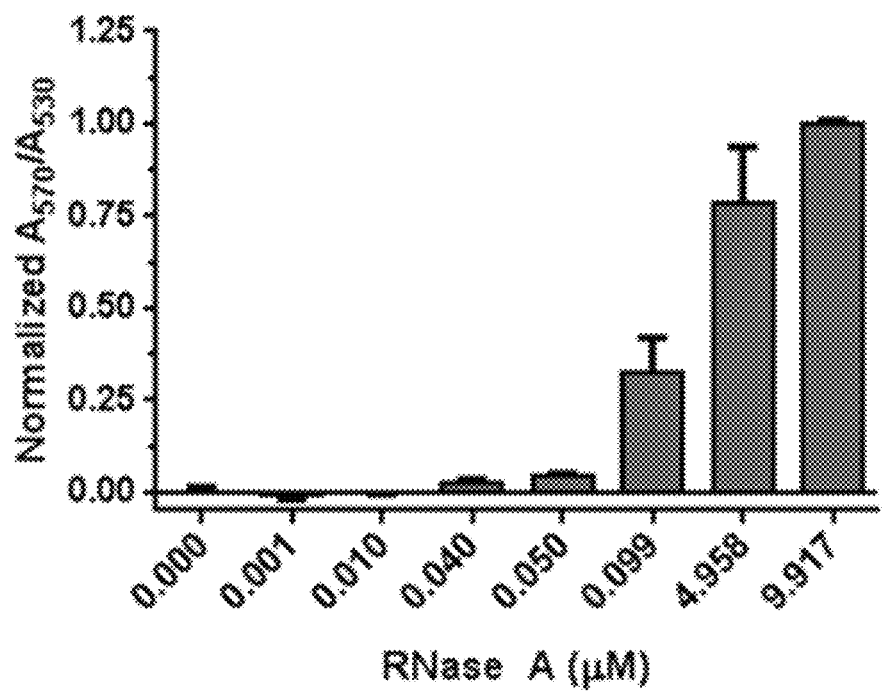
Figure 2E:
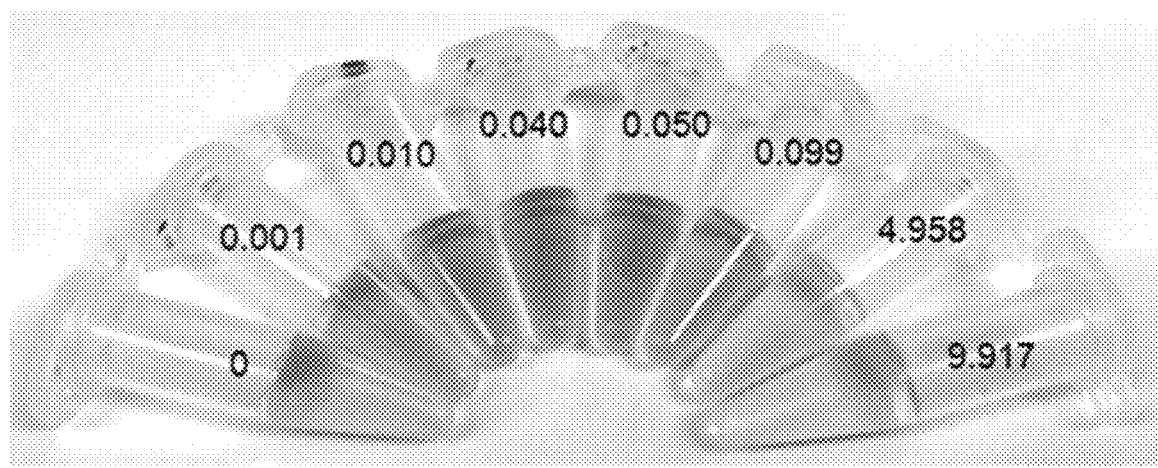
Figure 2F:
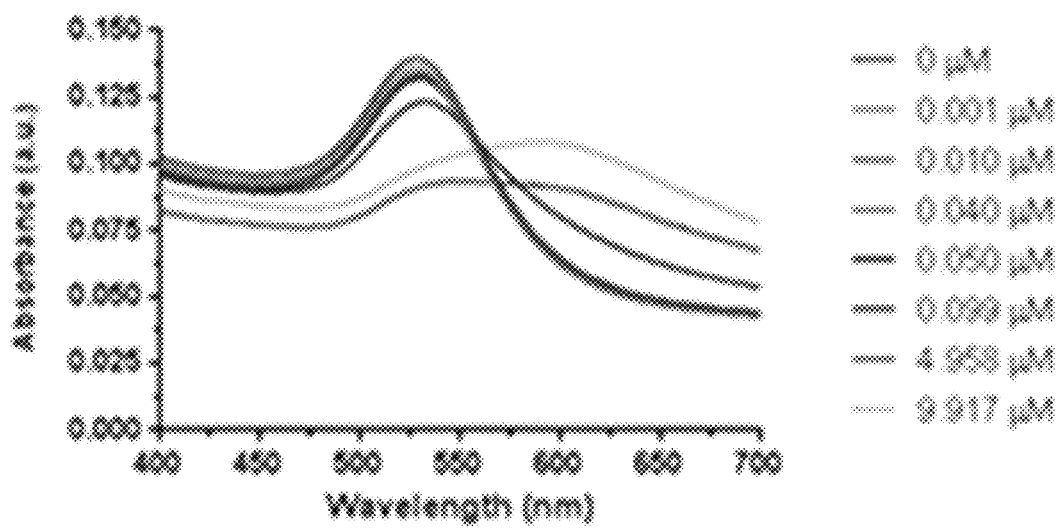

In FIGS. 2C and 2D, the sensitivity of the Oligo-AuNP biosensor was determined to have a limit of detection of 0.01 units/µL. The specificity of cleavage and limit of detection of the quenched fluorescent 11-mer probe was equivalent to the Oligo-AuNPs.

Statistics & Calculations: Results are shown as means. Error bars represent the SEM. Limit of detection was calculated by:

$$LOD \; (\text{unit}/\mu L) = 3.3 \times \left(\frac{\sigma}{S}\right)$$

$\sigma$ = Standard error of the regression line $S$ = slope

Footprint (K) was calculated by:

$$\text{Footprint} \; (nm^2/DNA) = \frac{4\pi r^2}{Nr}$$

$r$ = radius of AuNP $N$ = average number of oligonucleotides per AuNP

In order to develop this rapid diagnostic into a viable platform to be used in remote locations, Applicants looked into lyophilizing the Oligo-AuNPs. This would provide ease of use and transportation of the biosensor. Lyophilized Oligo-AuNPs were prepared according to a modified protocol previously reported by Stone and coworkers. Trehalose (20 mg/mL) was added to 200 µL of Oligo-AuNPs (0.5 nM) to obtain a final concentration of 10 mg/mL of trehalose. The mixture was then lyophilized overnight. In order to determine if lyophilized Oligo-AuNPs behaved similar to unlyophilized particles, a limit of detection study was conducted.

The examples have demonstrated the use of Oligo-AuNPs as a biosensor for MN secreted by S. aureus through enzymatic cleavage. In the presence of MN, the 11-mer oligonucleotide functionalized on 20 nm AuNPs is cleaved leaving behind a 5-mer oligonucleotide on the AuNP and the 6-mer displaced in solution. This results in aggregation of the particles and a colorimetric change from red to purple within 5 minutes. The Oligo-AuNPs are also specific to S. aureus supernatants and do not aggregate in supernatants from A. baumannii, S. pneumoniae, or S. epidermidis. The limit of detection of Oligo-AuNPs was 0.01 units/µL MN.

Applicants have also investigated a mechanism of aggregation and discovered that 5-mer Oligo-AuNPs (823 strands) have increasingly more strands of oligonucleotide compared to the 11-mer Oligo-AuNP (529 strands). This is due to the smaller footprint and reduced electrostatic repulsion of the 5-mer oligonucleotide compared to the 11-mer oligonucleotide. Since the 11-mer oligonucleotide functionalized on the Oligo-AuNPs are not as densely packed, this suggests that there are still empty gaps on the surface of the particle. As the 11-mer is cleaved, the 5-mer remains on the surface, however, this exposes the empty gaps on the surface of the Oligo-AuNPs and decreases the interparticle repulsion forces allowing aggregation to occur. This also suggests that a few cleavage events are necessary in order for instability and aggregation to occur.

Since AuNPs in solution tend to spontaneously aggregate when in extreme temperatures, Applicants have explored lyophilization of Oligo-AuNPs immersed in a cryoprotectant. By lyophilizing Oligo-AuNPs in trehalose, Applicants have demonstrated the functionality of lyophilized Oligo-AuNPs to be equivalent to unlyophilized Oligo-AuNPs. Sensitivity is conserved as well. This allows the Oligo-AuNPs to be transported with ease. Usage is also simplified as well since samples of interest can be used to directly re-suspend the lyophilized AuNPs. This platform has potential to be used clinically to diagnose patients and in developing countries as well for evaluating water quality. Similar strategies can be adopted to use the oligonucleotide substrate as a biosensor to target other enzymes secreted by bacteria of interest.

Example 3

Rapid Detection of Staph Bacteria Using Nanotechnology

*Staphylcoccus aureus* is a bacterium that causes nosocomial infections. There are more than 500,000 staph infections each year in the U.S. However, current methods for detection of staph bacteria delay diagnosis, allowing the progression of the infection to occur. Current diagnostics require 24 to 48 hours to culture bacteria, gram staining, and coagulase testing.

In order to address this challenge, oligonucleotide-functionalized gold nanoparticles (AuNPs) are utilized to create a diagnostic platform for the rapid detection of staph bacteria. This detection is based on the cleavage of the PEGylated-oligonucleotide by micrococcal nuclease secreted by staph bacteria. The loss of PEG causes the AuNPs to become unstable and agglomerate (Table 11). Due to the optical properties of gold nanoparticles, aggregation states can be visually identified leading to the definitive diagnosis of staph bacterial infections.

Figure 28A:
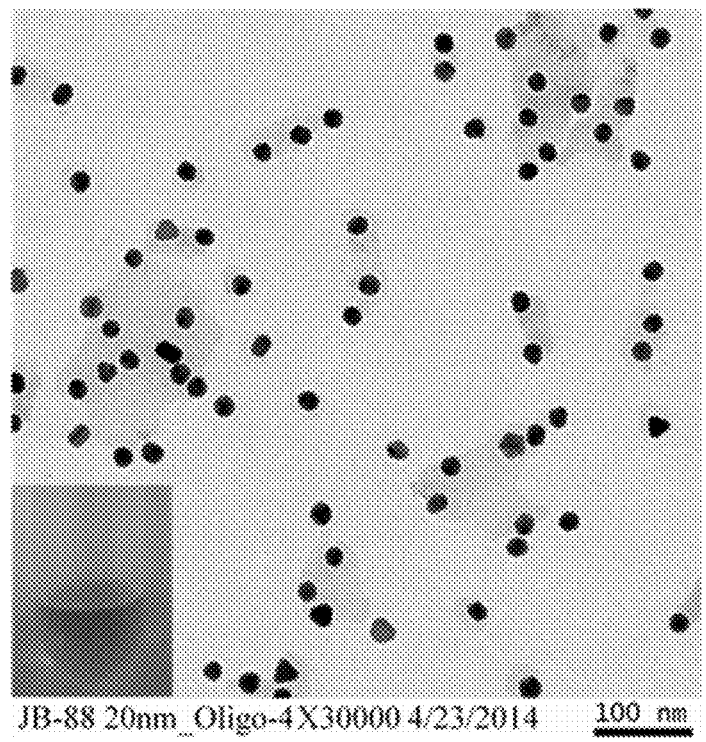
FIGS. 28A-28C. TEM images of oligo-functionalized 20 nm AuNPs.
Figure 28B:
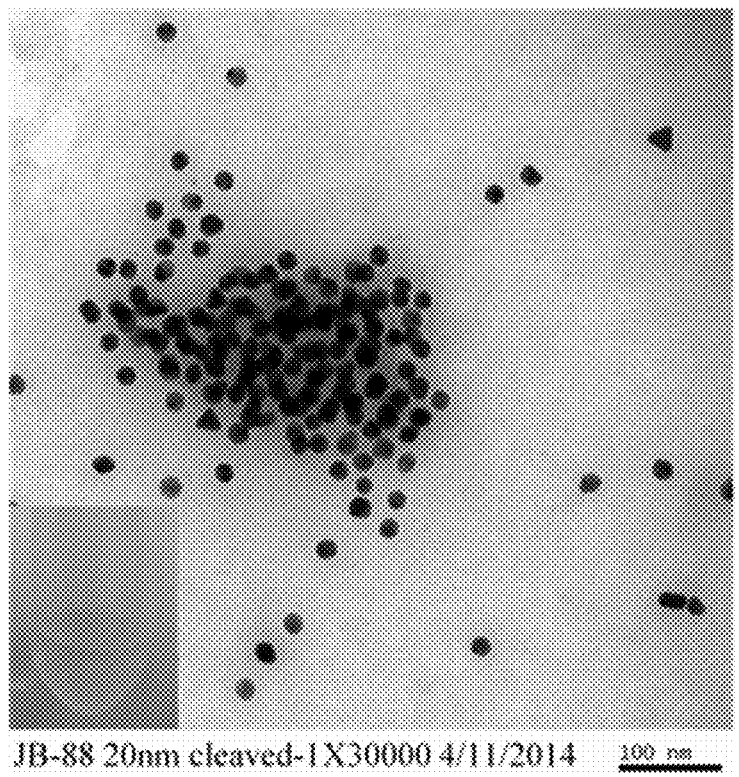
Figure 28C:
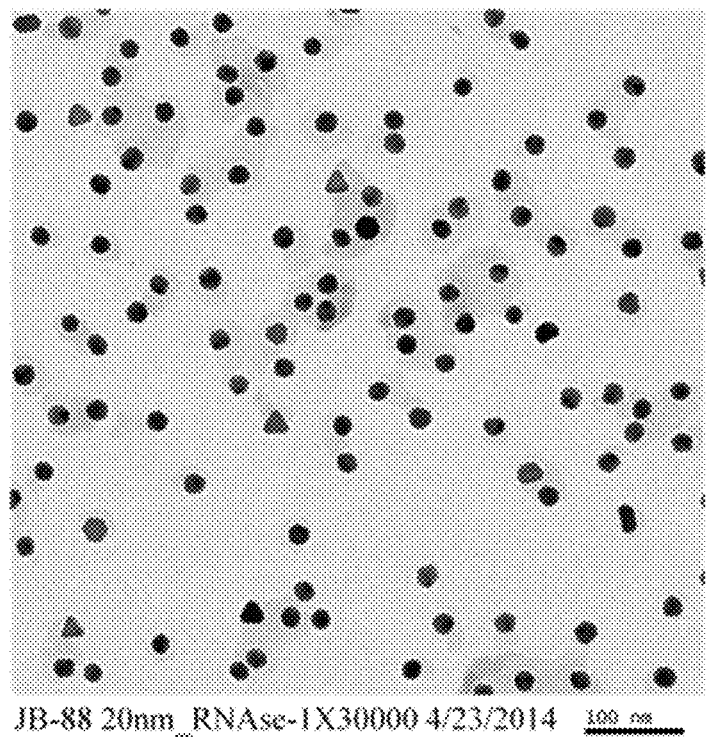
Figure 29:
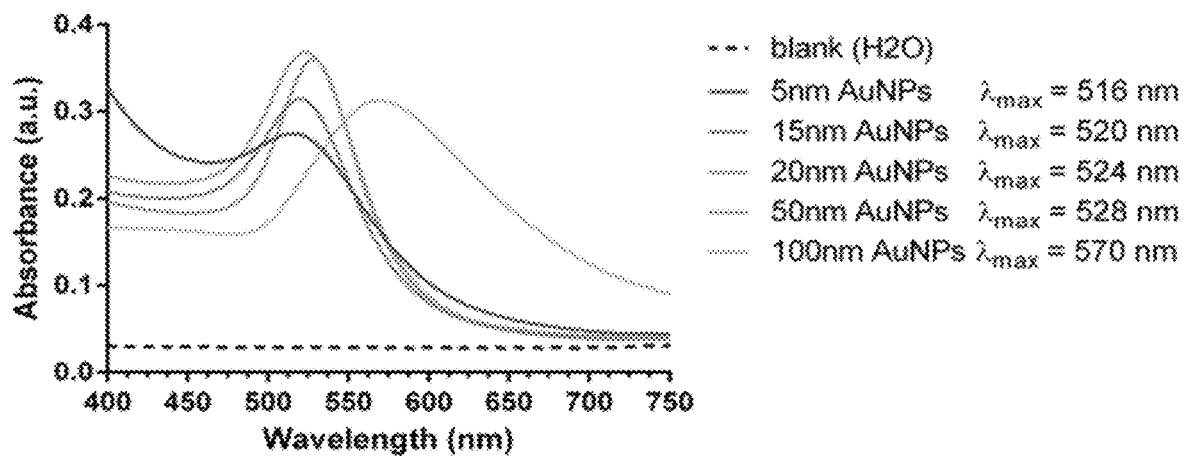
FIG. 29. UV-Vis Spectra of AuNPs of various Sizes. Optical properties of colloidal AuNPs are dependent on AuNP shape and size. As the diameter increases, the wavelength of the surface plasmon resonance related absorption shifts to the right.
Figure 30:
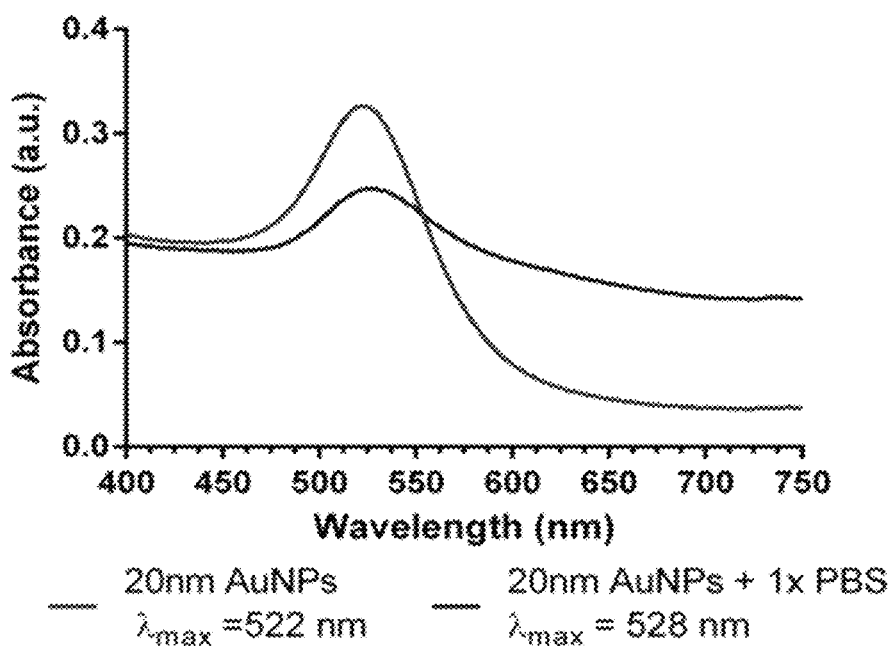
FIG. 30. Effect of Aggregation on Optical Properties of 20 nm AuNPs. AuNPs aggregate upon the addition of PBS, causing the surface plasmon resonance wavelength to shift to the right.
Figure 31:
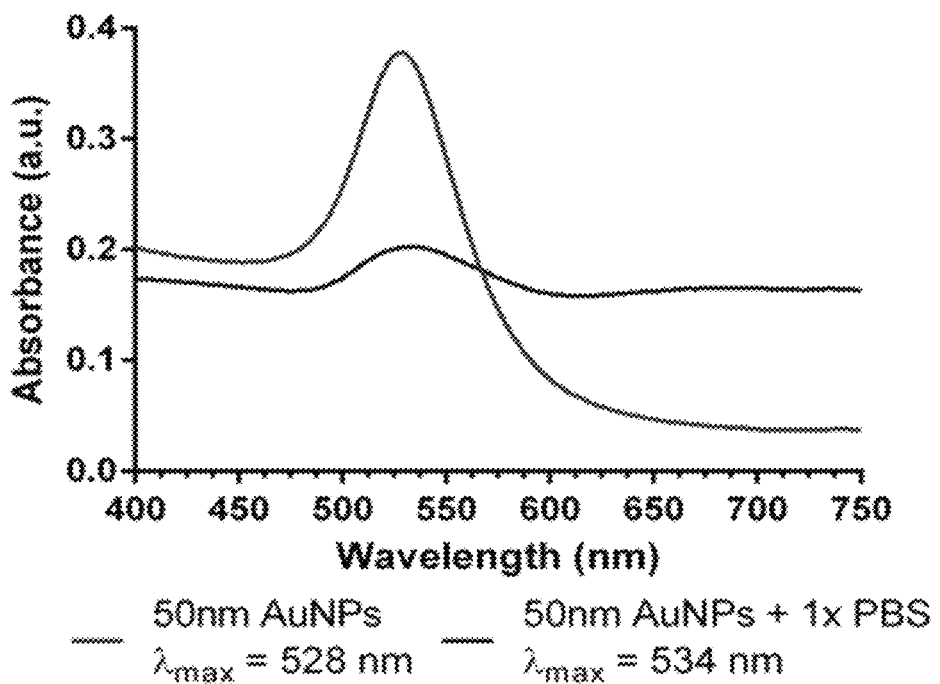
FIG. 31. Effect of Aggregation on Optical Properties of 50 nm AuNPs. AuNPs aggregate upon the addition of PBS, causing the surface plasmon resonance wavelength to shift to the right.

A variety of different sized AuNPs can be functionalized with the PEGylated oligonucleotide. Dynamic Light Scattering, Zeta Potential, and TEM results confirmed that the oligonucleotide coating allowed the oligo-AuNPs to remain in a monodisperse state, as seen in FIG. 19A, FIGS. 4J-4L, and FIGS. 24-33. Stability was seen up to 11 days with the 50 nm oligo-AuNPs, shown in FIGS. 28A and 28B.

TABLE 11

Bare AuNPs have a negatively charged surface due to citrate, whereas the Oligo-AuNPs are passivated by PEG, as measured by the Zeta Potential.

| Conditions | Mean Zeta Potential |
| --- | --- |
| 20 nm AuNP bare | −26.8 mV |
| 20 nm AuNP + Oligo | −8.74 mV |
| 50 nm AuNP bare | −27.9 mV |
| 50 nm AuNP + Oligo | −14.83 mV |

The oligo-AuNPs are specifically cleaved by the micrococcal nuclease as evidenced by a colorimetric change in solution, TEM images, and the UV/Vis spectra. This platform results in a simple colorimetric readout and effectively reduces detection time to 1 hour, which is highly advantageous compared to current methods that require 24-48 hours. These results serve as a proof-of-concept, demonstrating that this is a potential diagnostic platform for the detection of bacteria.

Informal Sequence Listing

```
SEQ ID NO: 1:
5' mCmUmCmGTTmCmGmUmUmC 3'
```

In SEQ ID NO:1 the symbol m is methyl.

REFERENCES (1) Marcheggiani, S.; D'Ugo, E.; Puccinelli, C.; Giuseppetti, R.; D'Angelo, A. M.; Gualerzi, C. O.; Spurio, R.; Medlin, L. K.; Guillebault, D.; Weigel, W.; Helmi, K.; Mancini, L. International Journal of Environmental Research and Public Health 2015, 12, 5505.

(2) Goodwin, K. D.; McNay, M.; Cao, Y.; Ebentier, D.; Madison, M.; Griffith, J. F. Water research 2012, 46, 4195.

(3) Spaulding, A. R.; Salgado-Pabon, W.; Kohler, P. L.; Horswill, A. R.; Leung, D. Y.; Schlievert, P. M. Clinical microbiology reviews 2013, 26, 422.

(4) Viau, E. J.; Goodwin, K. D.; Yamahara, K. M.; Layton, B. A.; Sassoubre, L. M.; Burns, S. L.; Tong, H. I.; Wong, S. H.; Lu, Y.; Boehm, A. B. Water research 2011, 45, 3279.

(5) Griffith, J. F.; Cao, Y.; McGee, C. D.; Weisberg, S. B. Water Res 2009, 43, 4900.

(6) Goodwin, K. D.; Pobuda, M. Water Res 2009, 43, 4802.

(7) Brakstad, O. G.; Maeland, J. A.; Chesneau, O. APMIS: acta pathologica, microbiologica, et immunologica Scandinavica 1995, 103, 219.

(8) Lachica, R. V. F.; Hoeprich, P. D.; Genigeorgis, C. Applied Microbiology 1972, 23, 168.

(9) Pierce, C. L.; Rees, J. C.; Fernandez, F. M.; Barr, J. R. Molecular & cellular proteomics: MCP 2012, 11, M111 012849.

(10) Brakstad, O. G.; Aasbakk, K.; Maeland, J. A. Journal of clinical microbiology 1992, 30, 1654.

(11) Hernandez, F. J.; Huang, L.; Olson, M. E.; Powers, K. M.; Hernandez, L. I.; Meyerholz, D. K.; Thedens, D. R.; Behlke, M. A.; Horswill, A. R.; McNamara, J. O., 2nd Nature medicine 2014, 20, 301.

(12) Burghardt, E. L.; Flenker, K. S.; Clark, K. C.; Miguel, J.; Ince, D.; Winokur, P.; Ford, B.; McNamara, J. O., II PloS one 2016, 11, e0157234.

(13) Mirkin, C. A.; Letsinger, R. L.; Mucic, R. C.; Storhoff, J. J. Nature 1996, 382, 607.

(14) Saha, K.; Agasti, S. S.; Kim, C.; Li, X.; Rotello, V. M. Chemical reviews 2012, 112, 2739.

(15) Lee, J. B.; Campolongo, M. J.; Kahn, J. S.; Roh, Y. H.; Hartman, M. R.; Luo, D. Nanoscale 2010, 2, 188.

(16) Seo, S.-H.; Lee, Y.-R.; Ho Jeon, J.; Hwang, Y.-R.; Park, P.-G.; Ahn, D.-R.; Han, K.-C.; Rhie, G.-E.; Hong, K.-J. Biosensors and Bioelectronics 2015, 64, 69.

(17) Sattarahmady, N.; Tondro, G. H.; Gholchin, M.; Heli, H. Biochemical Engineering Journal 2015, 97, 1.

(18) Xu, X.; Han, M. S.; Mirkin, C. A. Angewandte Chemie (International ed. in English) 2007, 46, 3468.

(19) Lee, J. S.; Han, M. S.; Mirkin, C. A. Angewandte Chemie (International ed. in English) 2007, 46, 4093.

(20) Liu, J.; Lu, Y. Journal of the American Chemical Society 2003, 125, 6642.

(21) Zhao, W.; Lam, J. C.; Chiuman, W.; Brook, M. A.; Li, Y. Small (Weinheim an der Bergstrasse, Germany) 2008, 4, 810.

(22) Guo, L.; Xu, Y.; Ferhan, A. R.; Chen, G.; Kim, D.-H. Journal of the American Chemical Society 2013, 135, 12338.

(23) Sanvicens, N.; Pastells, C.; Pascual, N.; Marco, M. P. TrAC Trends in Analytical Chemistry 2009, 28, 1243.

(24) Sung, Y. J.; Suk, H. J.; Sung, H. Y.; Li, T.; Poo, H.; Kim, M. G. Biosensors & bioelectronics 2013, 43, 432.

(25) Yuan, J.; Wu, S.; Duan, N.; Ma, X.; Xia, Y.; Chen, J.; Ding, Z.; Wang, Z. Talanta 2014, 127, 163.

(26) Chan, W. S.; Tang, B. S.; Boost, M. V.; Chow, C.; Leung, P. H. Biosensors & bioelectronics 2014, 53, 105.

(27) Wang, J.; Gao, J.; Liu, D.; Han, D.; Wang, Z. Nanoscale 2012, 4, 451.

(28) Beintema, J. J.; Schuller, C.; Irie, M.; Carsana, A. Progress in biophysics and molecular biology 1988, 51, 165.

(29) Syed, M. A.; Bokhari, S. H. Journal of biomedical nanotechnology 2011, 7, 229.

(30) Macfarlane, R. J.; Jones, M. R.; Senesi, A. J.; Young, K. L.; Lee, B.; Wu, J.; Mirkin, C. A. Angewandte Chemie (International ed. in English) 2010, 49, 4589.

(31) Hurst, S. J.; Lytton-Jean, A. K.; Mirkin, C. A. Analytical chemistry 2006, 78, 8313.

(32) Alexander, M.; Heppel, L. A.; Hurwitz, J. The Journal of biological chemistry 1961, 236, 3014.

(33) Cuatrecasas, P.; Fuchs, S.; Anfinsen, C. B. The Journal of biological chemistry 1967, 242, 3063.

(34) Raines, R. T. Chemical reviews 1998, 98, 1045.

(35) Marshall, G. R.; Feng, J. A.; Kuster, D. J. Biopolymers 2008, 90, 259.

(36) Alkilany, A. M.; Abulateefeh, S. R.; Mills, K. K.; Yaseen, A. I.; Hamaly, M. A.; Alkhatib, H. S.; Aiedeh, K. M.; Stone, J. W. Langmuir: the ACS journal of surfaces and colloids 2014, 30, 13799.

(37) Grilo Iê, R.; Ludovice, A. M.; Tomasz, A.; de Lencastre, H.; Sobral, R. G. MicrobiologyOpen 2014, 3, 247.

(38) Mackey-Lawrence, N. M.; Potter, D. E.; Cerca, N.; Jefferson, K. K. BMC Microbiology 2009, 9, 1.

(39) Ghssein, G.; Brutesco, C.; Ouerdane, L.; Fojcik, C.; Izaute, A.; Wang, S.; Hajjar, C.; Lobinski, R.; Lemaire, D.;

Richaud, P.; Voulhoux, R.; Espaillat, A.; Cava, F.; Pignol, D.; Borezee-Durant, E.; Arnoux, P. *Science* (New York, N.Y.) 2016, 352, 1105.

(40) Kiedrowski, M. R.; Crosby, H. A.; Hernandez, F. J.; Malone, C. L.; McNamara, J. O., 2nd; Horswill, A. R. PloS one; 2014, 9, e95574.;

(41) Hill, H. D.; Millstone, J. E.; Banholzer, M. J.; Mirkin, C. A. ACS nano 2009, 3, 418.

V. EMBODIMENTS

Embodiment 1. A functionalized nanoparticle comprising a nanoparticle core and a nanoparticle coating, wherein said nanoparticle coating comprises: a plurality of nucleic acid moieties bonded to said nanoparticle core, wherein each of said nucleic acid moieties comprises: (i) a first linker binding said nucleic acid moiety to said nanoparticle core; and (ii) a single-stranded nucleic acid sequence of about 50 or less nucleotides in length covalently attached to said first linker, wherein said single-stranded nucleic acid sequence comprises a nuclease cleavage site.

Embodiment 2. The functionalized nanoparticle of embodiment 1, wherein said nanoparticle core is about 3 to about 20 nm in length.

Embodiment 3. The functionalized nanoparticle of embodiment 1 or 2, wherein said nanoparticle core is an inorganic nanoparticle core.

Embodiment 4. The functionalized nanoparticle one of embodiments 1-3, wherein said nanoparticle core is a metal nanoparticle core.

Embodiment 5. The functionalized nanoparticle of embodiment 4, wherein said metal nanoparticle core comprises titanium, zirconium, gold, silver, platinum, cerium, arsenic, iron, aluminum or silicon.

Embodiment 6. The functionalized nanoparticle of embodiment 5, wherein said metal nanoparticle core is a gold nanoparticle core.

Embodiment 7. The functionalized nanoparticle of embodiment 1 or 2, wherein said nanoparticle core is a polymeric core.

Embodiment 8. The functionalized nanoparticle of one of embodiments 1-7, wherein said nanoparticle core comprises an outer shell layer and an inner layer, wherein said outer shell layer is chemically distinct from said inner layer.

Embodiment 9. The functionalized nanoparticle of one of embodiments 1-8, wherein said first linker is a bond, —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence linker; R$^1$, R$^2$, R$^3$, R$^4$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2.

Embodiment 10. The functionalized nanoparticle of one of embodiments 1-9, wherein said single-stranded nucleic acid sequence is about 40 or less nucleotides in length.

Embodiment 11. The functionalized nanoparticle of one of embodiments 1-10, wherein said single-stranded nucleic acid sequence is about 30 or less nucleotides in length.

Embodiment 12. The functionalized nanoparticle of one of embodiments 1-11, wherein said single-stranded nucleic acid sequence is about 20 or less nucleotides in length.

Embodiment 13. The functionalized nanoparticle of one of embodiments 1-12, wherein said single-stranded nucleic acid sequence is about 15 or less nucleotides in length.

Embodiment 14. The functionalized nanoparticle of one of embodiments 1-13, wherein said single-stranded nucleic acid sequence is about 11 nucleotides in length.

Embodiment 15. The functionalized nanoparticle of one of embodiments 1-14, wherein said single-stranded nucleic acid sequence comprises a modified nucleotide.

Embodiment 16. The functionalized nanoparticle of embodiment 15, wherein said modified nucleotide is a 2'O-methylated nucleotide.

Embodiment 17. The functionalized nanoparticle of one of embodiments 1-16, wherein said nuclease cleavage site comprises an unmodified nucleotide.

Embodiment 18. The functionalized nanoparticle of embodiment 17, wherein said unmodified nucleotide is a deoxythymidine.

Embodiment 19. The functionalized nanoparticle of one of embodiments 1-18, wherein said nuclease cleavage site is a bacterial nuclease cleavage site.

Embodiment 20. The functionalized nanoparticle of embodiment 19, wherein said nuclease cleavage site is a micrococcal nuclease cleavage site.

Embodiment 21. The functionalized nanoparticle of one of embodiments 1-20, wherein each of said nucleic acid moieties further comprises a water soluble moiety covalently attached to said single-stranded nucleic acid sequence through a second linker.

Embodiment 22. The functionalized nanoparticle of embodiment 21, wherein said water soluble moiety is a water soluble polymer moiety.

Embodiment 23. The functionalized nanoparticle of embodiment 22, wherein said water soluble polymer moiety is a biopolymer moiety, an alkylpolyamine moiety, an alkylpolyamide moiety, an alkylpolyether moiety, an alkylpolysulfonates moiety, a polyacrylamide moiety, a carbohydrate moiety or an alkylpolyalcohol moiety.

Embodiment 24. The functionalized nanoparticle of embodiment 23, wherein said alkylpolyether moiety is a PEG moiety.

Embodiment 25. The functionalized nanoparticle of one of embodiments 21-24, wherein said second linker is a bond, —C(O)—, —C(O)O—, —O—, —S—, —NH—, —NR$^{1.A}$—, —C(O)NR$^{2.A}$—, —S(O)$_{n.1}$—, —S(O)NR$^{3.A}$—, —OP(O)(OR$^{4.A}$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence linker; R$^{1.A}$, R$^{2.A}$, R$^{3.A}$, R$^{4.A}$ are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n.1 is independently 1 or 2.

Embodiment 26. A plurality of functionalized nanoparticles, wherein each functionalized nanoparticle is a functionalized nanoparticle of one of embodiments 1-25.

Embodiment 27. The plurality of functionalized nanoparticles of embodiment 26, wherein said nanoparticles are in a vessel.

Embodiment 28. The plurality of functionalized nanoparticles of embodiment 27, wherein said vessel is in a spectrophotometry device.

Embodiment 29. A method of forming a nanoparticle aggregate, said method comprising: (i) contacting a nuclease with the plurality of functionalized nanoparticles of embodiment 26; and (ii) allowing said nuclease to cleave said single-stranded nucleic acid sequence at said nuclease cleavage site of said plurality of functionalized nanoparticles, thereby forming a nanoparticle aggregate.

Embodiment 30. The method of embodiment 29, further comprising detecting said nanoparticle aggregate.

Embodiment 31. The method of embodiment 30, wherein said detecting comprises colorimetric detection of said nanoparticle aggregate.

Embodiment 32. The method of embodiment 27, wherein said allowing of step (ii) comprises forming a plurality of cleaved functionalized nanoparticles comprising a cleaved single-stranded nucleic acid sequence.

Embodiment 33. The method of embodiment 32, wherein said cleaved single-stranded nucleic acid sequence is less than about 20 nucleotides in length.

Embodiment 34. The method of embodiment 32 or 33, wherein said cleaved single-stranded nucleic acid sequence is less than about 10 nucleotides in length.

Embodiment 35. The method of one of embodiments 32-34, wherein said cleaved single-stranded nucleic acid sequence is about 5 nucleotides in length.

and the nanoparticle coating comprises a plurality of nucleic acid moieties bonded to said nanoparticle core; and wherein each of said nucleic acid moieties comprises:
(a) a first linker binding said nucleic acid moiety to said nanoparticle core; and
(b) said single-stranded nucleic acid sequence of about 50 or less nucleotides in length covalently attached to said first linker;

wherein:
(i) said single-stranded nucleic acid sequence comprises said nuclease cleavage site;
(ii) said nuclease cleavage site is a bacterial nuclease cleavage site recognized by a bacterial nuclease;
(iii) said single-stranded nucleic acid sequence comprises a plurality of modified nucleotides;
(iv) said single-stranded nucleic acid sequence is more resistant to cleavage in serum lacking the bacterial nuclease as compared to the single-stranded nucleic acid sequence without the plurality of modified nucleotides; and
(v) said single-stranded nucleic acid sequence does not comprise a fluorescent label, a luminescent label, or a phosphorescent label.

2. The method of claim 1, wherein said detecting comprises colorimetric detection of said nanoparticle aggregate.

3. The method of claim 1, wherein said allowing of step (ii) comprises forming a plurality of cleaved functionalized nanoparticles comprising a cleaved single-stranded nucleic acid sequence.

4. The method of claim 3, wherein said cleaved single-stranded nucleic acid sequence is less than about 20 nucleotides in length.

What is claimed is:

1. A method of detecting a nanoparticle aggregate, said method comprising:
   (i) contacting a nuclease with a plurality of functionalized nanoparticles; and
   (ii) allowing said nuclease to cleave a single-stranded nucleic acid sequence at a nuclease cleavage site of said plurality of functionalized nanoparticles, thereby forming a nanoparticle aggregate;
   wherein each of said functionalized nanoparticles comprises a nanoparticle core and a nanoparticle coating, 5. The method of claim 3, wherein said cleaved single-stranded nucleic acid sequence is less than about 10 nucleotides in length.

6. The method of claim 3, wherein said cleaved single-stranded nucleic acid sequence is about 5 nucleotides in length.

7. The method of claim 1, wherein said nanoparticle core is an inorganic nanoparticle core.

8. The method of claim 1, wherein said nanoparticle core is a metal nanoparticle core.

9. The method of claim 8, wherein said metal nanoparticle core comprises titanium, zirconium, gold, silver, platinum, cerium, arsenic, iron, aluminum or silicon.

10. The method of claim 8, wherein said metal nanoparticle core is a gold nanoparticle core.

11. The method of claim 1, wherein:
said first linker is a bond, —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, an amino acid sequence linker, or a nucleic acid sequence linker;
R$^1$, R$^2$, R$^3$ and R$^4$, are independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
n is 1 or 2.

12. The method of claim 1, wherein said nanoparticles are in a vessel.

13. The method of claim 12, wherein said vessel is in a spectrophotometry device.

14. The method of claim 1, wherein said plurality of modified nucleotides comprise 2'O-methylated nucleotides.

15. The method of claim 1, wherein said single-stranded nucleic acid sequence comprises at least one modified nucleotide 5' of said nuclease site and at least one modified nucleotide 3' of said nuclease cleavage site.

16. The method of claim 1, further comprising detecting bacteria.

17. The method of claim 16, wherein the bacteria is *staphylococcus* bacteria.

* * * * *